US012089881B2

(12) United States Patent  
Olea et al.

(10) Patent No.: US 12,089,881 B2  
(45) Date of Patent: Sep. 17, 2024

(54) SPINAL TRAUMA CORRECTION AND FIXATION

(71) Applicant: NuVasive, Inc., San Diego, CA (US)

(72) Inventors: Fernando Olea, San Diego, CA (US); Brad Anderson, San Diego, CA (US); Scott Lish, San Diego, CA (US); Michele M. Johnson, Atlanta, GA (US); Andrew Morris, San Diego, CA (US)

(73) Assignee: NuVasive, Inc., San Diego, CA (US)

(*) Notice: Subject to any disclaimer, the term of this patent is extended or adjusted under 35 U.S.C. 154(b) by 635 days.

(21) Appl. No.: 17/123,343

(22) Filed: Dec. 16, 2020

(65) Prior Publication Data

US 2021/0128204 A1 May 6, 2021

Related U.S. Application Data

(63) Continuation of application No. 15/678,877, filed on Aug. 16, 2017, now Pat. No. 10,898,239, which is a continuation of application No. PCT/US2017/030282, filed on Apr. 28, 2017.

(60) Provisional application No. 62/357,941, filed on Jul. 1, 2016.

(51) Int. Cl.
A61B 17/70 (2006.01)
A61B 17/00 (2006.01)
A61B 17/56 (2006.01)
A61B 17/68 (2006.01)

(52) U.S. Cl.
CPC ...... A61B 17/7079 (2013.01); A61B 17/7001 (2013.01); A61B 17/7077 (2013.01); A61B 2017/00407 (2013.01); A61B 2017/564 (2013.01); A61B 2017/681 (2013.01)

(58) Field of Classification Search
CPC .......... A61B 17/7079; A61B 2090/064; A61B 2017/565; A61B 17/8869
USPC .................. 606/250–279, 86 A, 102–105
See application file for complete search history.

(56) References Cited

U.S. PATENT DOCUMENTS

| 5,201,734 | A | 4/1993 | Cozad et al. |
| 5,741,261 | A | 4/1998 | Moskovitz et al. |
| 7,597,694 | B2 | 10/2009 | Lim et al. |
| 7,611,522 | B2 | 11/2009 | Gorek |

(Continued)

FOREIGN PATENT DOCUMENTS

| AU | 2012200106 A1 | 2/2012 |
| CN | 200987699 Y | 12/2007 |

(Continued)

OTHER PUBLICATIONS

International Search Report for PCT/US2017/030282, ISA, mailed Dec. 1, 2017, pp. 5.

(Continued)

Primary Examiner — Eduardo C Robert  
Assistant Examiner — Tara Rose E Carter

(57) ABSTRACT

Tools and techniques are described that are useful for trauma correction of anterior compression, chance, or burst fractures, particularly where the posterior longitudinal ligament and posterior arch anatomy is still intact. The described tools can be used to reduce fracture and provide additional distraction for ligamentum taxis through a posterior approach that is compatible with both open and minimally invasive methodologies.

20 Claims, 40 Drawing Sheets

(56) References Cited

U.S. PATENT DOCUMENTS

| | | |
|---|---|---|
| 7,914,536 B2 | 3/2011 | MacDonald et al. |
| 7,922,731 B2 | 4/2011 | Schumacher et al. |
| 7,947,046 B2 | 5/2011 | Justis et al. |
| 7,981,115 B2 | 7/2011 | Justis et al. |
| 7,998,144 B2 | 8/2011 | Schumacher et al. |
| 8,657,825 B2 | 2/2014 | Justis et al. |
| 8,702,713 B2 | 4/2014 | Nayet et al. |
| 8,906,034 B2 | 12/2014 | Gleeson et al. |
| 8,911,442 B2 | 12/2014 | Wing et al. |
| 9,125,703 B2 | 9/2015 | McClintock et al. |
| 9,161,787 B2 | 10/2015 | Wolinsky et al. |
| 9,198,698 B1 | 12/2015 | Doose et al. |
| 9,211,149 B2 | 12/2015 | Hoefer et al. |
| 9,402,660 B2 | 8/2016 | Brinkman et al. |
| 9,480,504 B1 | 11/2016 | Schafer et al. |
| 9,649,140 B1 | 5/2017 | Doose et al. |
| 9,907,582 B1 | 3/2018 | Olea |
| 10,898,239 B2 * | 1/2021 | Olea .................. A61B 17/7001 |
| 2003/0199872 A1 | 10/2003 | Markworth et al. |
| 2005/0065517 A1 * | 3/2005 | Chin .................. A61B 17/708 |
| | | 606/279 |
| 2005/0245928 A1 * | 11/2005 | Colleran ............. A61B 17/708 |
| | | 606/86 A |
| 2006/0085010 A1 | 4/2006 | Lieberman |
| 2008/0077139 A1 * | 3/2008 | Landry ................ A61F 2/4611 |
| | | 606/103 |
| 2008/0077155 A1 | 3/2008 | Diederich et al. |
| 2008/0125788 A1 | 5/2008 | Cohen et al. |
| 2008/0147079 A1 | 6/2008 | Chin et al. |
| 2009/0076515 A1 | 3/2009 | Lamartina et al. |
| 2010/0082066 A1 | 4/2010 | Biyani |
| 2010/0087823 A1 | 4/2010 | Kondrashov |
| 2010/0274252 A1 | 10/2010 | Bottomley et al. |
| 2012/0071885 A1 | 3/2012 | Forton et al. |
| 2012/0143189 A1 | 6/2012 | Wolfson |
| 2012/0191143 A1 | 7/2012 | Nayet et al. |
| 2013/0184763 A1 * | 7/2013 | McClintock ......... A61B 17/708 |
| | | 606/279 |
| 2013/0245692 A1 | 9/2013 | Hayes et al. |
| 2013/0289633 A1 | 10/2013 | Gleeson et al. |
| 2014/0039567 A1 | 2/2014 | Hoefer et al. |
| 2014/0107659 A1 | 4/2014 | Walters et al. |
| 2015/0066088 A1 | 3/2015 | Brinkman et al. |
| 2015/0351814 A1 | 12/2015 | McClintock et al. |
| 2016/0183933 A1 | 6/2016 | Hayes et al. |
| 2017/0079689 A1 | 3/2017 | Prevost |

FOREIGN PATENT DOCUMENTS

| | | |
|---|---|---|
| CN | 201337505 Y | 11/2009 |
| CN | 201642304 U | 11/2010 |
| CN | 202699270 U | 1/2013 |
| CN | 202723973 | 2/2013 |
| DE | 202012100745 U1 | 4/2012 |
| DE | 102012101780 A1 | 9/2020 |
| EP | 0528177 A2 | 2/1993 |
| JP | 4810698 B1 | 11/2011 |
| WO | 2015137976 A1 | 9/2015 |

OTHER PUBLICATIONS

Written Opinion for PCT/US2017/030282, ISA, mailed Dec. 1, 2017, pp. 9.

* cited by examiner

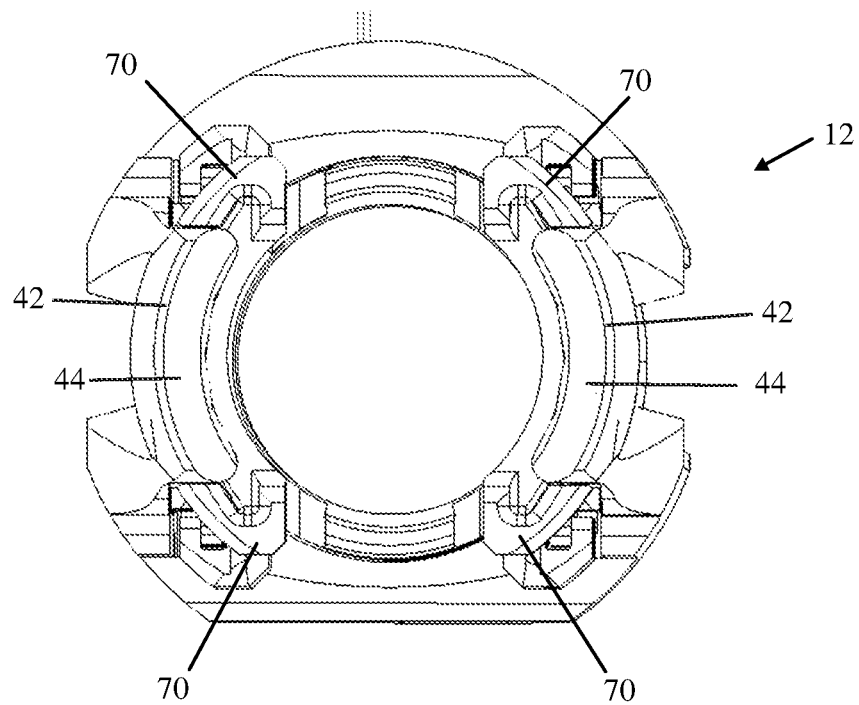
FIG. 10
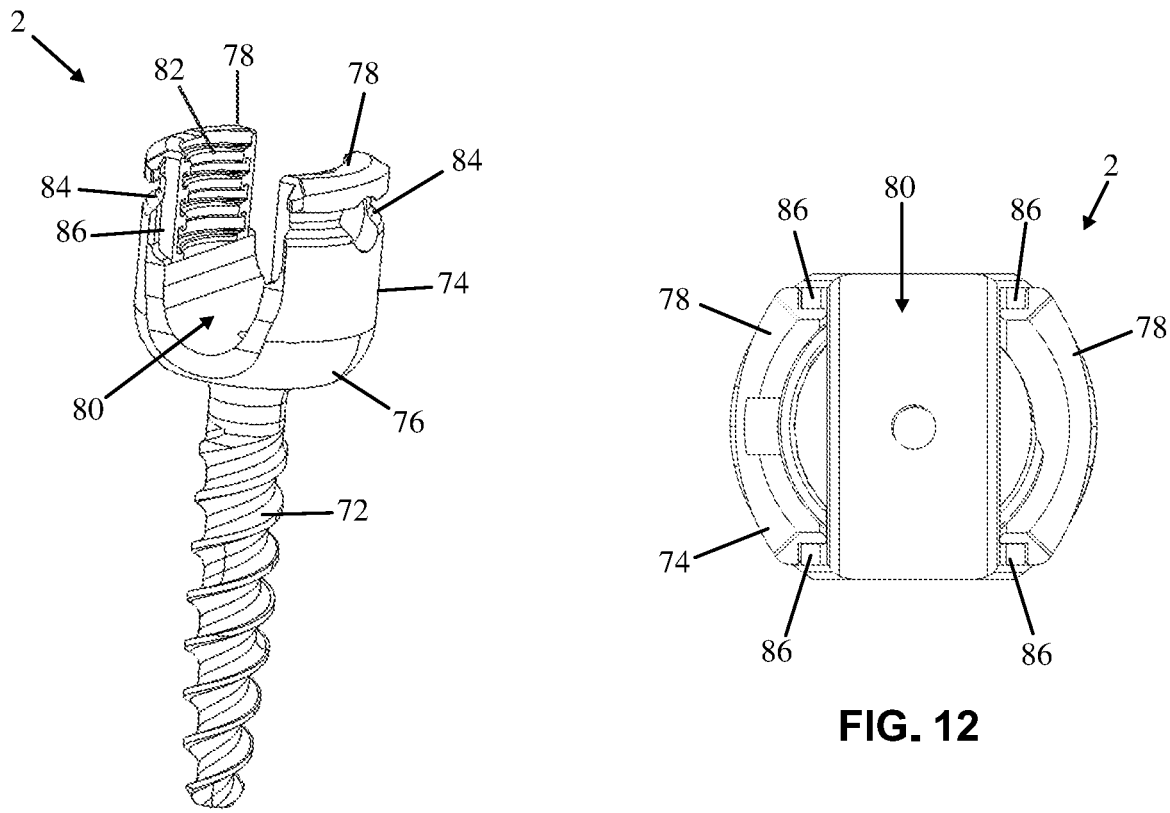
FIG. 11
FIG. 12

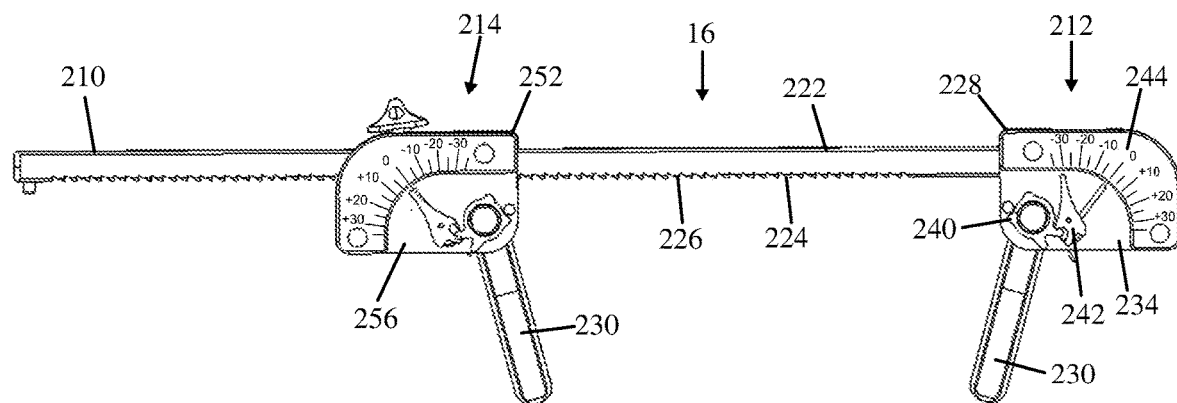
FIG. 25
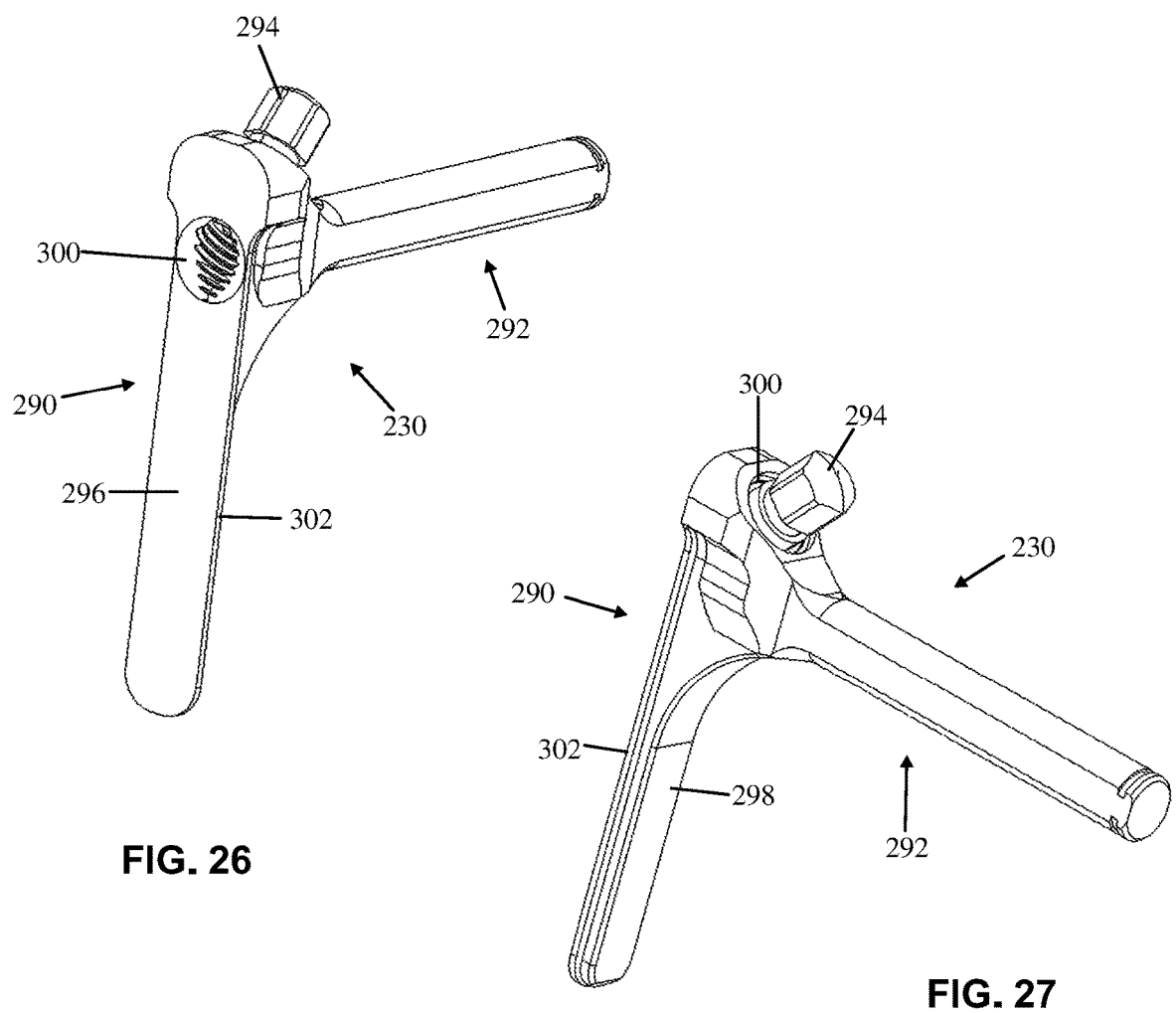
FIG. 26
FIG. 27

SPINAL TRAUMA CORRECTION AND FIXATION

CROSS-REFERENCE TO RELATED APPLICATIONS

This application is a continuation of U.S. patent application Ser. No. 15/678,877 filed Aug. 16, 2017, which is a continuation of International Application PCT/US2017/030282, filed on 28 Apr. 2017, which claims the benefit of priority to U.S. Provisional Application Ser. No. 62/357,941, filed on 1 Jul. 2016, which are incorporated by reference herein in their entirety.

FIELD

The present disclosure relates generally to medical devices, more specifically to the field of spinal surgery and spinal fixation devices. Such devices as well as systems and methods for use therewith are described.

BACKGROUND

The spine is critical in human physiology for mobility, support, and balance. The spine protects the nerves of the spinal cord, which convey commands from the brain to the rest of the body, and convey sensory information from the nerves below the neck to the brain. Even minor spinal injuries can be debilitating to the patient, and major spinal injuries can be catastrophic. The loss of the ability to bear weight or permit flexibility can immobilize the patient. Even in less severe cases, small irregularities in the spine can put pressure on the nerves connected to the spinal cord, causing devastating pain and loss of coordination.

Posterior spinal fixation constructs are often utilized to provide stability to the spine. Most often the fixation construct is used as an adjunct to fusion surgery during which adjacent vertebrae are prepared to facilitate bone growth between them, thereby eliminating motion between the vertebrae. Although this is the primary design purpose of widely used posterior spinal fixation constructs, they are sometimes used for the correction of traumatic injury to anterior vertebral bodies. Such injuries include compression fractures, chance fractures, and burst fractures. Permanent fusion is not the primary goal when attempting to repair such traumatic injury. The primary goal is to reorient the damaged spinal structures to facilitate healing of the bone. Anchors are anchored to the vertebral structures flanking the injury posteriorly and joined with a rod. The anchors are then manipulated about the rod to compress, distract, and/or angulate the associated vertebral bodies to achieve the desired correction. While generally effective, the ability to achieve the desired correction is oftentimes limited by the presence of the rod, which permits limited movement of the anchors before they bottom out or run against the rod. The instruments, tools, and techniques described herein are directed towards reducing these challenges and others associated with posterior spinal fixation.

SUMMARY

The tools and techniques described herein are useful for trauma correction of compression, chance, burst and dislocated fractures through a posterior approach. The described tools can be used to reduce the fracture, moving the affected vertebral bodies back towards anatomic alignment, and providing additional distraction for ligamentum taxis (clearing spinal canal by stretching PLL) or compression for moving the posterior elements back into alignment through a posterior approach that is compatible with both open, hybrid, and minimally invasive methodologies.

A system for the correction of vertebral trauma is provided. In a first general embodiment the system comprises: a first and a second anchor guide member configured to fixedly attach to a first and a second bone anchor assembly, respectively, each of the first and second guide members having a proximal end and a distal end; a pivot rack connected to the first and second guide members to allow the first and second guide members to rotate relative to one another about one respective axis each at the distal ends of the first and second guide members; a locking rack connected to the first and second guide members, configured to reversibly prevent the guide members from rotating relative to one another in at least one direction; and a first and second bone anchor assembly connected to the distal ends of the first and second guide members to restrict the translation and angulation about at least one axis of the bone anchor assemblies relative to the guide members.

In a second general embodiment, the system comprises a pivot rack that includes a first and a second arm unit, each said arm unit comprising a distal attachment element configured to attach to a respective first and second guide member so as to allow said first and second guide members to rotate relative to one another about one axis each at the distal ends of the first and second guide members, wherein the first and second arm units are constrained from translating relative to the guide member; and a proximal engagement feature; a first pivot arm assembly fixedly connected to the first arm unit, an elongate pivot rack member with a first end and a second end, the first pivot arm assembly fixedly attached to the first end, a second pivot arm assembly translatably attached to the elongate pivot rack member, and fixedly connected to the second arm unit; a locking rack to maintain the relative distance of the guide assemblies, said locking rack comprising an elongate locking rack member, a first connector arm assembly connected to the elongate locking rack member, the first connector arm assembly comprising a first connector arm configured to attach to the first guide member, wherein the first connector arm assembly is configured to allow the first connector arm to rotate about a first axis relative to the first connector arm assembly, and wherein the first connector arm assembly is configured to allow the first connector arm to translate along said first axis relative to the first connector arm assembly; and a second connector arm assembly slideably connected to the elongate locking rack member, the second connector arm assembly comprising a second connector arm configured to attach to the second guide member, wherein the second connector arm assembly is configured to allow the second connector arm to rotate about a second axis relative to the second connector arm assembly, and wherein the second connector arm assembly is configured to allow the second connector arm to translate along said second axis relative to the second connector arm assembly, and a locking mechanism that reversibly locks the second connector arm assembly against sliding relative to the elongate locking rack member in at least one direction.

A guide member for positioning and angulating a bone anchor assembly is provided, the guide assembly comprising: a proximal guide end and a distal guide end; a lumen extending from the proximal guide end to the distal guide end; a pair of opposed longitudinal rod slots opening to the distal end and extending proximally for a length along the guide member and contiguous with the lumen, to form a rod channel dimensioned to guide a spinal rod into the bone anchor; a bone anchor engagement feature at the distal end; and a side track extending longitudinally between the pair of opposed longitudinal rod slots.

A pivot rack for controlling the distance between two bone anchors during spinal surgery is provided, the pivot rack comprising: a first and a second arm unit each having first and second ends, each comprising a guide member attachment feature at the first end and an arm assembly attachment feature at the second end; a first and second pivot arm assembly each engaged to the respective first and second arm units at the arm assembly attachment features, and comprising an arm unit engagement feature capable of reversibly locking the rotation of the arm units relative to the arm assemblies; an elongated rack member engaged to the first and second pivot arm assemblies; and a translation unit configured to translate the second pivot arm assembly along the elongated rack member.

A locking rack for controlling the orientation of a first and a second guide member is provided, the locking rack comprising: an elongate locking rack member having a first end and a second end; a first locking arm assembly attached to the elongate locking rack member; a first locking arm member attached to the first locking arm assembly and configured to attach to a first guide member; a second locking arm assembly slideably attached to the elongate locking rack member, and comprising a locking mechanism to reversibly prohibit the second locking arm assembly from sliding relative to the elongate locking rack member in at least one direction; and a second locking arm member rotatably attached to the second locking arm assembly and configured to attach to a second guide member.

A method of repairing spinal trauma in a subject is provided, the method comprising: anchoring a first bone anchor assembly to a first vertebral structure; anchoring a second bone anchor assembly to a second vertebral structure; fixedly connecting a first guide member to the first bone anchor assembly, said first guide member having a distal end and a proximal end; fixedly connecting a second guide member to the second bone anchor assembly, said second guide member having a distal end and a proximal end; connecting a pivot rack to both of the first and second guide members, the pivot rack configured to allow the first and second guide members to rotate relative to one another about a first and second axis respectively, said first and second axes passing through the distal ends of the respective first and second guide members, and comprising a translation unit that controls the translation of the distal ends of the first and second guide members relative to one another; connecting a locking rack to both of the first and second guide members, the locking rack configured to reversibly prevent the guide members from rotating relative to one another in at least one direction; correcting the alignment of the first and second vertebral structures by at least one of angulation, distraction, and compression, wherein said angulation involves rotating the first and second guide members relative to one another about said respective first and second axes to effect angulation of the first and second vertebral structures; wherein said distraction and compression involves translating the distal ends of the first and second guide members relative to one another; and fixedly emplacing a spinal rod into the first and second bone anchor assemblies to maintain said at least one of angulation, distraction, and compression.

The above presents a simplified summary in order to provide a basic understanding of some aspects of the claimed subject matter. This summary is not an extensive overview. It is not intended to identify key or critical elements or to delineate the scope of the claimed subject matter. Its sole purpose is to present some concepts in a simplified form as a prelude to the more detailed description that is presented later.

BRIEF DESCRIPTION OF THE DRAWINGS

FIG. 10. A plan view of the distal end of the guide assembly of FIG. 5.

FIG. 11. A perspective view of an example of a fixed angle bone anchor forming part of the spinal fixation/correction system of FIG. 1.

FIG. 12. A top plan view of the fixed angle bone anchor of FIG. 11.

FIG. 25. A plan view of the example locking rack assembly of FIG. 23.

FIG. 26. A first perspective view of an arm unit forming part of the example locking rack assembly of FIG. 23.

FIG. 27. A second perspective view of an arm unit forming part of the example locking rack assembly of FIG. 23.

DETAILED DESCRIPTION

Figure 1:
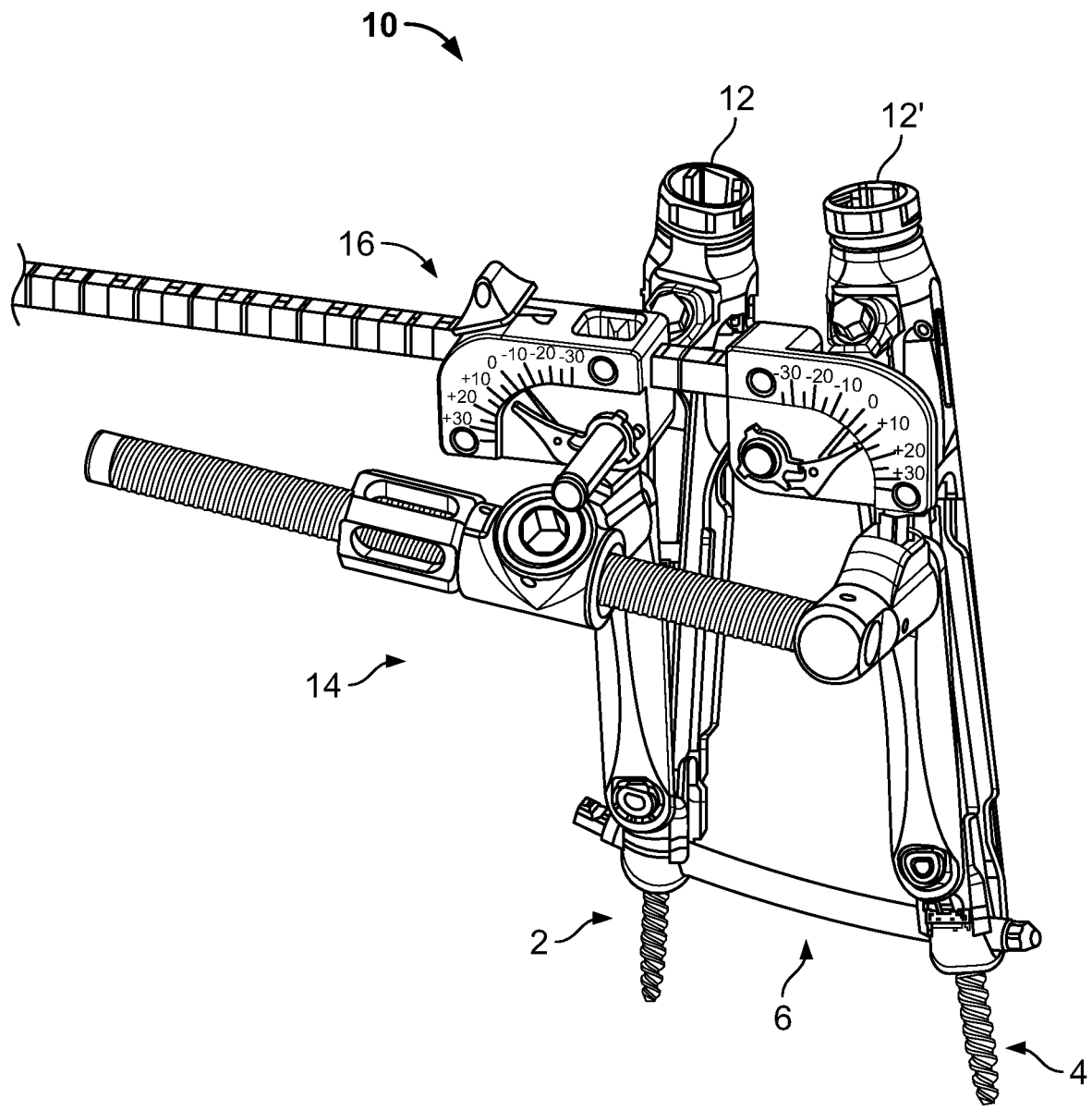
FIG. 1. A perspective view of an example of a spinal fixation/correction system in use with a spinal construct implanted on a portion of a spine, according to one embodiment.
Figure 2:
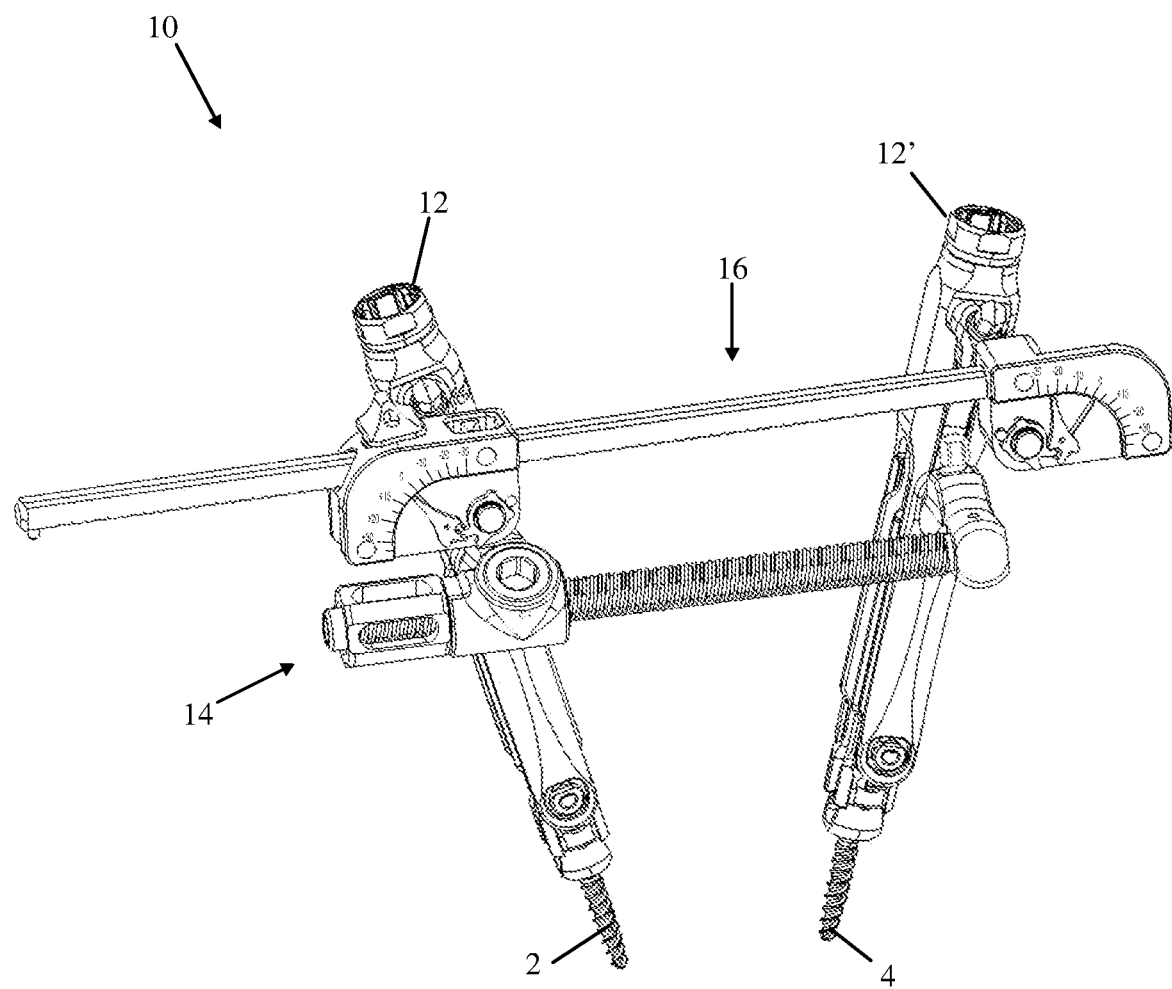
FIG. 2. A perspective view of the example spinal fixation/correction system of FIG. 1.
Figure 3:
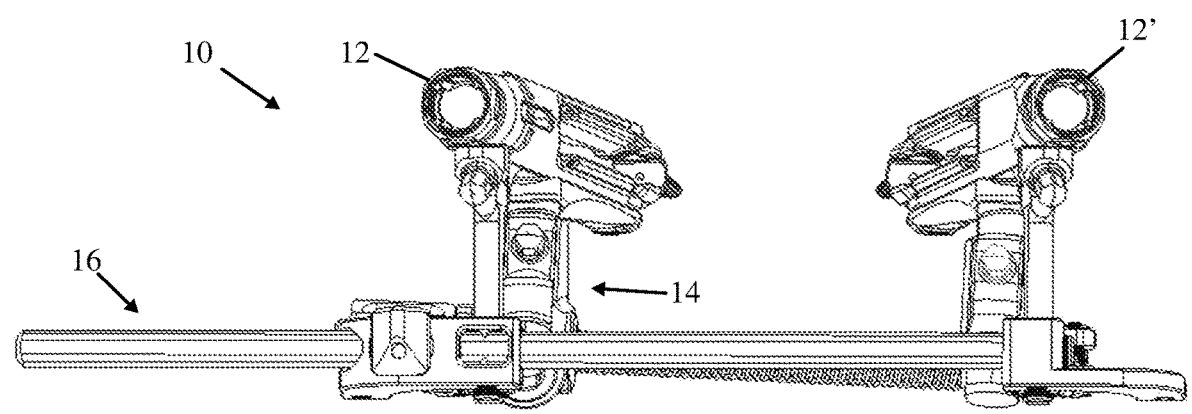
FIG. 3. Top view of the example spinal fixation/correction system of FIG. 1.
Figure 4:
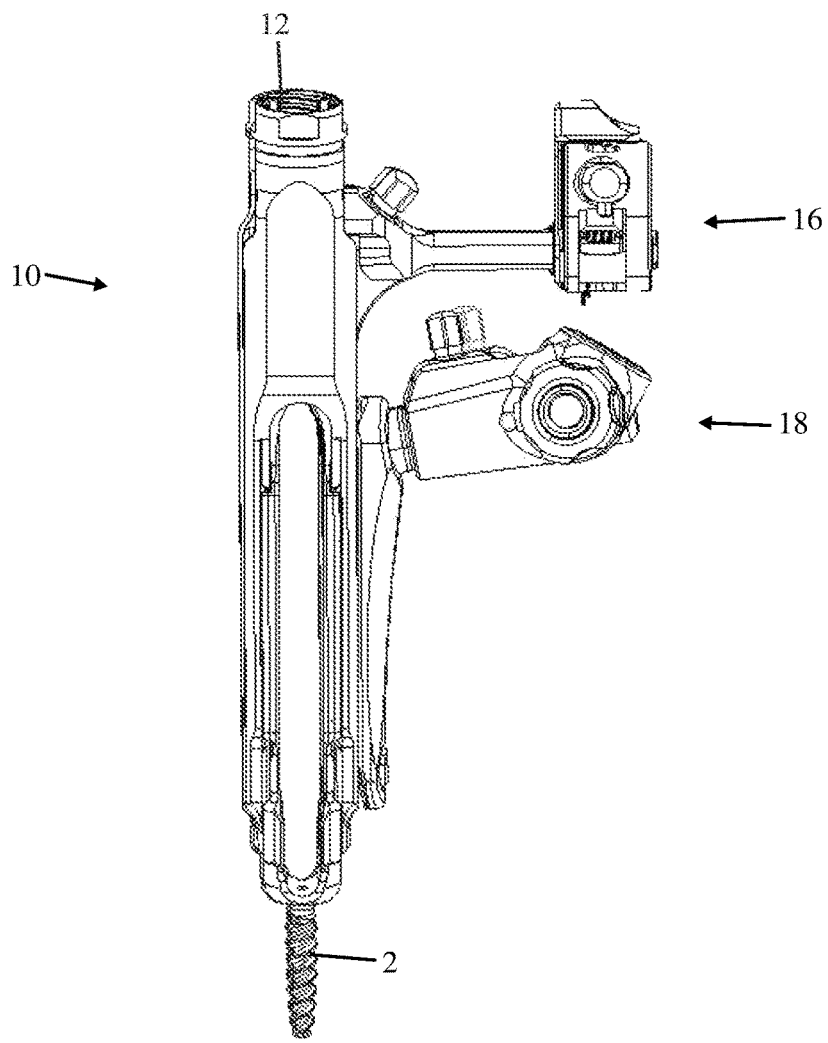
FIG. 4. Side view of the example spinal fixation/correction system of FIG. 1.
Figure 5:
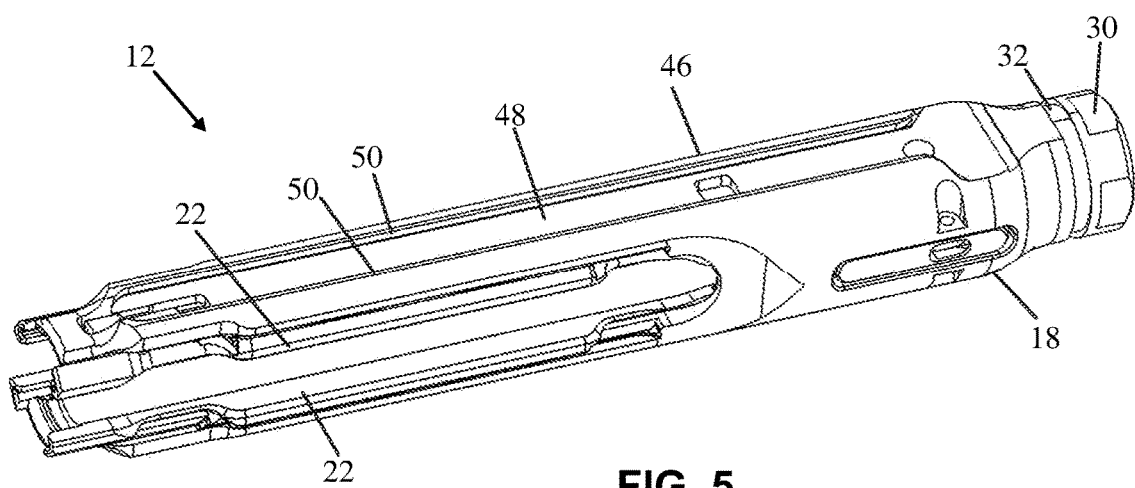
FIG. 5. A perspective view of an example of a guide assembly forming part of the example spinal fixation/correction system of FIG. 1.

Illustrative embodiments of tools and methods for spinal trauma correction and fixation are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The tools and methods for spinal trauma correction and fixation disclosed herein boast a variety of inventive features and components that warrant patent protection, both individually and in combination.

It is to be understood that any given elements of the disclosed embodiments of the invention may be embodied in a single structure, a single step, a single substance, or the like. Similarly, a given element of the disclosed embodiment may be embodied in multiple structures, steps, substances, or the like.

A system for the correction of vertebral trauma is provided. The system uses at least two bone anchor guides 12, 12' connected with a dual rack construct. By way of example, the system may be used during a trauma surgery to apply a correction to the implicated vertebrae. During the surgery a first bone anchor assembly 2 is implanted into a first vertebra V1, and a second bone anchor assembly 4 is implanted into a second vertebra V2. A lower (distal) rack (pivot rack) 14 provides a fixed distance between the anchors that prevents accidental compression, protecting the spinal canal, while providing the ability to intentionally distract and compress. The pivot rack and guide connection allows for the guides to pivot and correct vertebral body angulation while maintaining the fixed screw to screw distance. A top (proximal) rack (locking rack) 16 provides for the ability to maintain the correction achieved through the relative angulation of the bone anchor assemblies without the necessity for a spinal rod 6, and provides an indication of the distance and angle between the anchors. A spinal rod 6 is then inserted into the bone anchor assemblies 2, 4, and reducers may be used to provide rod reduction while the dual racks remain in place.

In use, the bone anchor assemblies 2, 4 are implanted with their associated guides 12, 12' attached. In some embodiments of the system one or both guide members 12, 12' may be integral with the bone anchor assembly 2, for example if a reduction tube screw is used. The pivot rack 14 is attached to the guides and the locking rack 16 is attached to the guides 12, 12'. The proximal ends of the guides are converged (or in some cases spread if compression is needed) to provide angulation correction to the vertebral bodies. Locking the locking rack 16 to restrict relative movement of the guides 12, 12' in at least one direction allows angulation correction to be generally maintained prior to rod insertion. The pivot rack 14 may be used to apply additional distraction (ligamentum taxis) or compression. The locking rack 16 may be equipped with indicators to assist in determining the required rod length and bend, and then the rod 6 is inserted. Reducers may be used to reduce the rod 6 until fully seated in the bone anchor assembly 2, at which point it is locked down with lock screws 365. Racks and guides may be removed.

The two ("first" and "second") anchor guide members 405a, 405b are configured to fixedly attach to rod housings 74 of the two ("first" and "second") bone anchor assemblies 2, 4, respectively. The fixed attachment does not permit relative movement between the anchor guide 12 and the housing 74. When the housing 74 is in turn fixed relative to the anchor portion (e.g. as with a fixed screw or a provisional locking screw in locked configuration) the bone anchor 2 and the vertebra in which it is implanted will rotate and translate together with the associated guide assembly 12. Such attachment is of course temporary and reversible, to allow the bone anchor assemblies 2, 4 to remain implanted in the bone structure after the guide members have been withdrawn. In a preferred arrangement the guide assembly 12 may be coupled to the bone anchor prior to implantation and advanced with the bone anchor. Alternatively, the bone anchor assembly 2 implanted in the appropriate position first and thereafter, the guide member 12 may be advanced distally to the bone anchor assembly 2 and coupled in situ.

FIGS. 5-10 illustrate an example of a guide assembly 12 for use with the system described above. By way of example only, the guide assembly 12 includes an outer sleeve 18 and a pair of independent inner arm members 22 positioned within the outer sleeve 18, and a locking actuator. In the illustrated embodiment, the outer sleeve 18 is a generally tubular member having a proximal end 24, a distal end 26, and a lumen 28 extending longitudinally through the outer sleeve 18. The proximal end 24 includes one or more tool engagement features (e.g. shaped end 30 and circumferential groove 32) configured to engage one or more additional instruments and/or accessories on the outside of the outer sleeve 18, such that the guide assembly 12 may be releasably coupled to the one or more additional instruments as needed. The outer sleeve 18 further includes a pair of longitudinal rod slots 34 extending proximally from the distal end 26 of the outer sleeve 18. The longitudinal rod slots 34 act in concert to form a channel 36 to guide the spinal rod 6 to the surgical target site during implantation of the surgical fixation construct. By way of example only, the slots 34 extend a little over half way along the outer sleeve 18. The slots 34 effectively divide the distal portion of the outer sleeve 18 into first and second outer arms 38. Side extensions 355 extend out laterally from each side arm of both outer arms 38, the side extensions mating with complementary features on the inner arm members 22 to couple the inner arms to the outer sleeve while allowing the arm members 22 to translate relative to the outer sleeve 18. The distal end of the outer arms 38 each includes a distal extension 40. The distal extension 40 is an extension of the outer sleeve 18 however it is narrower in width than the outer sleeve 18. A ridge 42 dimensioned to engage the housing 74 of the bone anchor assembly 2 (e.g., a pedicle screw) is positioned on the interior surface of the distal extension 40. The ridge 42 is configured to engage the attachment groove 84 of the housing 74 to releasably lock the guide assembly 12 to the pedicle screw 2. The ridge 42 includes a tapered surface 44 that enables the ridge 42 to slide over the top of the housing 74 of the pedicle screw 2 during the engagement process.

The inner arm members 22 are each comprised of an elongated partially-cylindrical member 63 having a proximal end 64 and a distal end 66. Each arm includes wings 360 extending outward from side surfaces along at least a portion of the arm. Each wing 360 forms an interior slot 362 that slideably receives the side extensions 355 of the outer sleeve arms to couple the arms to the outer sleeve. Flanges 68 on the proximal end of each arm interact with an actuator to facilitate translation of inner arm members 22. The distal ends 66 of the inner arm members 22 are configured to securely receive the top of the housing 74 of the pedicle screw 2. To facilitate this secure engagement, the distal ends 66 of the inner arm members 22 include a plurality of prongs 70 configured to extend vertically along the sides of the housing 74 upon engagement, and more specifically with lateral recesses 86. The prongs 70 act to prevent rotation of the housing 74 of the pedicle screw 2 during implantation of the spinal fixation construct.

The arm members 22 are configured to releasably engage the bone anchor assembly 2 such, as a housing 74 of a pedicle screw 2. The arm members 22 are moveable between a first position and a second position. When in the first "unlocked" position, the arm members 22 are not engaged with in the bone anchor assembly 2. In the second, "locked" position, the arm members 22 are engaged with the bone anchor assembly 2, and the bone anchor assembly 2 is "locked" to the guide assembly 12. In this example the guide assembly 12 has a castle nut 325 that acts as an actuator 330 to translate the arms from the unlocked position to the locked position and as a lock to prevent the arms 22 from moving out of the unlocked position prematurely. The castle nut 325 comprises a generally cylindrical body 53 having a proximal end 54, a distal end 56, and a lumen 58 extending therethrough. The exterior surface of the proximal end 54 includes a threaded region 60 configured to mate with the threaded region 52 of the outer sleeve 18. The interior surface of the lumen 58 at the distal end 56 includes a circumferential recess 62 configured to interact with the flanges 68 of the inner arm members 22. In this fashion, the castle nut 325 will direct translation of the arm members 22 along the outer sleeve 18 as the castle nut 325 is rotated against the threaded region 52 of the outer sleeve 18.

In the illustrated example, the castle nut 325 protrudes from the top of the outer sleeve 18. The castle nut 325 serves as a visual indicator of whether the guide assembly 12 is locked to the bone anchor assembly 2. More specifically, when the inner arm members 22 are in the first, "unlocked" position, the castle nut 325 protrudes from the top of the outer sleeve 18. When the inner arm members 22 are in the second, "locked" position and engaged to a bone anchor assembly 2, the castle nut 325 is flush with the guide 12 and consequently not visible above the top of the outer sleeve 18.

The illustrated castle nut 325 not only locks the position of the inner arms 22 after the arms 22 move into position, but also acts as the actuator 330 to control the translation of the inner arms 22. To do this the inner arms 22 are attached directly to the castle nut 325. The proximal ends of the inner arms 22 include a groove that is dimensioned to engage a corresponding ridge in the interior of the castle nut 325. Alternatively, the proximal ends of the inner arms 24 may be provided with ridges that are received within corresponding grooves formed in the interior of the castle nut 325 (not shown). Any combination of grooves and ridges may be employed to mate the inner arms 22 with the castle nut 325. In any case, by way of example only, the inner arms 22 may be mated with the castle nut 325 via a ridge/groove interaction. A tool (not shown) may be attached to the castle nut 325 (for example via slot) to help rotate the nut 325 and lock or unlock the inner arms 22 and bone anchor assembly 2. The groove/ridge interaction between the castle nut 325 and the inner arms 22 ensure that the castle nut 325 is able to rotate freely relative to the inner arms 22 while still controlling translation. The guide assembly 12 may be provided with rod slots 34 that extend substantially the length of the outer sleeve 18.

The illustrated embodiment of the guide member 12 is configured to be secured to a pedicle screw 2 by way of the outer sleeve 18. The actuator 330 is then advanced in a distal direction, which causes the simultaneous distal advancement of the inner arms 22 of the guide assembly 12. The inner arms 22 are advanced such that each pair of prongs 70 are positioned on either side of the upstanding arms 78 of the housing 74 and the raised protrusions are seated within recesses on the housing 74. At this point the inner arms 22 are secured to the pedicle screw 2 and the housing 74 is prevented from rotation relative to the guide assembly 12. Upon coupling of the guide assembly 12 and the pedicle screw 2, the opposed rod slots 34 formed between the outer arms 38 of the outer sleeve 18 of the guide member align with the rod channel 80 of the housing 74 to define an enclosed guide channel that is dimensioned to allow passage of a fixation rod 6. Utilizing the guide channel to align the rod 6 with the housing rod channel 80 reduces the need for tedious manipulation of the housing 74 and/or rod 6 near the surgical target site, as well as the associated need to fully visualize the pedicle screw 2 and/or the housing 74 during rod insertion. Thus, the overall size of the incision required to implant a fixation construct using the described system is significantly reduced compared to open procedures. Once the rod 6 has been seated in the housing 74 and secured with a lock screw 365 (as described below), the guide member 12 may be removed from the operative corridor. To accomplish this, a proximal force is applied to the actuator 330, which will disengage the inner arms 22 from the housing 74. The outer sleeve 18 may be disengaged from the housing 74 by applying an appropriate amount of proximal force on the guide assembly 12. Once both the outer sleeve 18 and the inner arms 22 have been disengaged from the housing 74, the guide assembly 12 may be removed from the operative corridor.

The guide members 12 may have a feature for temporarily connecting the racks. A specific embodiment of such a feature is a side track 46 extending from the proximal end to near the distal end of the guide 12. The side tracks 46 are dimensioned to accept one or more engagement features 435 on the pivot rack 14, locking rack 16, or both. An alternative embodiment of the guide member 12 comprises a pair of side tracks 46 on opposite sides of the guide member 12, which allows the racks 14, 16 to be connected to either side of the guide members 12 (the pivot and locking rack 16 may be connected to the same track or to different tracks). The engagement features 435 have a broad portion and a narrower portion to allow them to be freely slid into the track while constrained from moving radially with regard to the guide member 12. In the example shown in FIG. 6, the side track 46 extends longitudinally between the pair of opposed longitudinal rod slots 34. The illustrated embodiment of the side track 46 has a generally planar indented surface 48 within the track 46, and two elongated lip elements 50 partially overhanging the indented surface (the track 46 could be configured to have one elongated lip element 50). In the illustrated embodiment the overhanging lip elements 50 extend the entire length of the track 46, but they could be interrupted so long as the interruption is not of sufficient size to allow the engagement feature 435 on the rack to depart from the track. As shown in the illustrated embodiment, the track 46 may contain one or more rack engagement features 440 that work in combination with complementary engagement features 435 on the rack to secure the two components to one another.

For example, the rack engagement feature 440 may be a shim restraining feature 445, configured to interact with a shim 440 to temporarily restrain the shim 440 from sliding in the side track 46. Such a feature works in cooperation with a shim 440 on the pivot rack 14 to restrain the shim 440 once it is properly seated in the side track 46. As explained below, the shim 440 may include additional features to facilitate reversible restraint in the track 46. Multiple such features may be present in the side track 46 as needed.

Figure 6:
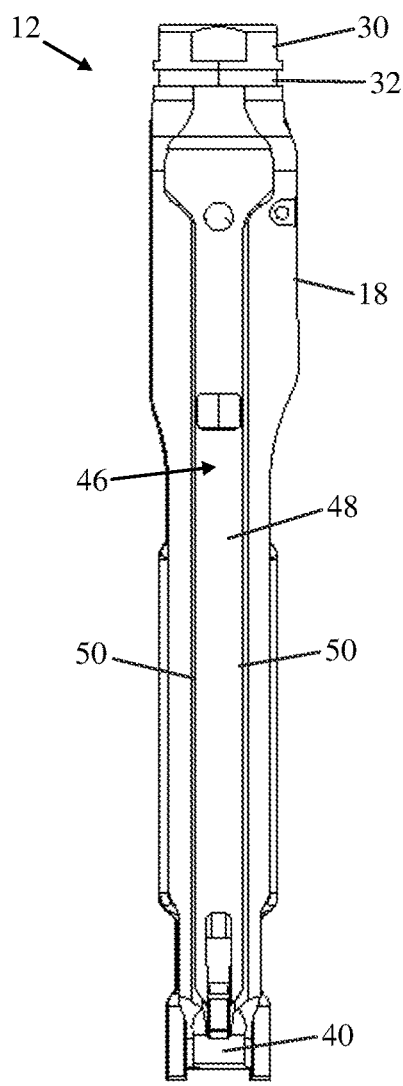
FIG. 6. A plan view of the example guide assembly of FIG. 5.
Figure 7:
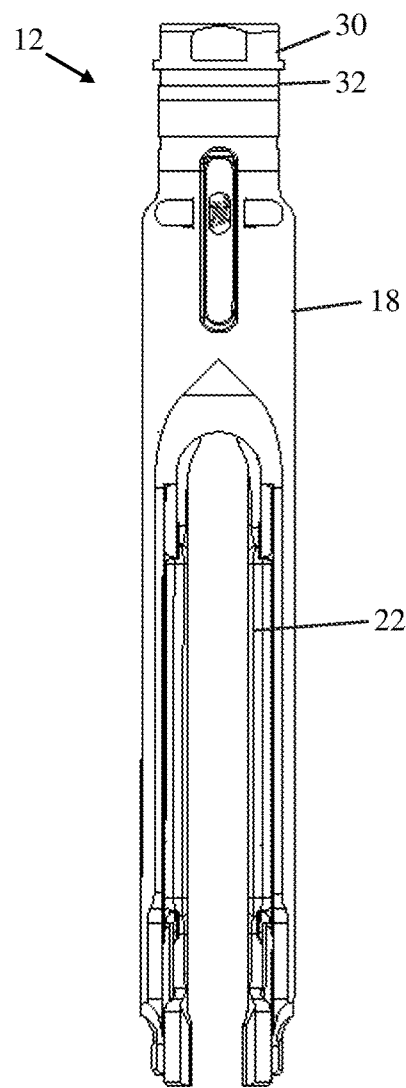
FIG. 7. Another plan view of the guide assembly of FIG. 5.
Figure 8:
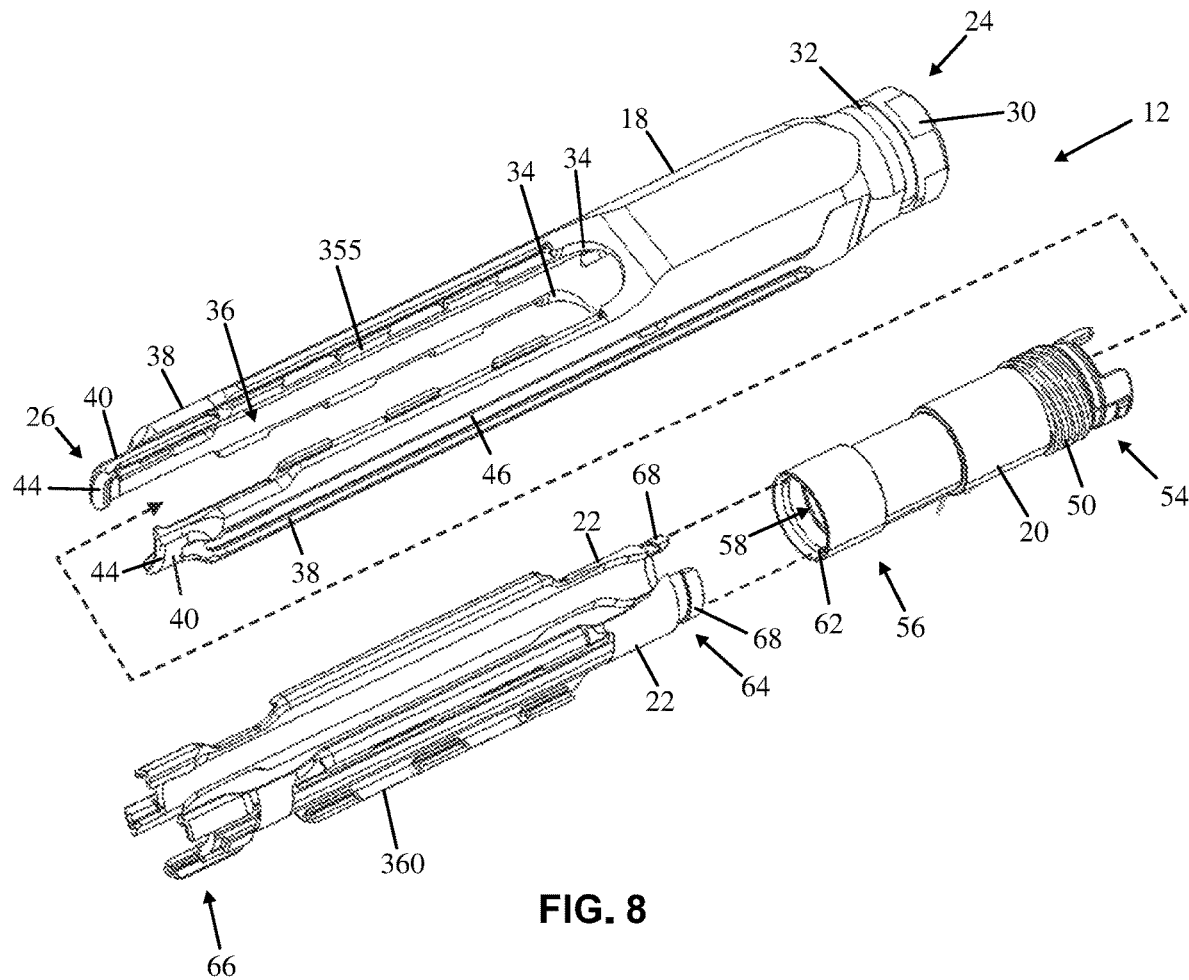
FIG. 8. An exploded perspective view of the guide assembly of FIG. 5.
Figure 9:
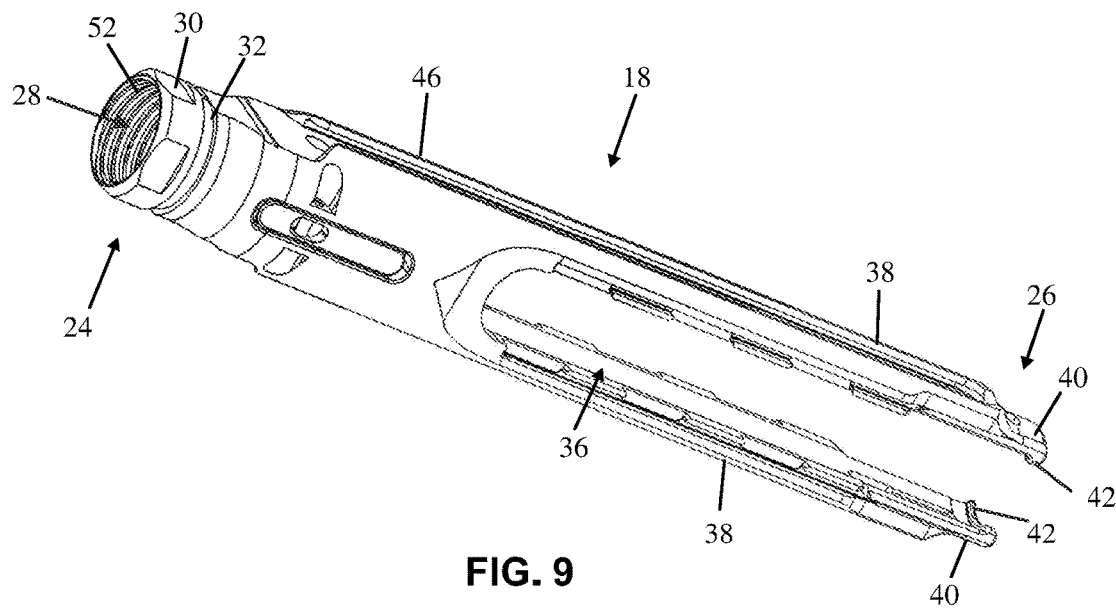
FIG. 9. A perspective view of an outer sleeve forming part of the guide assembly of FIG. 5.
Figure 13:
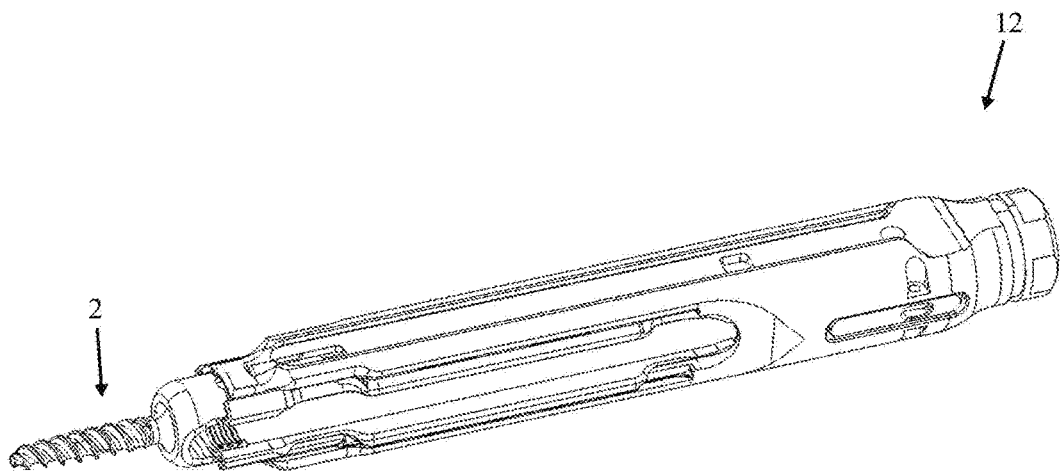
FIG. 13. A perspective view of the guide assembly of FIG. 5 coupled to the bone anchor of FIG. 11.

As shown in FIG. 6, the track contains a plurality of recesses or apertures 320 that work in conjunction with complementary features on the racks to secure them. The recesses or apertures 320 as shown are positioned in the generally planar indented surface and pass through to the lumen 58. Such features could be positioned elsewhere on the guide, or could take the form of an indentation in the track 48 instead of an aperture to the lumen 58.

The guide members 12 may be marked to allow visual confirmation by the user that the guide has been properly attached to one or both of the racks. The illustrated embodiments in FIG. 5 has a locking rack indicator pattern 335 (line) inscribed at the proximal end of the side track 46. The locking rack indicator line 335 is positioned so that it is covered by the arm element 105 of the locking rack 16 if the arm element 105 is in the side track 46, but incompletely reduced in the distal direction for secure locking. The guide members 12 may also be marked to allow visual confirmation by the user that the distal attachment element 178 of the pivot rack arm has been properly seated in the side track 46. A pivot rack indicator pattern 375 may be positioned on the guide member 12 to be visible (or alternatively to only be obscured from view) when the distal attachment element 178 is fully seated in the side track 46. The exact position of the indicator patterns 335 will depend on the shape and dimensions of the side track 46 and the arm element 105 or distal attachment element 178. Ideally it will be conspicuous, having contrasting color, shape, or texture with the rest of the guide member 12.

The guide members 12 may also be marked with a pattern to indicate when the arm element 105 of the locking rack 16 is properly aligned to be slid into the side track 46. In the illustrated embodiment shown in FIG. 6, the alignment indicator pattern 335 is a pair of triangles on either side of the side track 46. When matched with indicator patterns 335 inscribed on the arm elements 105, the arm elements 105 may be slid into the tracks.

Figure 44:
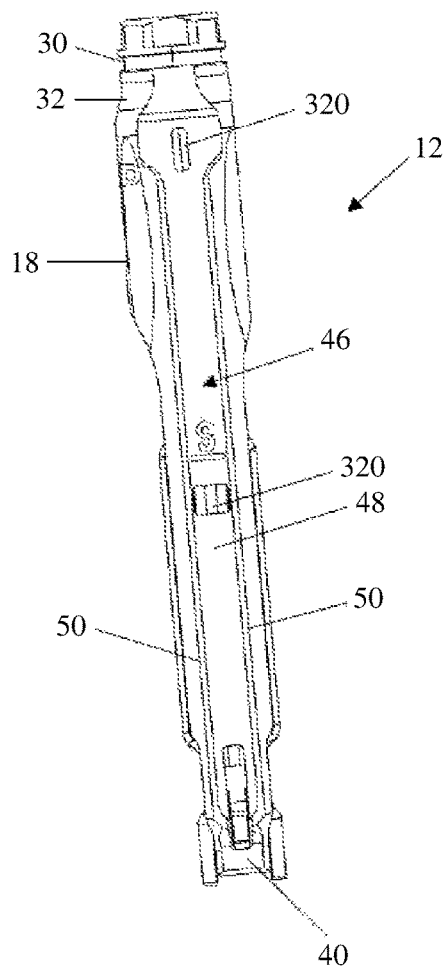
FIG. 44. A side plan view of an alternative embodiment of the guide member.
Figure 45:
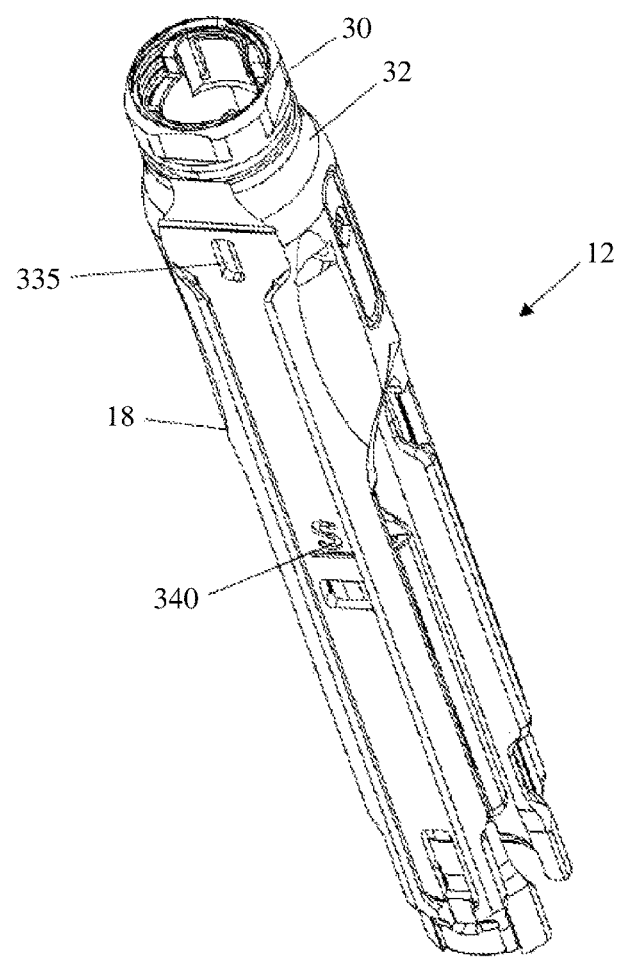
FIG. 45. A perspective view of the embodiment of the guide member shown in FIG. 44.

An incision depth indicator 340 pattern may also be present on the guide 12, as shown in FIGS. 44-45. In the illustrated embodiment of the guide 12 in FIGS. 44-45, the incision depth indicator pattern 340 is a line inscribed in the side track 46 and marked with an "S". In the illustrated embodiment, if the incision depth indicator 340 is below the skin of the patient when the guide 12 is in place, then a larger size of pivot rack arm unit must be used; and if the incision depth indicator 340 is above the skin of the patient, a smaller size of pivot rack arm unit may be used.

The features of the guide members 12 that serve to connect them to the racks and the bone anchor assemblies 2, 4 must be capable of withstanding torque that is typical of spinal distraction, compression, and angulation. Materials and structural configurations to achieve such torque resistance may be any known in the art. Furthermore, such materials must be suitable for sterilization by at least one method (e.g., steam, dry heat, irradiation, ethylene oxide, ethylene bromide, etc.). Any such materials known in the art may be used, such as titanium, alloys of titanium, stainless steel, and surgical stainless steel.

As suggested above, the bone anchor assembly 2 may comprise an anchor 72 (such as a threaded shank) suitable for stable fixation to vertebral bone and a housing 74 for capturing and locking a spinal rod 6 (as shown in FIGS. 11-12). The housing 74 may have a base 76 that mates with the bone anchor 72 and a pair of upstanding arms 78 separated by a rod channel 80. The arms 78 may be equipped with a locking cap guide 81 and advancement feature 82, such as by way of example, a helically wound flange feature disposed on the interior face of each arm 78. In such embodiments the locking cap guide 81 and advancement feature 82 mates with a complementary guide and advancement feature on a lock screw 365. The lock screw 365 may engage the upstanding arms 78 via the complementary guide and advancement features to press and lock the fixation rod 6 into the housing 74. The housing 74 and anchor 72 may be mated with a polyaxial engagement such that the housing 74 can pivot relative to the anchor 72 in any direction. The engagement may also be such that the pivoting movement may be inhibited in one or more directions. By way of example, the housing 74 and anchor 72 may be mated with a uniplanar engagement such that the housing 74 pivots relative to the anchor 72 in a single plane. The housing 74 and anchor 72 may also be fixed such that no movement is possible between the housing 74 and anchor 72. The angle of the housing 74 may also be initially adjustable, but lockable prior to final capture of a rod 6 in the housing 74 (e.g. a provisional locking screw). The screw 365 may also include a fixed or adjustable head arrangement with an additional adjusting rod seat (e.g. pivotable, rotatable, translatable). The screw 365 may be further configured to facilitate the application of cement or adhesive material into the pedicle screw 2 to increase the purchase strength of the anchor 72.

Figure 65:
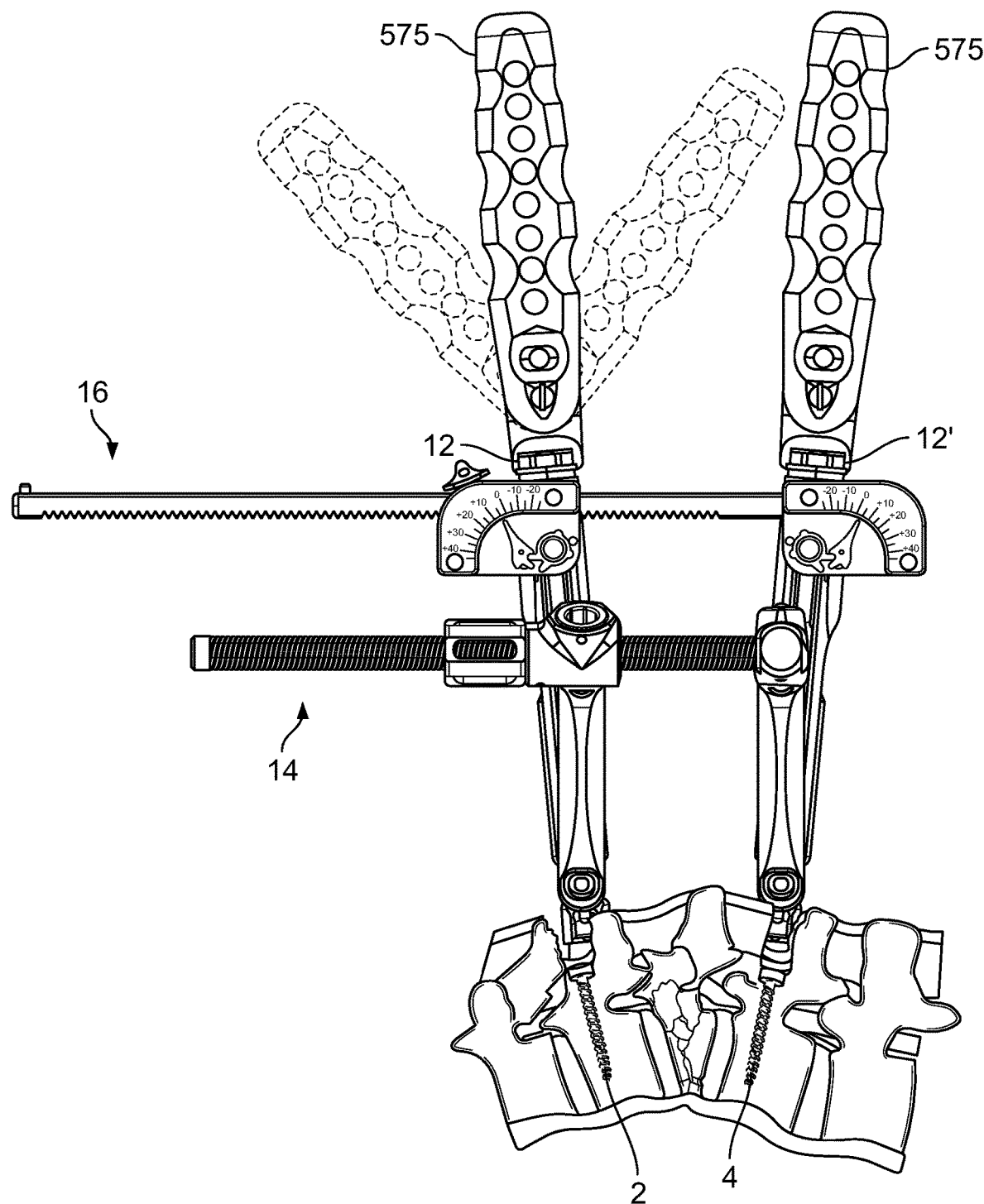
FIG. 65. An illustration of the embodiment of the system shown in FIGS. 60-64, showing embodiments of the dual driver and leverage instrument in place in the lumens of the first and second guide members. The ghost images show the range of rotation of the handle relative to the shaft.

Instruments may be used to assist with the manual angulation of the guide members 12, 12'. Such an instrument may function simply as a lever, by extending the length of the guide member 12 when it is inserted into the lumen. An example of one such instrument is shown in FIGS. 64-74. The exemplary instrument is a dual driver and leverage instrument 455. The instrument 455 functions as a lever when inserted into the lumen 28 of the guide members 12, and functions as a driver for the locking pin on the pivot rack 14. The exemplary embodiment comprises a handle 460; a shaft 465 affixed to the handle; and a driving engagement feature 470 affixed to the shaft 465 at an end opposite the handle 460. The shaft fits 465 within a lumen 28 of the guide member 12, and wherein the driving engagement feature 470 is configured to drive a locking pin 475 on the pivot rack 14. As depicted in FIG. 65, some embodiments of the dual driver and leverage instrument 455 are capable of angulating the handle 460 relative to the shaft 465 for greater leverage. In that embodiment the handle 460 can either be locked in place or allowed to rotate relative to the shaft 465 about an axis near the interface between the handle 460 and shaft 465.

The pivot rack 14 is configured to be connected to the first and second guide members 12, 12'. The pivot rack 14 provides a pivot point about which the distal ends of the guides 12, 12' will rotate when the proximal ends of the guides are manipulated to converge or diverge from one another. By way of example, the pivot rack 14 is configured to position the pivot points adjacent the distal end of the guides 12, 12' near the guide/screw interface. In effect this positions the pivot point close to the vertebrae such that rotation of the guides 12, 12' causes rotation of the vertebrae with minimal effect on the distance between the vertebrae. In other words, distal coupling points of the pivot rack 14 allow the first and second guide members 12, 12' to rotate relative to one another about axes at the distal ends of the first and second guide members 12, 12', which in turn allows the bone anchor assemblies 2, 4 to be angulated with only limited compression or distraction of the spine. Some embodiments of the pivot rack 14 comprise a pivot rack locking mechanism 480 to prevent the first and second guide members 12, 12' from translating toward or away from one another, granting further control of the positioning of the bone anchor assemblies 2, 4 during correction. The pivot axis will be generally perpendicular to the direction of the spinal rod 6 and generally perpendicular to the longitudinal axis of the guide member 12 when the system is assembled.

Figure 14:
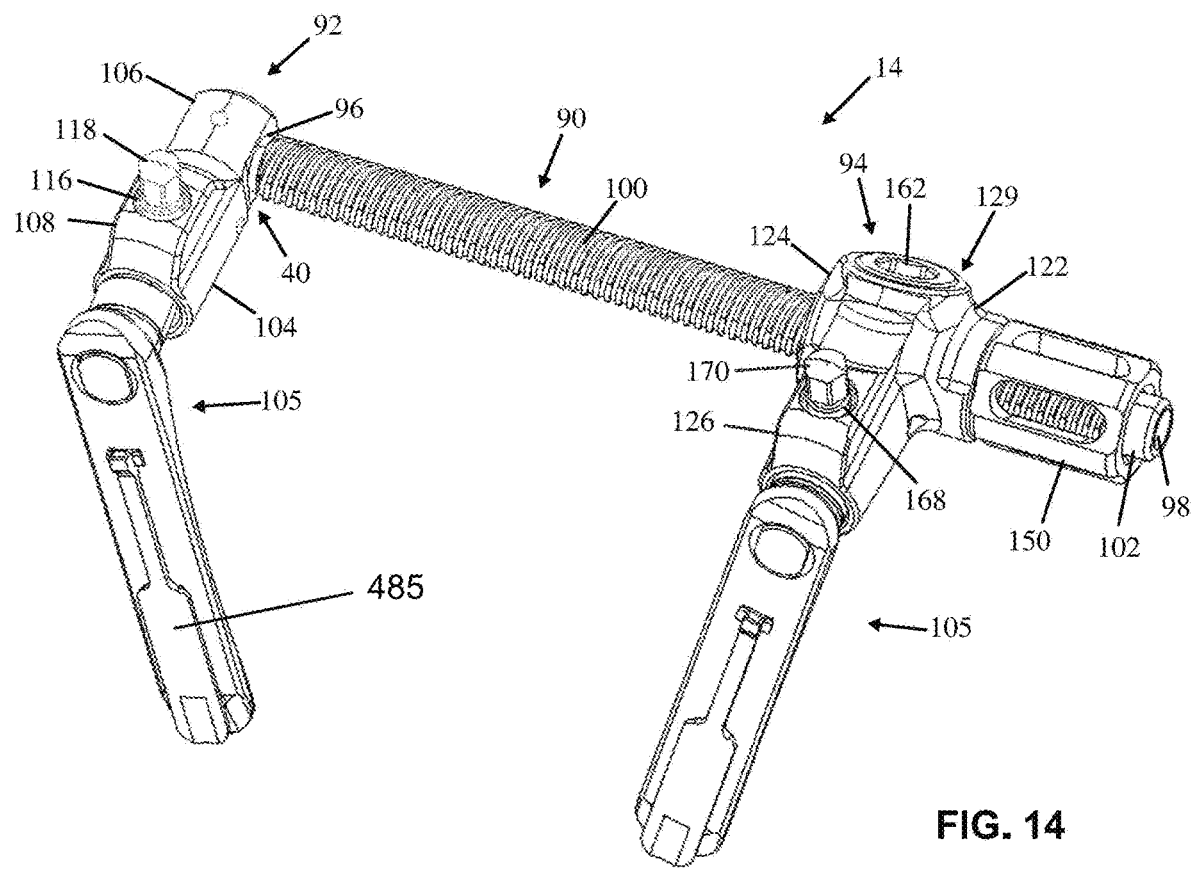
FIG. 14. A perspective view of an example of a pivot rack assembly forming part of the spinal fixation/correction system of FIG. 1.
Figure 15:
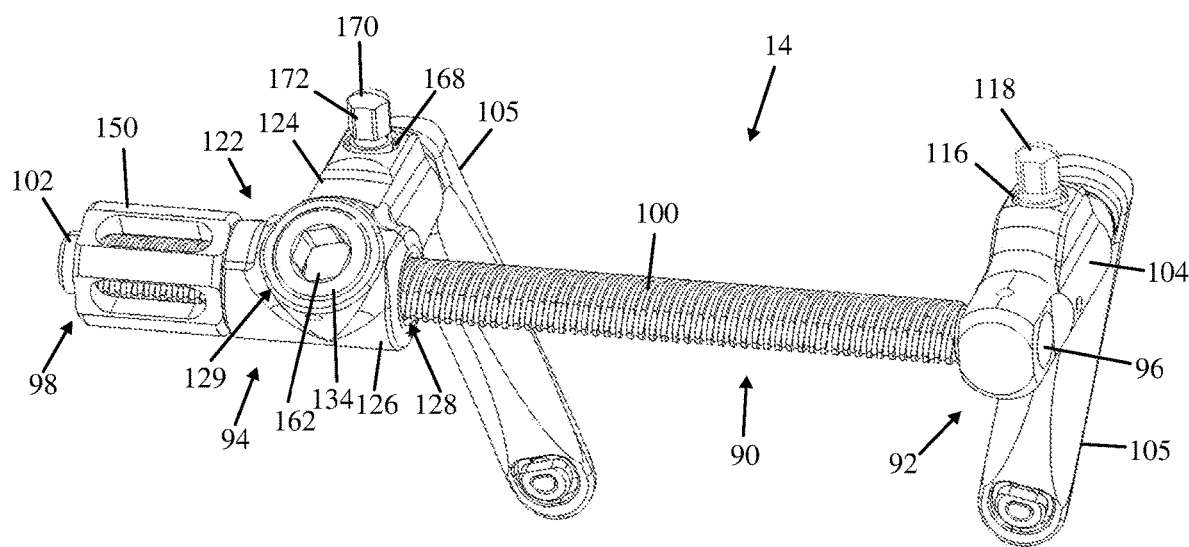
FIG. 15. Another perspective view of the pivot rack assembly of FIG. 14.
Figure 16:
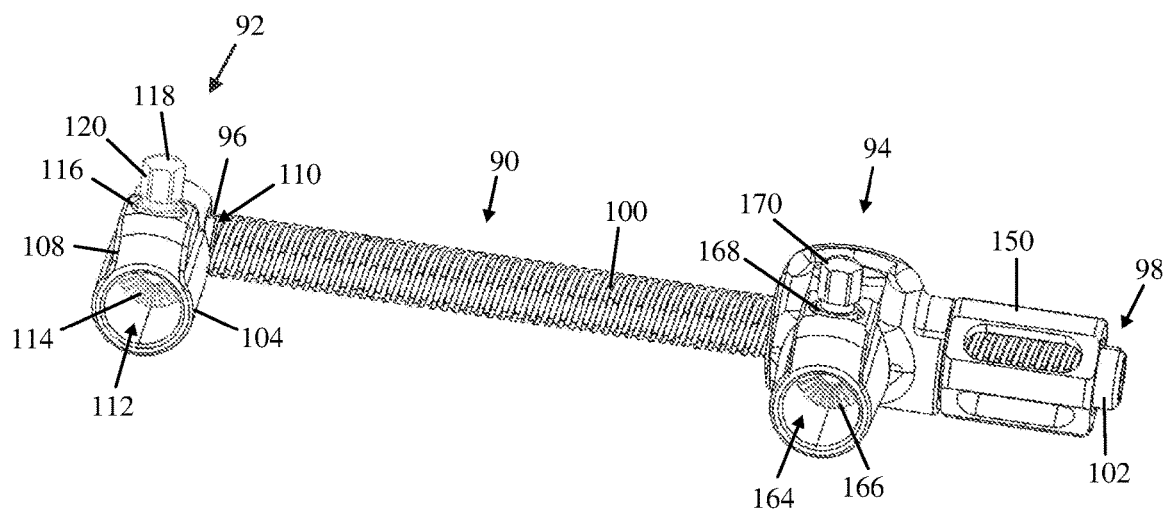
FIG. 16. A perspective view of the pivot rack assembly of FIG. 14 with the arm units removed.
Figure 17:
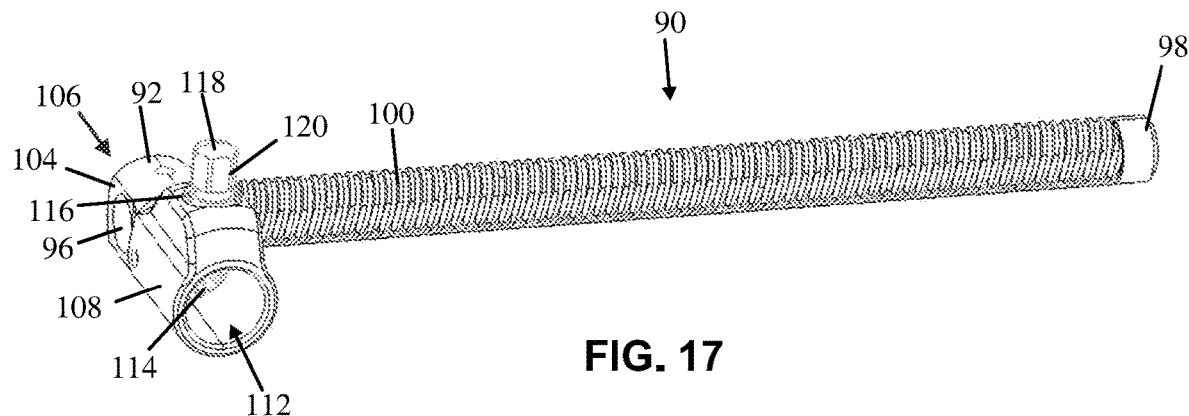
FIG. 17. A perspective view of a rack member forming part of the pivot rack assembly of FIG. 14.
Figure 18:
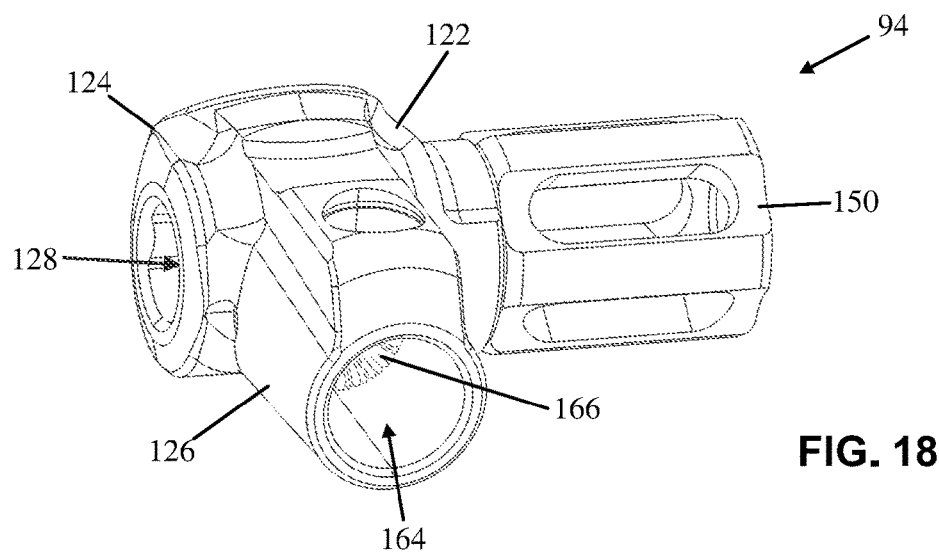
FIG. 18. A perspective view of a translation assembly forming part of the pivot rack assembly of FIG. 14.

An exemplary embodiment of the pivot rack 14 is shown in FIGS. 14-16. This exemplary embodiment is further described in detail, by way of example only. The rack 14 has two arms units 105 (first and second arm units) that serve to connect the rack 14 to the guide members 12, 12'. Each arm unit 105 is fixedly connected to one of two arm assemblies 92, 94, which are in turn connected to an elongate rack member 90. At least one of the arm assemblies 92, 94 is capable of translating relative to the elongate rack member 90. The other may be fixed, or may also be capable of translating.

The arm units 105 may include attachment features at either end, such as a bone anchor guide member attachment feature 485 at the first end and an arm assembly attachment feature 490 at the second end. A specific embodiment of the arm unit 105 includes a guide member attachment feature 485 with a narrow proximal portion and a wide distal portion that comprises a post 200 that extends through a distal aperture 186 in the arm unit 105, as further described below. The arm assembly attachment feature is received by one of the arm assemblies 92, 94, which has a complementary arm unit engagement feature capable of reversibly locking the rotation of the arm units 105 relative to the arm assemblies 92, 94. This permits the arms to be adjusted as necessary to install them on the guide members 12, 12', then locked into place to maintain the positions of the guide members 12, 12' during the correction procedure. Some embodiments of the pivot arm assemblies 92, 94 limit the extent to which the arm units 105 can be rotated prior to locking. The maximum degree of rotation will be sufficient to accommodate the expected relative angles of the guide members 12. Some embodiments of the pivot arm assembles 92, 94 are configured to allow the arm unit 105 to rotate 45.degree. in either direction (total arc of 90.degree.). Further embodiments of the pivot arm assembles 92, 94 are configured to allow the arm unit 105 to rotate 30.degree. in either direction (total arc of) 60.degree. Additional embodiments of the pivot arm assemblies 92, 94 are configured to allow the arm unit 105 to rotate 25, 20, 15, or 10.degree. in either direction.

FIGS. 14-16 illustrate an example of a pivot rack 14 forming part of the spinal trauma correction system 10 disclosed herein. The following paragraphs describe this embodiment in detail by way of example only. The pivot rack 14 engages with the guide towers 495 and functions to lower the pivot point of the guide towers 495. As shown, the pivot rack 14 includes an elongated rack member 90, a first arm assembly 92 and a second arm assembly 94. This version of the elongated rack member 90 is generally cylindrical and has a first end 96, a second end 98, and a thread 100 extending between the first and second ends 96, 98. The first end 96 is fixedly attached to the first arm assembly 92. The second end 98 includes a cap 102 that prevents translation of the second arm assembly 94 beyond the end of the rack member 90. The thread 100 may be a single lead thread, or it may include two or more leads.

Figure 46:
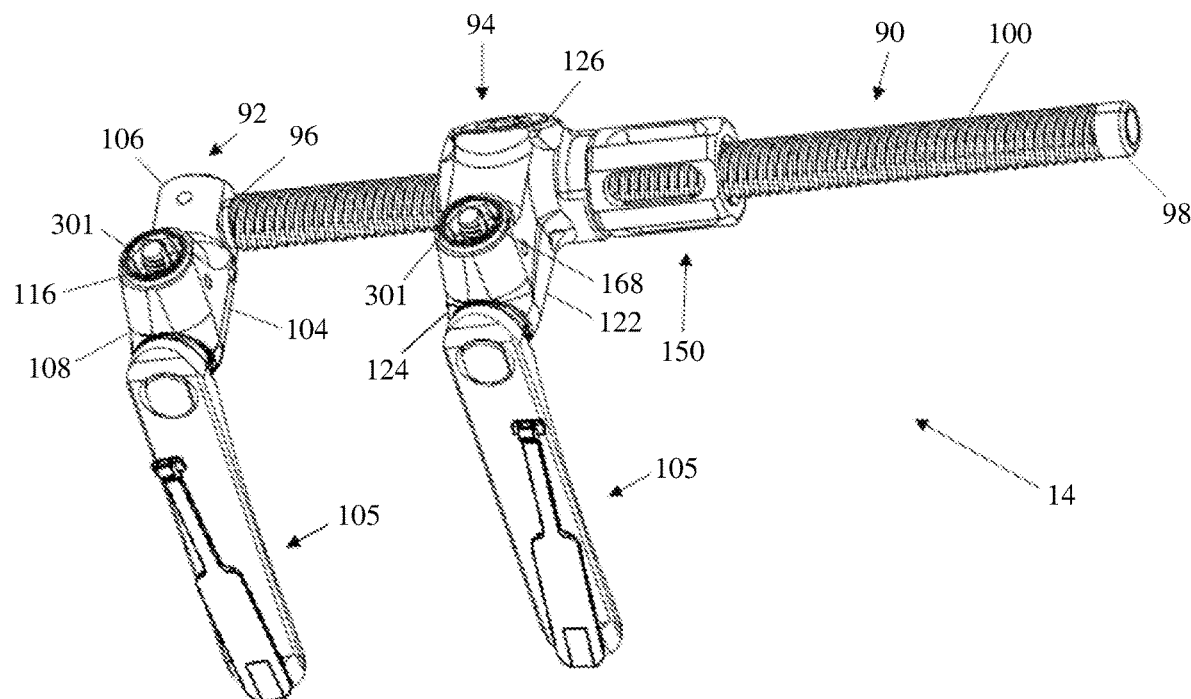
FIG. 46. A rear perspective view of an alternative embodiment of the pivot rack.
Figure 47:
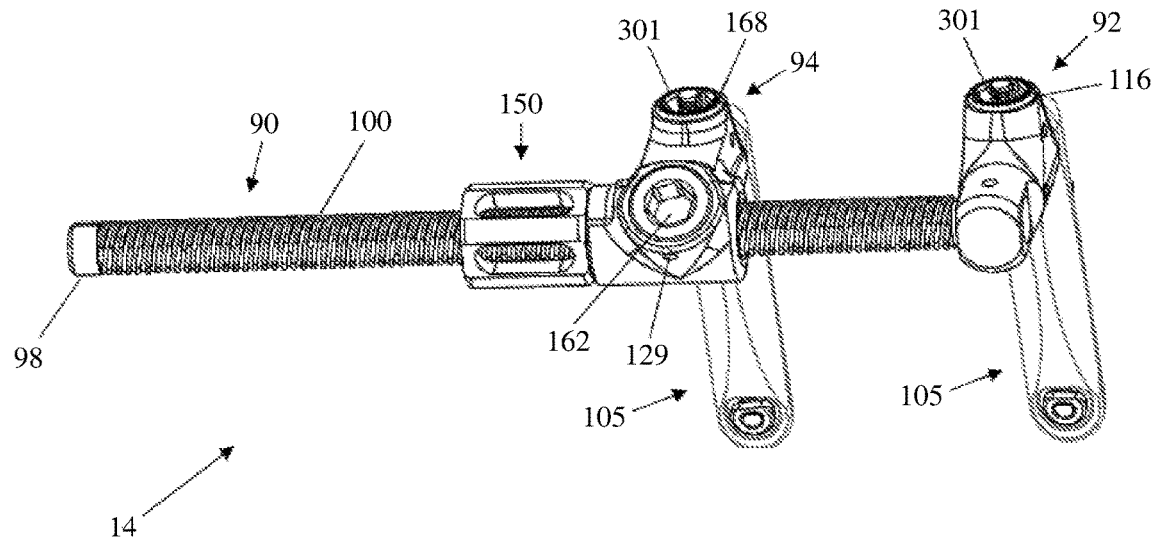
FIG. 47. A front perspective view of the embodiment of the pivot rack shown in FIG. 46.
Figure 48:
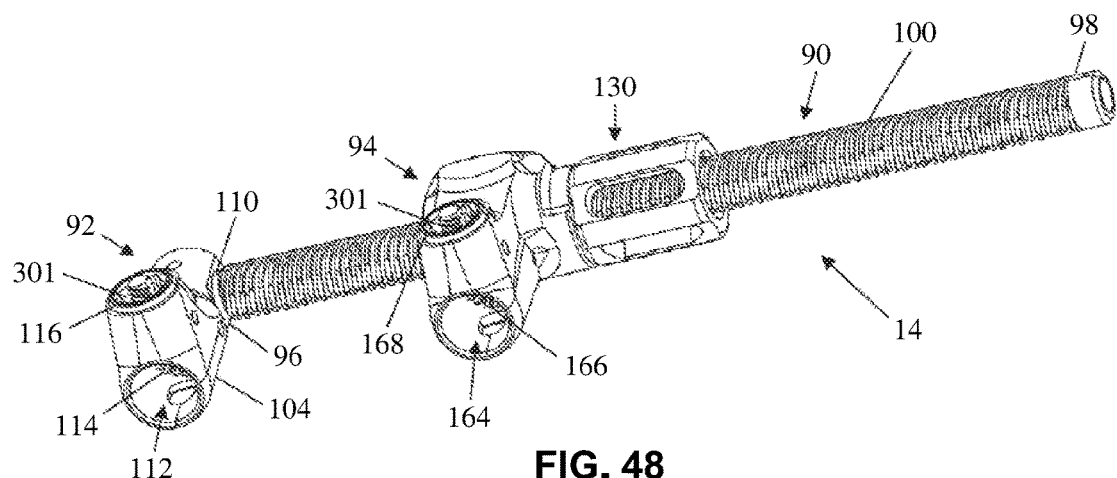
FIG. 48. A front perspective view of the embodiment of the pivot rack shown in FIG. 46 isolated from the arm units.
Figure 49:
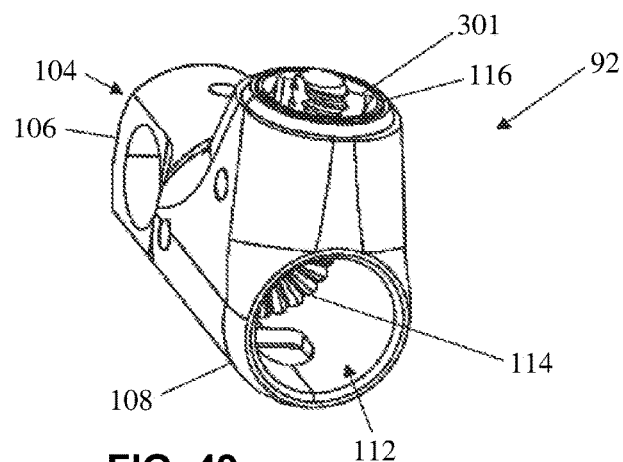
FIG. 49. A perspective view of the first arm assembly in the embodiment of the pivot rack shown in FIG. 46.
Figure 50:
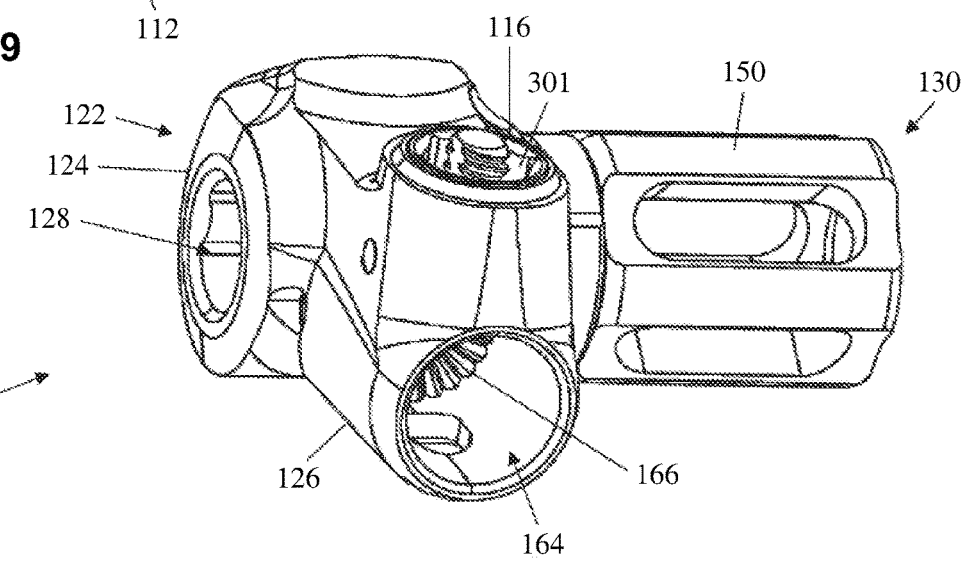
FIG. 50. A perspective view of the second arm assembly in the embodiment of the pivot rack shown in FIG. 46.
Figure 51:
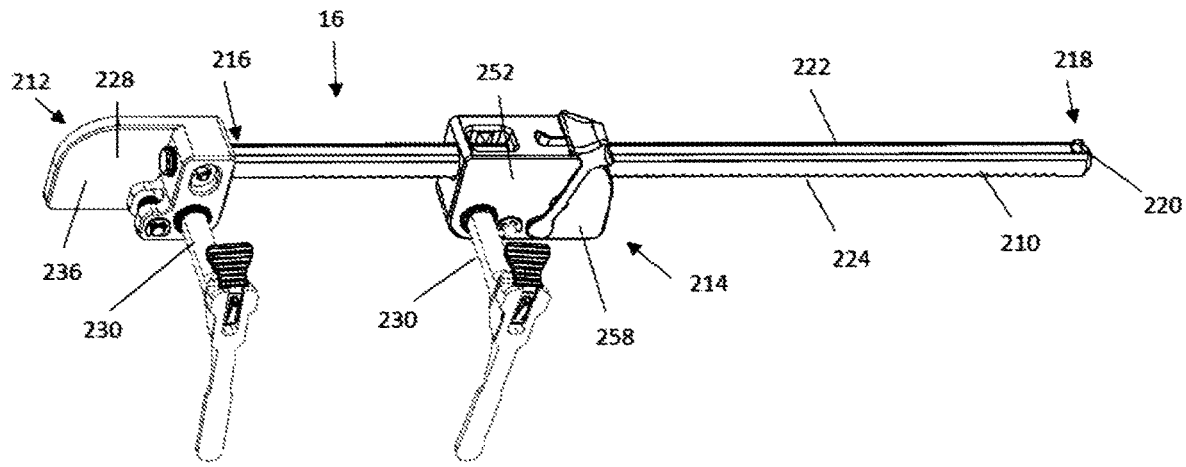
FIG. 51. A rear perspective view of an alternative embodiment of the locking rack.
Figure 52:
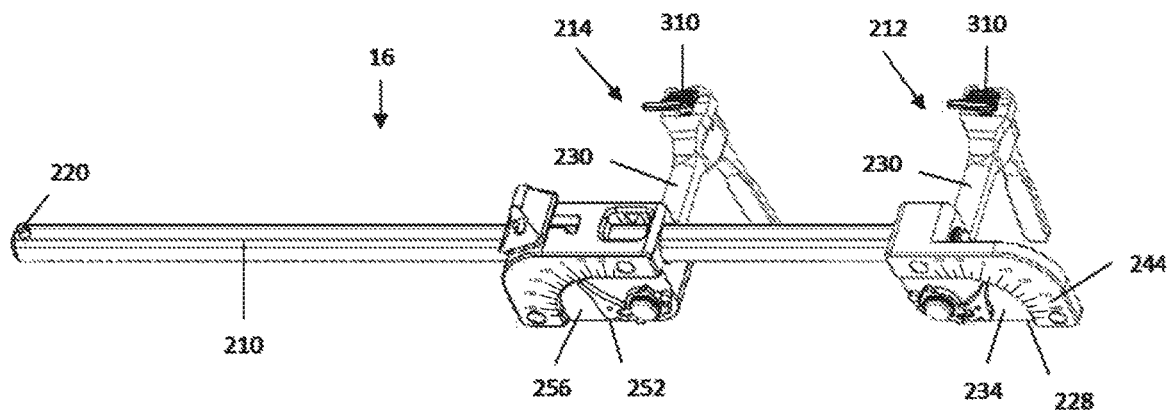
FIG. 52. A front perspective view of the embodiment of the locking rack shown in FIG. 51.

In the illustrated embodiment, the first arm assembly 92 is fixedly attached to the first end 96 of the elongated rack member 90 and includes a housing 104 and an arm unit 105. The housing 104 has a proximal portion 106 and a distal portion 108. The proximal portion 106 includes a lateral recess 110 sized and dimensioned to receive the first end 96 of the elongated rack member 90 therein. The distal portion 108 includes a distal cavity 112 sized and configured to receive the proximal attachment element 176 of the arm unit 105 (described in detail below with reference to FIGS. 20-22). The distal cavity 112 is generally cylindrical in shape to allow rotation of the proximal attachment element 176 of the arm unit 105 if necessary prior to locking it in position. The distal cavity 112 further includes a generally circular ridged engagement feature 114 configured to engage with a corresponding proximal engagement feature 190 of the proximal attachment element 176 of the arm unit 105. The distal portion 108 further includes a threaded aperture 116 extending through the distal portion 108 and into the distal cavity 112. A locking pin 118 is threadedly engaged within the threaded aperture 116 and includes a proximal engagement feature 120 for engaging a locking tool and a distal post element (not shown). The proximal engagement feature 120 may take various forms, such as a hex head feature as shown in FIGS. 14-17, and hexagonal socket 301 as shown in FIGS. 46-48. When the locking pin 118 is manipulated (e.g., turned in a clockwise direction), the post 200 is advanced into the distal cavity 112 and into a locking engagement with the lock recess 192 of the proximal attachment element 176 of the arm unit 105. This locks the arm unit 105 to the first arm assembly 92.

Figure 19:
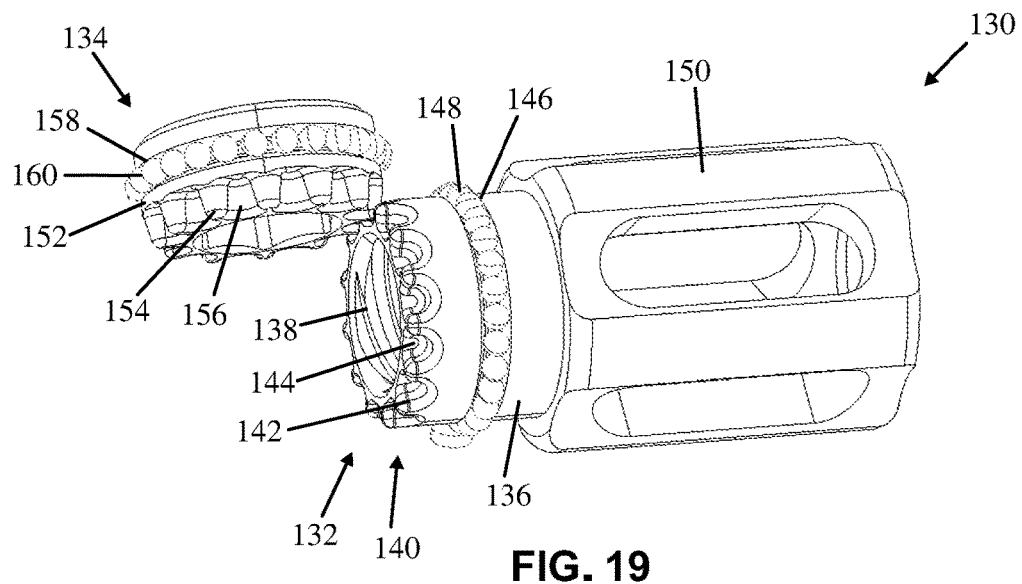
FIG. 19. A perspective view of the translation assembly of FIG. 18 with the housing removed.

The second arm assembly 94 in the illustrated embodiment includes a housing 122 and an arm unit 105. The housing 122 has a proximal portion 124 and a distal portion 126. The proximal portion 124 includes a lateral lumen 128 sized and dimensioned to receive the elongated rack member 90 therethrough and a circular aperture 129 configured to receive at least a portion of the second gear member 134 described below. The lateral lumen 128 also houses the translation unit 130 (FIG. 19). This embodiment of the translation unit 130 comprises a first translation control structure 500 comprising a handle 505 to be manually gripped and a second translation control structure 510 comprising a driver engagement feature 520 to receive torque applied by a driver instrument. The translation unit 130 includes a first gear member 132 and a second gear member 134. The first gear member 132 is positioned directly on the elongated rack member 90 and includes a generally cylindrical body portion 136 having threaded lumen 138 extending longitudinally therethrough that mates with the thread 100 in such a way that the first gear member 132 may rotate (clockwise or counterclockwise) about the elongated rack member 90 and in so doing also migrates laterally along the elongated rack member 90. For example, clockwise rotation of the first gear member 132 causes the first gear member 132 (and by extension the second arm assembly 94) to migrate along the elongated rack member 90 toward the first arm assembly 92. Counterclockwise rotation of the first gear member 132 cause the first gear member 132 (and by extension the second arm assembly 94) to migrate along the elongated rack member 90 away from the first arm assembly 92.

As shown in the embodiment in FIG. 19, the body portion 136 of the first gear member 132 includes a geared edge 140 having a plurality of teeth 142 and recesses 144 arranged evenly about the circumference of the geared edge 140. The body portion 136 further includes a circumferential recess 146 that partially houses a bearing 148 that secures the position of the first gear member 132 relative to the housing 122 (the remainder of the bearing 148 is housed in a complementary recess formed within the lateral lumen 128 (not shown)), and a thumbwheel 150 positioned opposite the geared edge 140. Unlike the body portion 136 that is positioned within the lateral lumen 128, the thumbwheel 150 is positioned outside the lateral lumen 128 so that it may be manually manipulated by a user. The thumbwheel 150 enables a user to manually turn the first gear member 132 and effect migration of the second arm assembly 94.

In the illustrated embodiment, the second gear member 134 has a distal geared edge 152 having a plurality of teeth 154 and recesses 156 arranged evenly about the circumference of the distal geared edge 152. The distal geared edge 152 of the second gear member 134 mates with the geared edge 140 of the first gear member 132 (e.g. with the teeth 154 of the second gear member 134 being received within the recesses 144 of the first gear member 132, and the teeth 142 of the first gear member 132 being received within the recesses 156 of the second gear member 134), enabling rotation of the second gear member 134 to effect rotation of the first gear member 132. The second gear member 134 further includes a circumferential recess 158 that partially houses a bearing 160 that secures the position of the second gear member 134 relative to the housing 122 (the remainder of the bearing 160 is housed in a complementary recess (not shown) formed within the circular aperture 129). The second gear member 134 further has an outer-facing surface that includes a driver engagement feature 162 (e.g., a hex engagement feature) for receiving an instrument capable of applying sufficient torque to the second gear member 134 to cause the first gear member 132 to turn (and the second arm assembly 94 to migrate) after the pivot rack 14 has been locked in place, for example to effect compression or distraction on a surgical target site.

Figure 20:
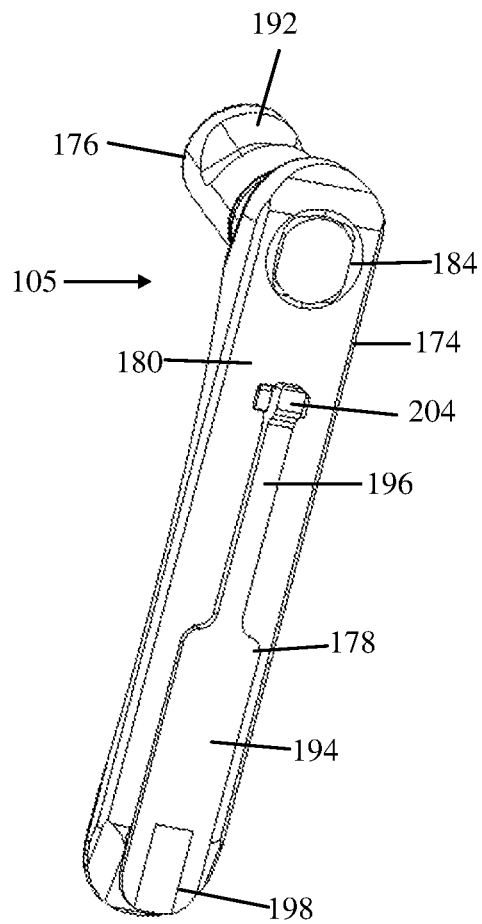
FIG. 20. A front perspective of an arm unit forming part of the example pivot rack assembly of FIG. 14.
Figure 21:
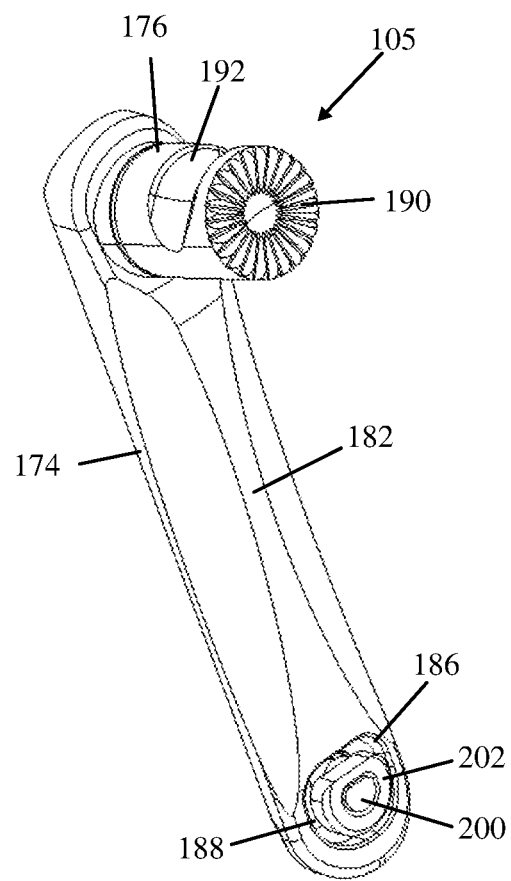
FIG. 21. A rear perspective view of an arm unit forming part of the example pivot rack assembly of FIG. 14.
Figure 22:
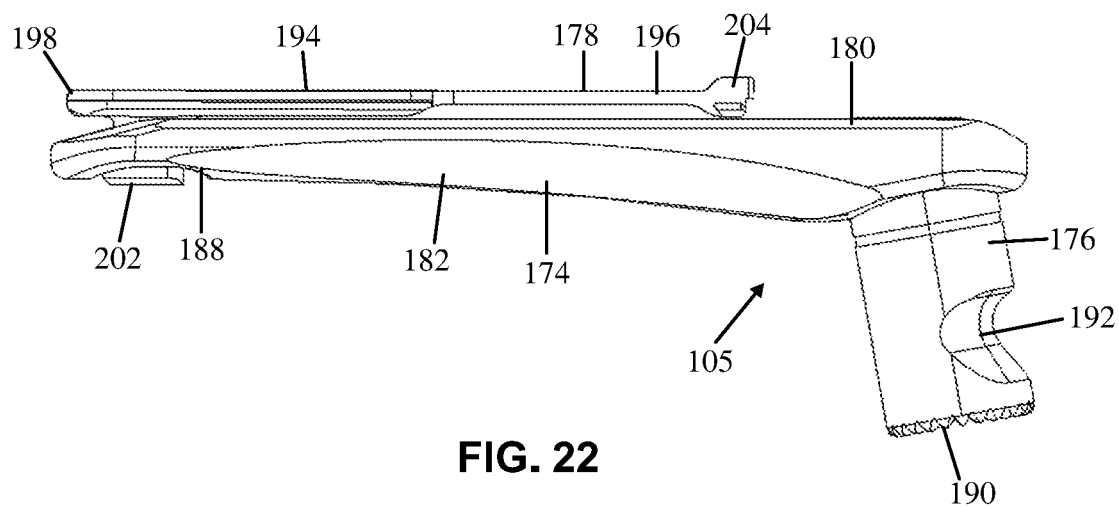
FIG. 22. A side plan view of an arm unit forming part of the example pivot rack assembly of FIG. 14.
Figure 23:
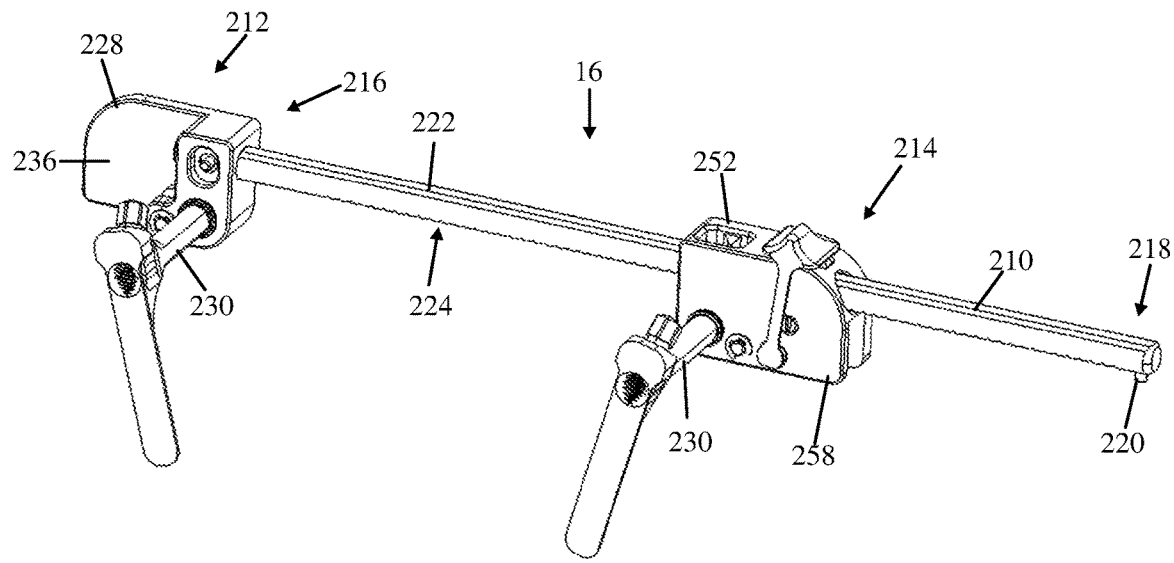
FIG. 23. A rear perspective view of a locking rack assembly forming part of the example spinal fixation/correction system of FIG. 1.
Figure 24:
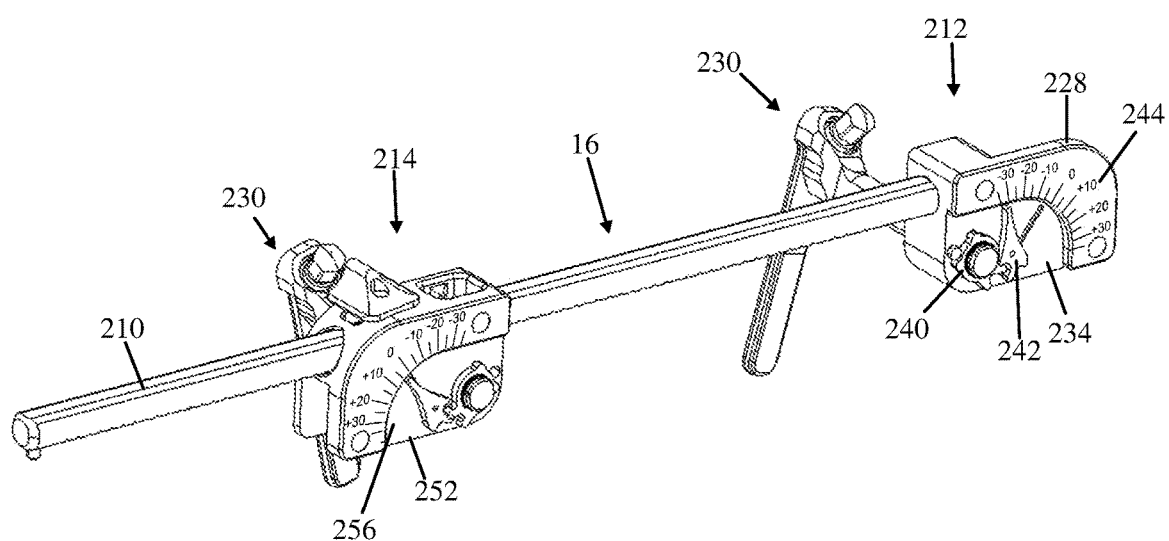
FIG. 24. A front perspective view of a locking rack assembly forming part of the example spinal fixation/correction system of FIG. 1.
Figure 28:
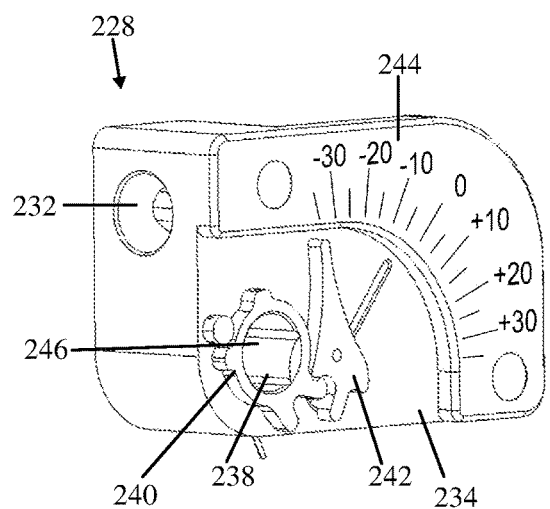
FIG. 28. Perspective view of a first calibration assembly forming part of the example locking rack assembly of FIG. 23.
Figure 29:
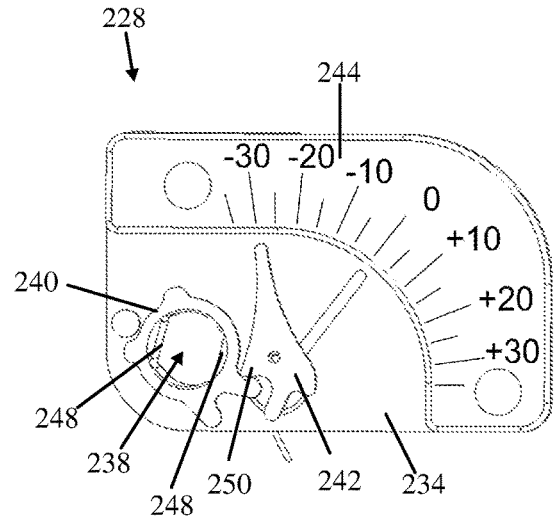
FIG. 29. Plan view of a first calibration assembly forming part of the example locking rack assembly of FIG. 23.
Figure 30:
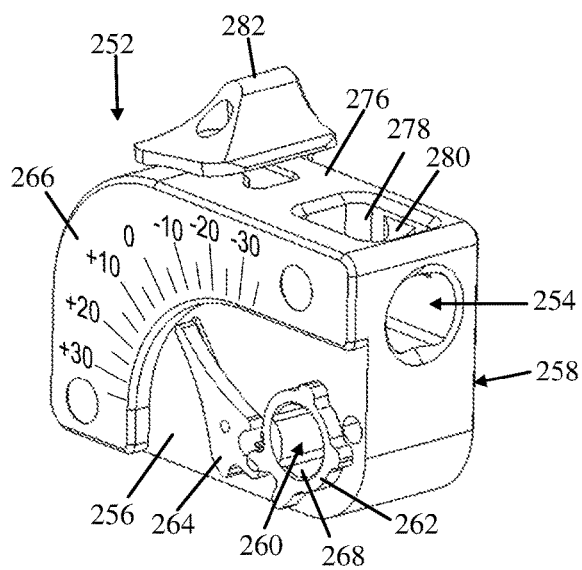
FIG. 30. Perspective view of a second calibration assembly forming part of the example locking rack assembly of FIG. 23.
Figure 31:
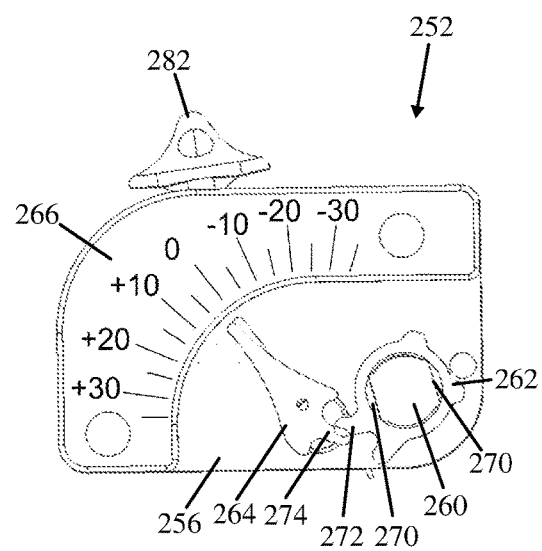
FIG. 31. Plan view of a second calibration assembly forming part of the example locking rack assembly of FIG. 23.

In the illustrated embodiment, the distal portion 126 of the second arm assembly 94 includes a distal cavity 164 sized and configured to receive the proximal attachment element 176 of the arm unit 105 (described in detail below with reference to FIGS. 20-22). The distal cavity 164 is generally cylindrical in shape to allow rotation of the proximal attachment element 176 of the arm unit 105 if necessary prior to locking it in position. The distal cavity 164 further includes a generally circular ridged engagement feature 166 ("poker chip") configured to be engaged with a corresponding proximal engagement feature 190 ("poker chip") of the proximal attachment element 19 of the arm unit 105. The distal portion 126 further includes a threaded aperture 168 extending through the distal portion 126 and into the distal cavity 164. A locking pin 170 is threadedly engaged within the threaded aperture 168 and includes a proximal engagement feature 172 (e.g., a hexagonal socket 301) for engaging a locking tool and a distal post element (not shown). When the locking pin 170 is manipulated (e.g. turned in a clockwise direction), the post is advanced into the distal cavity 164 and into a locking engagement with the lock recess 192 of the attachment element 176 of the arm unit 105. This locks the arm unit 105 to the second arm assembly 94.

In the illustrated embodiment, the arm unit 105 (which may be either of the first and second arm assemblies 92, 94) includes an arm element 174, a proximal attachment element 176, and a distal attachment element 178. The arm element 174 is a rigid, elongated member that functions to lower the pivot point of the guide towers 12 to a point just above the pedicle screws 2, 4. The arm element 174 further includes a first front side 180, a backside 182, a proximal aperture 184, a distal aperture 186, and a distal recess 188. By way of example only, the front side 180 is configured to face the guide tower 12, and therefore may have a generally smooth, flat surface. The back side 182 is configured to be tissue-facing during use, and therefore has a contoured surface to minimize unnecessary trauma to the surrounding tissue during use.

In the illustrated embodiment, the proximal attachment element 176 comprises a generally cylindrical base member having a ridged proximal engagement feature 190 ("poker chip") at one end and a lock recess 192. The opposite end of the base member mates with the proximal aperture 184 on the arm element 174 in such a way that the arm element 174 does not pivot relative to the proximal attachment element 176 once the two are locked together during use. For example, the ridged proximal engagement feature 190 is configured to engage with a corresponding ridged engagement feature 114 of first arm assembly 92 (or corresponding ridged engagement feature 166 of the second arm assembly 94). The locking pin 118 engages ramp surfaces of the lock recess 192 is configured to engage a portion of the locking pin 118 of the first arm assembly 92 (or locking pin 170 of the second arm assembly 94) to drive the ridged engagement features of the attachment element 176 and arm 174 together to effectively lock the construct. The lock recess 192 may be configured at various ramp angles to facilitate easier locking and more secure locking.

In the illustrated embodiment, the distal attachment element 178 is an engagement shim coupled to the arm element 174. The depicted shim is generally oar-shaped (by way of example), including a wide distal portion 194 and a narrow proximal portion 196. The distal portion 194 has a width dimension that corresponds to the distance between the elongated lip elements 50 of the side tracks 46 of the guide assembly 12, and a height dimension corresponding to the height dimension of the void created by the elongated lip elements 50, such that the distal portion 194 is configured to slideably mate with the side track 46. The distal portion 194 has a shaped distal end 198 that snugly fits into the lower portion of the side track 46 when the arm unit 105 is properly seated on the guide assembly 12. The distal portion 194 further includes a post 200 that extends through the distal aperture 186 of the arm element 174 and into the distal recess 188. A coupling element 202 is positioned within the distal recess 188 and receives a portion of the post 200 therein, pivotally coupling the distal attachment element 178 and the arm element 174. The narrow proximal portion 196 provides flexibility such that a locking element, for example, a shaped end 204 may mate snap into and mate with a recess or aperture 320 formed within slide track, locking the arm unit 105 in position when it properly seated on the guide assembly 12. A shim removal tool (not shown) may be advanced down the slide track to disengage the shaped end 204 from the window 320 and allow removal of the engagement shim from the slide track. In use, as may be explained in further detail below, the arm element 174 maintains its spatial orientation relative to the pivot rack 14 even while the user may be pivoting the guide assembly 12 (e.g. to restore spinal alignment etc.).

Figure 32A:
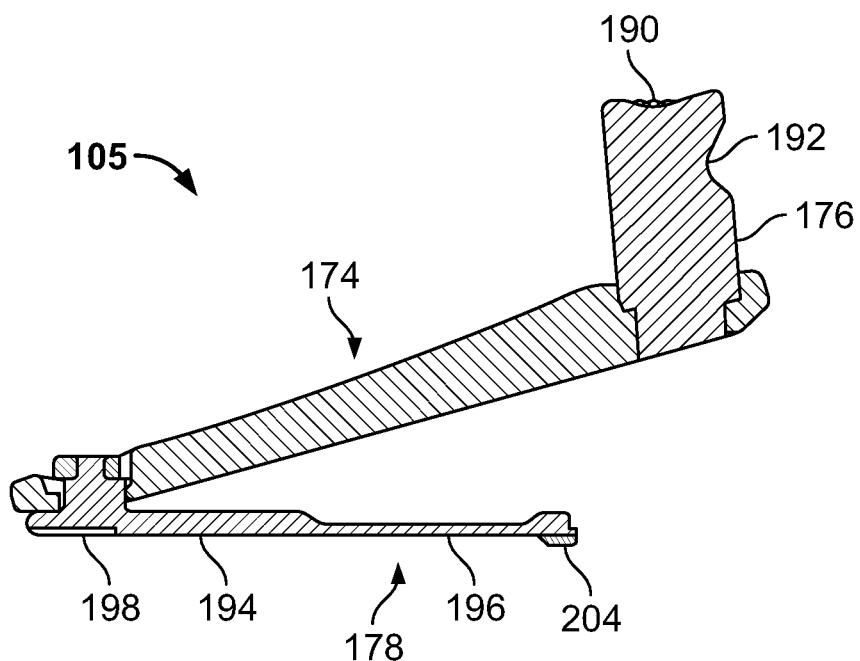
FIG. 32A-32B. Side (32A) and rear (32B) plan views of an example pivot rack arm element, showing degree of angulation.
Figure 32B:
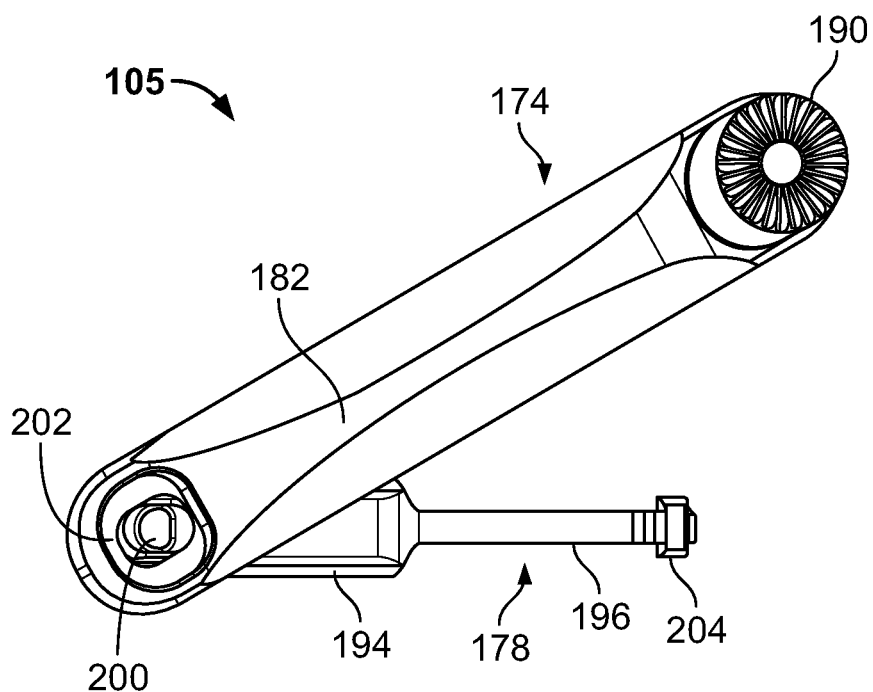
Figure 33A:
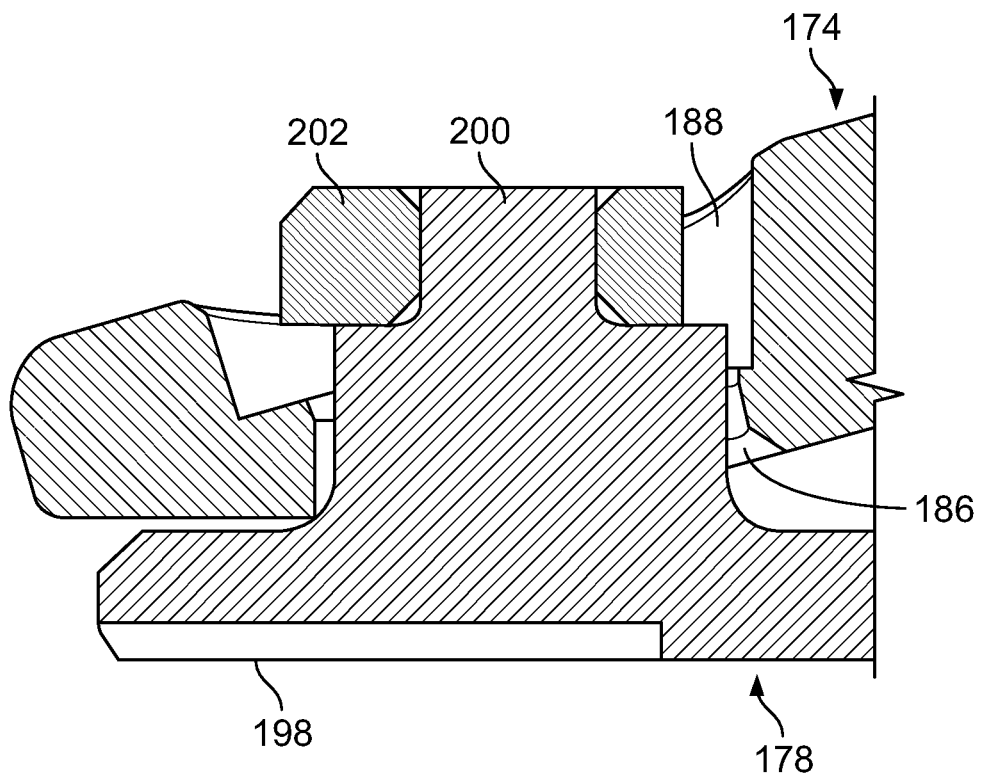
FIG. 33A-33B. Cross-sectional (33A) and rear plan (33B) detail views of components of the example pivot rack arm element shown in FIG. 32.

FIGS. 32-33 illustrate an example of how the distal attachment element 178 angulates relative to the arm unit 105. During use, the distal attachment element 178 will be fixed into the guide 12 while the arm unit 105 will be free to pivot and angle. The arm unit 105 is free to angle until the component features at the distal tip bottom out and prevent further rotation. According to one example, the arm unit 105 is free to angle up to 15.degree. lateral and .+-.30.degree. in the sagittal plane (until the component features bottom out). The distal attachment element 178 may be constructed to allow a certain degree of flexibility, to allow for easier attachment to the rack. It also allows the guide members 12 to cross entirely during fracture reduction (correction). Without the flexibility (i.e. if they were rigid to the guide members 12), correction potential would be limited at the point when the guide members 12 hit each other. With the flex, the guide members 12 can cross each other (as shown in the illustration, allowing 15.degree. of correction per side, or 30.degree. total of correction). The flex in the exemplary shim allows for easier attachment to the rack. It also allows the guides to cross entirely during fracture reduction (correction). Given such flexibility, the guides can cross (allowing 15.degree. of correction per side, or 30.degree. total of correction). According to one method, one can dial in distraction, then angulate, distract, angulate, as needed. This allows creation of ligamentotaxis as well as lordosis.

Figure 33B:
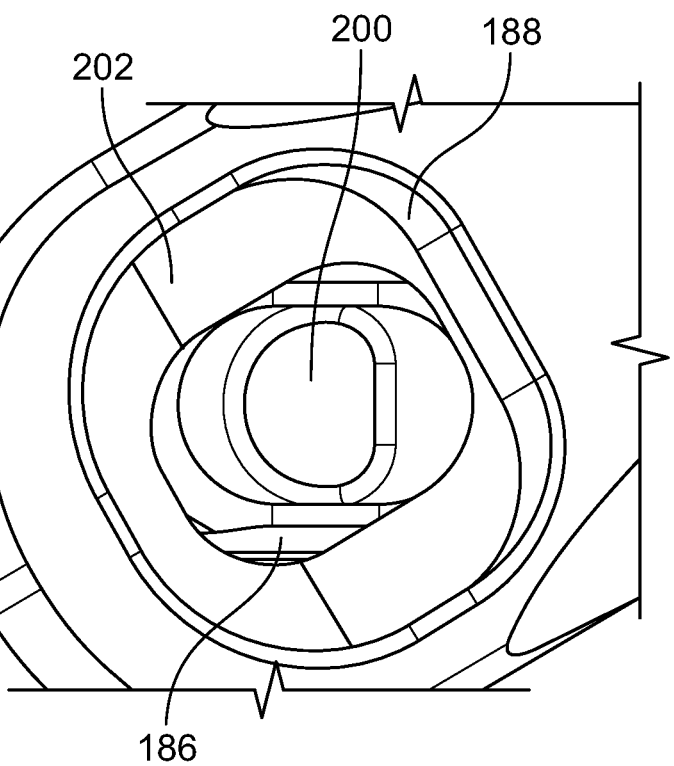
Figure 34:
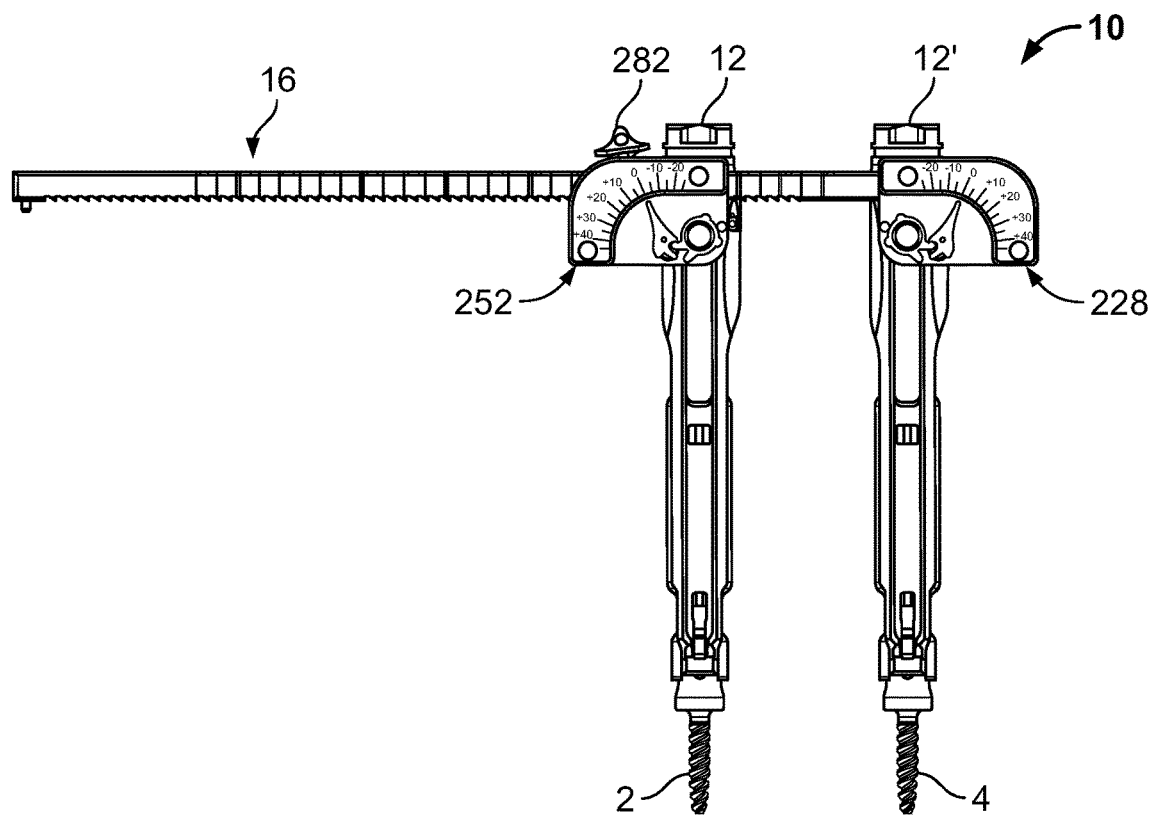
FIG. 34. An example of the locking rack attached to guide members in parallel orientation, showing the screw-to-screw distance as the sum of A, B, and C.
Figure 35:
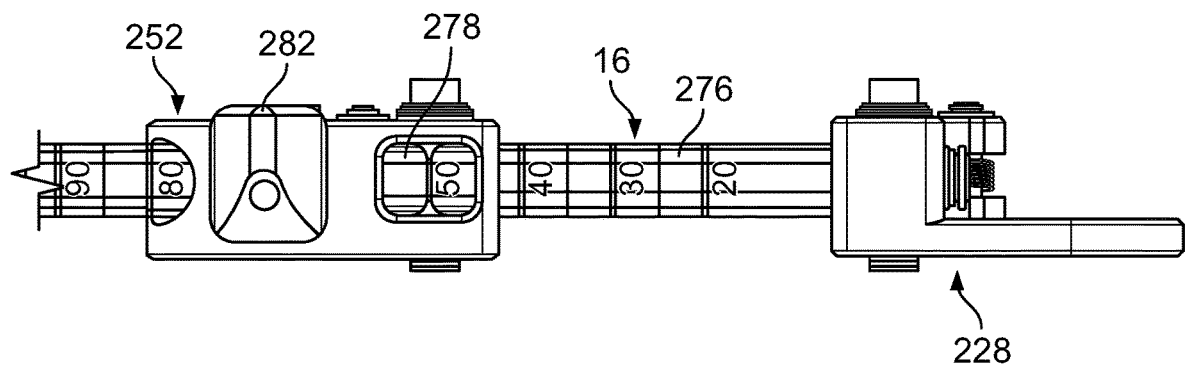
FIG. 35. A top plan view of an embodiment of the elongated rack member as positioned in FIG. 34, with marking to indicate the distance "A" between the center of each screw head; and the second calibration housing with a viewing aperture identifying the marking that corresponds to the current distance "A." Note that distance "A" is shown to be 50 mm, equal to the distance between the screws shown in FIG. 34.

Certain features may be included to facilitate this flexibility of the arm members 105 relative to the guide members 12. As an example, in the embodiment shown in FIGS. 33A and 33B the arm member 174 is able to pivot laterally relative to the distal attachment element 178. The distal aperture 186 is wide enough in at least one dimension to permit the arm member 174 to pivot laterally around the post 200. In the illustrated embodiment the distal aperture 186 is beveled in places to accommodate the post 200 over a range of angles. In various embodiments of the arm unit 105 the arm member 174 is free to pivot up to 5, 10, 15, 20, 25, 30, 35, 40, or 45.degree., depending on the geometries of the post 200 and the distal recess 186. In the illustrated embodiment the arm member 174 is free to rotate relative to the distal attachment element 174 about an axis approximately parallel to the post. As can be seen in FIG. 33B, the distal aperture 186 has the shape of a polygon with rounded corners, the post 200 has the shape of an oval with two parallel sides, and the coupling element 202 is generally "D" shaped with a curved side and a straight side. As the diagonal distance between the curved corners of the post 200 is less than the diagonal distance between opposite parallel sides of the distal aperture 186 in some orientations, the post 200 is able to rotate to a limited degree. The degree of rotation allowed can be designed as necessary. Specific embodiments of the arm unit 105 permit saggital rotation of the arm member 174 relative to the distal attachment element 178 of up to 5, 10, 15, 20, 25, 30, 35, 40, and 45.degree. in either direction.

The locking rack 16 serves to restrict the relative movement of the proximal portions of the guide members 12 during reorientation, and can optionally display measurements of the relative positions of the guide members 12. As further described below, such measurements can include one or both of the relative angles of the guide members 12 and the distance between the bone anchor assemblies 2. The locking rack 16 connects to the first and second guide members 12, 12', to reversibly prevent the guide members from rotating relative to one another in at least one direction. Some embodiments of the pivot rack 14 are designed only to prevent rotation of the guides 12 away from one another. In other words, the locking rack 16 maintains the correction achieved as the proximal ends of the guides 12 converge or diverge from each other. Alternatively, the rack 16 could be configured to reversibly prevent the guides 12 from rotating towards each other. In another alternative, the locking rack 16 may be configured to allow the direction of locking to be user selected. As shown in FIGS. 23-25 and 51-53, the locking rack 16 can comprise an elongate locking rack member 210, a first connector arm assembly 212 connected to the elongate locking rack member 210 and having a first connector arm 230, a second connector arm assembly 214 slideably connected to the elongate locking rack member 210 and having a second connector arm 230, and a locking mechanism that reversibly locks the second connector arm assembly 214 against sliding relative to the elongate locking rack member 210 in at least one direction.

Some embodiments of the first connector arm assembly 212 may be configured to rotate relative to the elongate locking rack member 210 about the longitudinal axis of the elongate locking rack member 210. The first connector arm assembly 212 may be connected to the elongate locking rack member 210 in a slidable manner. If the first connector arm assembly 212 is slidable relative to the elongate locking rack member 210, then it will also be lockable in at least one direction.

The first and second connector arms 230 are configured to fixedly attach to a guide member 12 and configured to allow the connector arm to rotate about a at least one axis relative to the connector arm assembly (212, 214), enabling the guides 12, 12' to rotate relative to the locking rack 16 in a first direction (e.g. towards each other), while constraining them from rotating in the opposing direction. Some embodiments of the connector arm assemblies (212, 214) are configured to allow the connector arms 230 to translate along at least one axis relative to the connector arm assemblies (212, 214). In the embodiment shown in FIGS. 23-27 and 51-53, each connector arm 230 has an elongate proximal attachment element 292 that serves to connect the connector arm 230 to the connector arm assemblies (212, 214) by way of a lateral aperture (238, 260). In that embodiment the connector arm 230 is free to rotate about the longitudinal axis of the proximal attachment element 292 and to translate along the same axis.

By way of example only, FIGS. 23-31 illustrate an example of a locking rack 16 forming part of the spinal trauma correction system 10 according to one aspect of the disclosure. The exemplary locking rack 16 engages with the guide assemblies 12 and performs several functions. First, as will be explained, the locking rack 16 includes a passive locking element 294 (e.g. ratchet mechanism) that enables the locking rack 16 to maintain the orientation of the guide assemblies 12 during convergence. Second, the locking rack 16 includes markings that are calibrated to calculate the necessary length and angulation (bend) of the spinal rod 6 prior to insertion.

Figure 53:
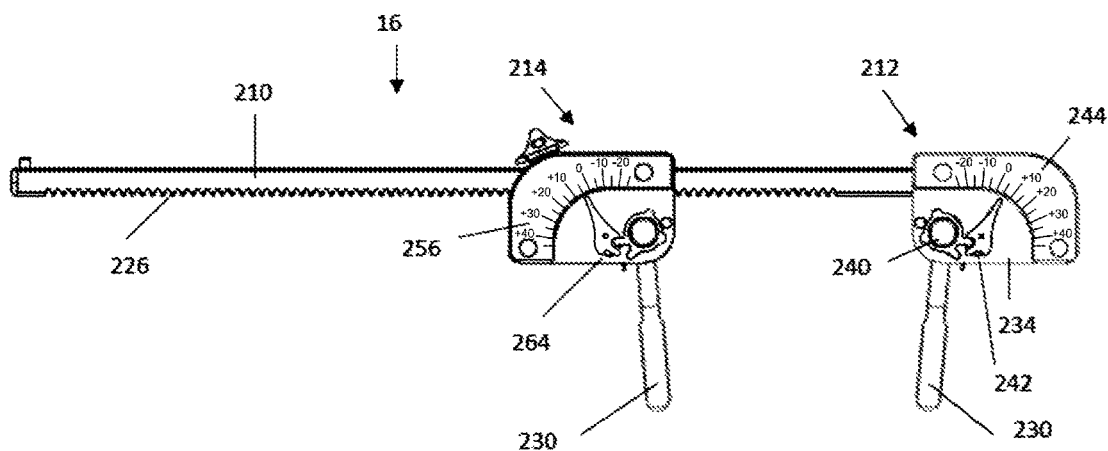
FIG. 53. A front plan view of the embodiment of the locking rack shown in FIG. 51.

In the illustrated embodiment, the locking rack 16 includes an elongated rack member 210, a first connector arm assembly 212 and a second connector arm assembly 214. The elongated rack member 210 has a first end 216 rotatably attached to the first connector arm assembly 212 (to allow the first connector arm assembly to rotate about the longitudinal axis of the elongated rack member 210) and a second end 218 that includes a translation stop 220 that prevents translation of the second connector arm assembly 214 beyond the end of the rack member 90. The elongated rack member 210 further includes a top surface 222 and a bottom surface 224. The top surface 222 may be generally planar and may include a plurality of calibration markings distributed thereon. The bottom surface 224 includes a plurality of angled ridges 226 (e.g., ratchet teeth) that allow for unidirectional movement of the second arm assembly 214 (when the ratchet toggle 282 is in the "locked" position). For example, unidirectional movement may be facilitated by angled ridges in a saw toothed configuration (FIG. 25). The saw tooth ridges depicted in FIG. 25, for example, are oriented to allow the second connector arm assembly 214 to translate away from the first connector arm assembly 212 while prohibiting the opposite translation towards the first connector arm assembly 212. This allows the proximal ends 24 of the guides 12 to be rotated towards each other while preventing them from rotating back. In an alternative embodiment, the tooth angle may be unbiased or delta toothed (FIG. 53). With the delta teeth, the locking toggle 282 may operate as above to inhibit translation in a single direction. Alternatively, with the delta teeth, the locking toggle may be configured to select the direction in which translation will be inhibited, thus allowing the locking rack 16 to be selectively unidirectional in either direction. For example, the toggle 282 may have a first locked positon to inhibit translation in a first direction, a second locked position to inhibit translation in a second direction, and an unlocked position. Some embodiments of the delta-toothed teeth are equilateral triangles.

The connector arm assemblies (212, 214) allow the connector arms 230 several degrees of freedom relative to one another. This allows the connector arms 230 to connect to guide members 12 in a wide array of relative configurations. To recap such configurations shown in the embodiments illustrated in FIGS. 23-31 and 51-59: the first connector arm assembly 212 rotates about the longitudinal axis of the elongate member 210 (and thus rotates relative to the second connector arm assembly 214 about the same axis); both connector arm assembles (212, 214) allow the connector arms 230 to translate along the longitudinal axes of their respective proximal attachment elements 292; both connector arms assemblies (212, 214) allow the connector arms 230 to rotate about the longitudinal axes of their respective proximal attachment elements 292; and the second connector arm assembly 214 translates along the elongate locking rack element 210 relative to the first connector arm assembly 212. Thus the two connector arms 230 are free to translate in two dimensions and rotate in two dimensions relative to one another.

In the illustrated embodiment, the first connector arm assembly 212 includes a first calibration housing 228 and a connector arm 230. The first calibration housing 228 is shown at the first end 216 of the elongated rack member 210. By way of example, the first calibration housing 228 includes a longitudinal aperture 232 positioned at one end of the housing 228 and configured to receive the first end 216 of the elongated rack member 210 therein and to rotate about the longitudinal axis of the elongated locking rack member 210. The first calibration housing 228 further includes a first side 234 that is oriented facing the user, a second side 236 that is oriented facing the guide assembly 12, and a lateral aperture 238 extending through the first calibration housing 228 between the first and second sides 234, 236. The first side 234 may include a calibration system including a cam 240, needle 242, and markings panel 244. The cam 240 includes an aperture sleeve extension 246 that extends at least partially into the lateral aperture 238. The aperture sleeve extension 246 is generally cylindrical except for the presence of opposite parallel sidewalls 248. The aperture sleeve extension 246 is configured to receive the proximal attachment element 292 of the connector arm 230 therein. The aperture sleeve extension 246 is rotatable within the lateral aperture 238 and includes a lateral flange 248 that engages a flange 250 on the needle 242, causing the needle 242 to move in response to movement of the cam 240. The needle 242 will then rotate and point to a certain marking to help inform the user of the length and angulation of the spinal rod 6.

Figure 36:
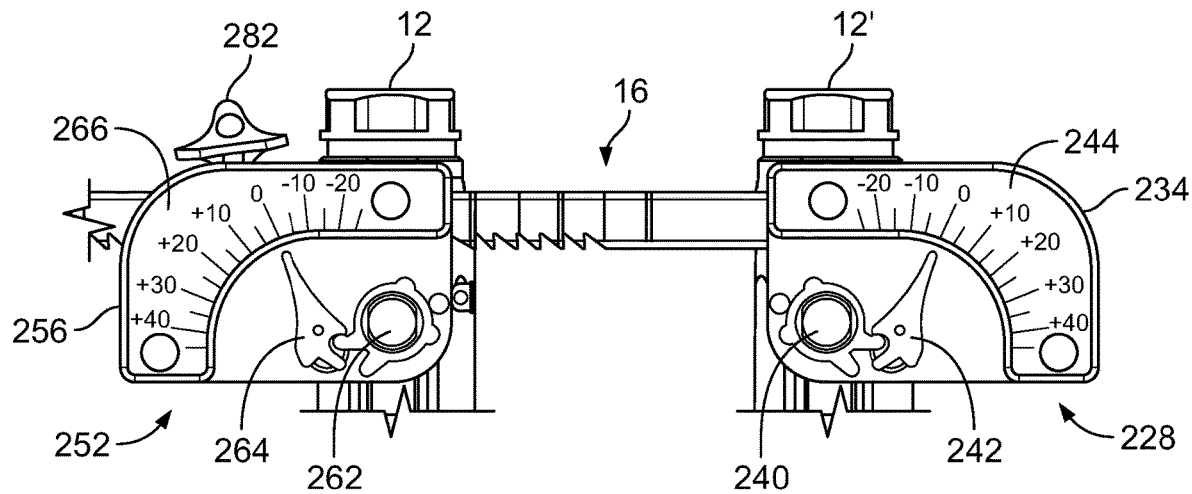
FIG. 36. A front plan view of an embodiment of the two calibration housings engaged to the guide members and the elongate locking rack member as positioned in FIG. 34, showing detail of the cam and needle mechanism for indicating the relative angulation of each guide member. Note that 0.degree. is shown as the relative angulation of the guide members, which are parallel in FIG. 34.
Figure 37:
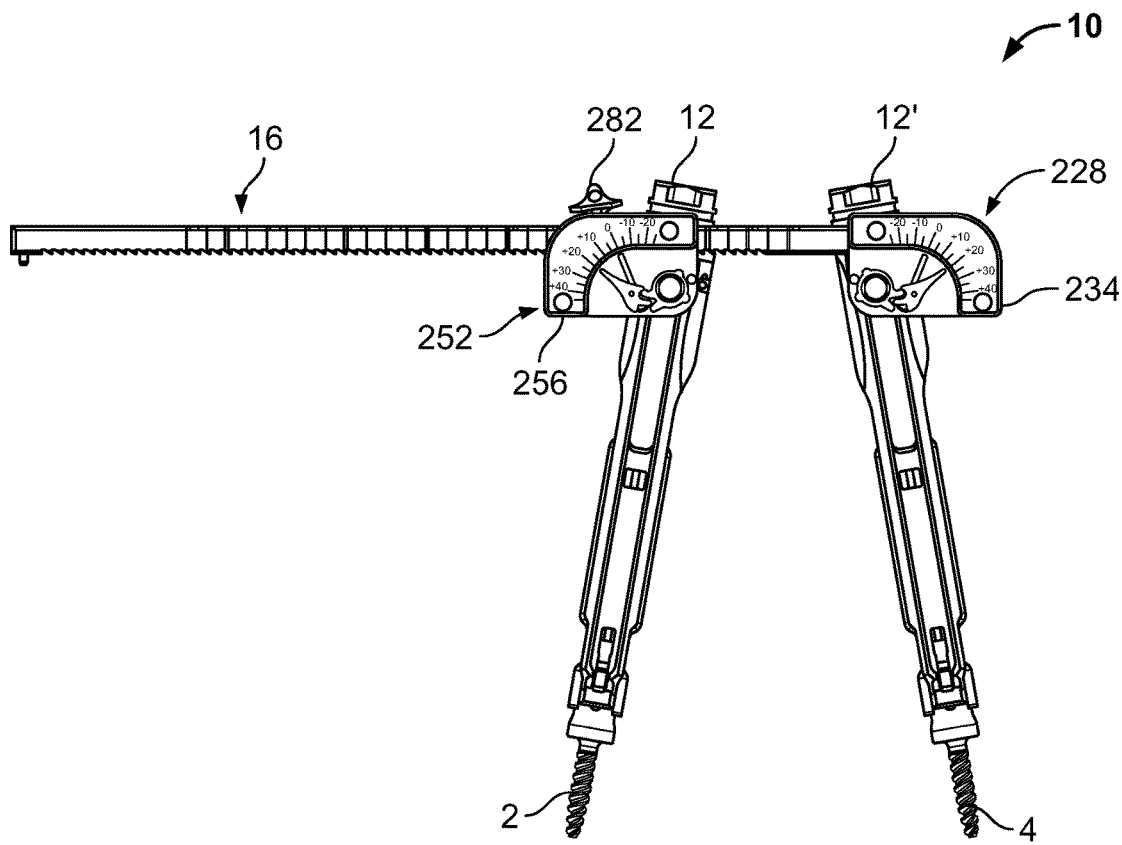
FIG. 37. A front plan view of the entire locking rack with the guide members in non-parallel alignment.
Figure 38:
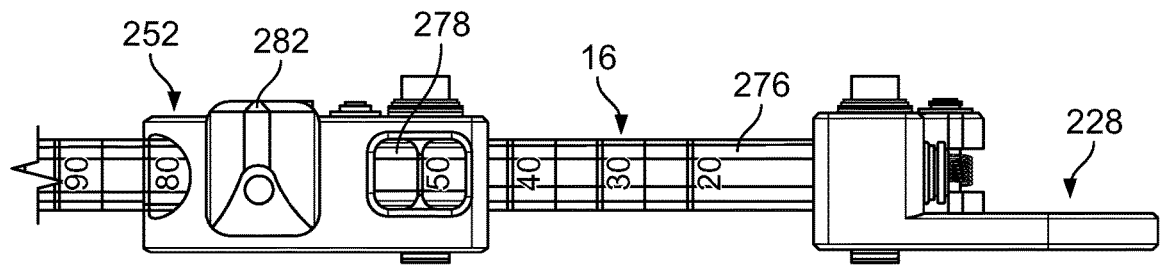
FIG. 38. A top plan view of an embodiment of the elongated rack member as positioned in FIG. 37, with marking to indicate the distance "A" between the center of each screw head; and the second calibration housing with a viewing aperture identifying the marking that corresponds to the current distance "A." Note that distance "A" is shown to be 50 mm, equal to the distance between the screws shown in FIG. 37.
Figure 39:
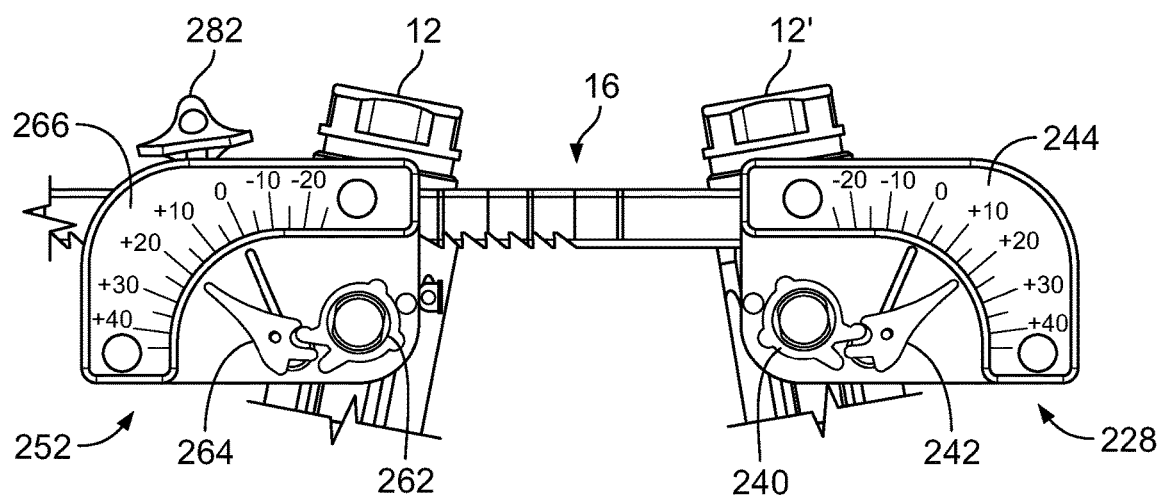
FIG. 39. A front plan view of an embodiment of the two calibration housings engaged to the guide members and the elongate locking rack member as positioned in FIG. 37, showing detail of the cam and needle mechanism for indicating the relative angulation of each guide member. Note that 0.degree. is shown as the relative angulation of the guide members, which are parallel in FIG. 37.
Figure 40:
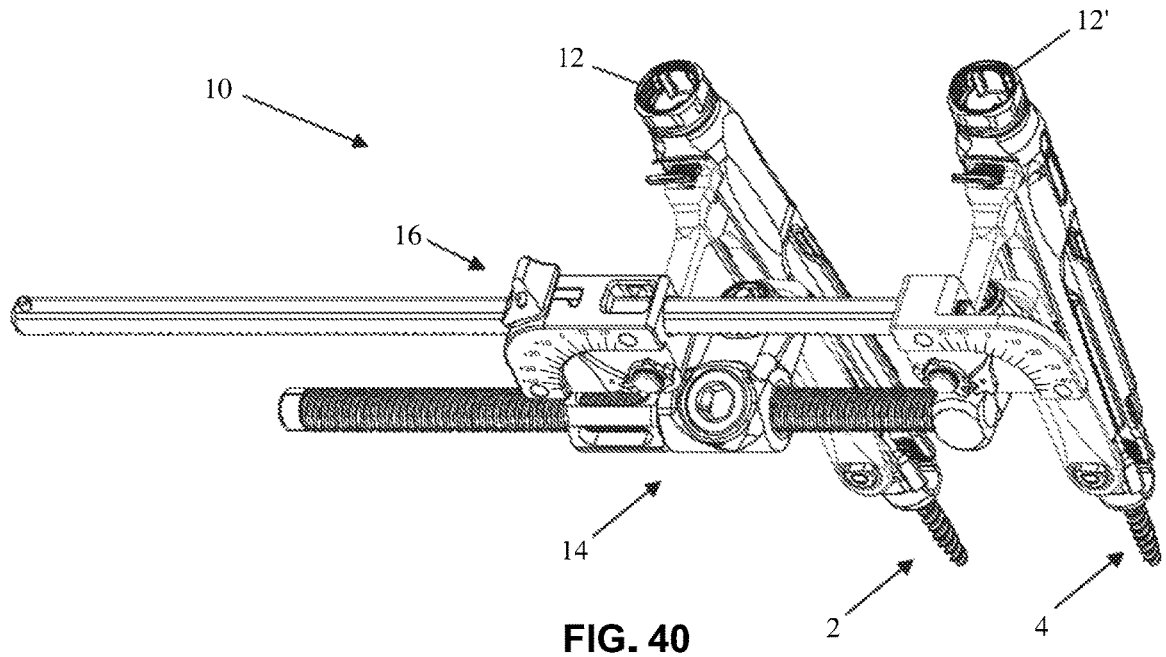
FIG. 40. A front perspective view of an alternative embodiment of the spinal fixation/correction system.
Figure 41:
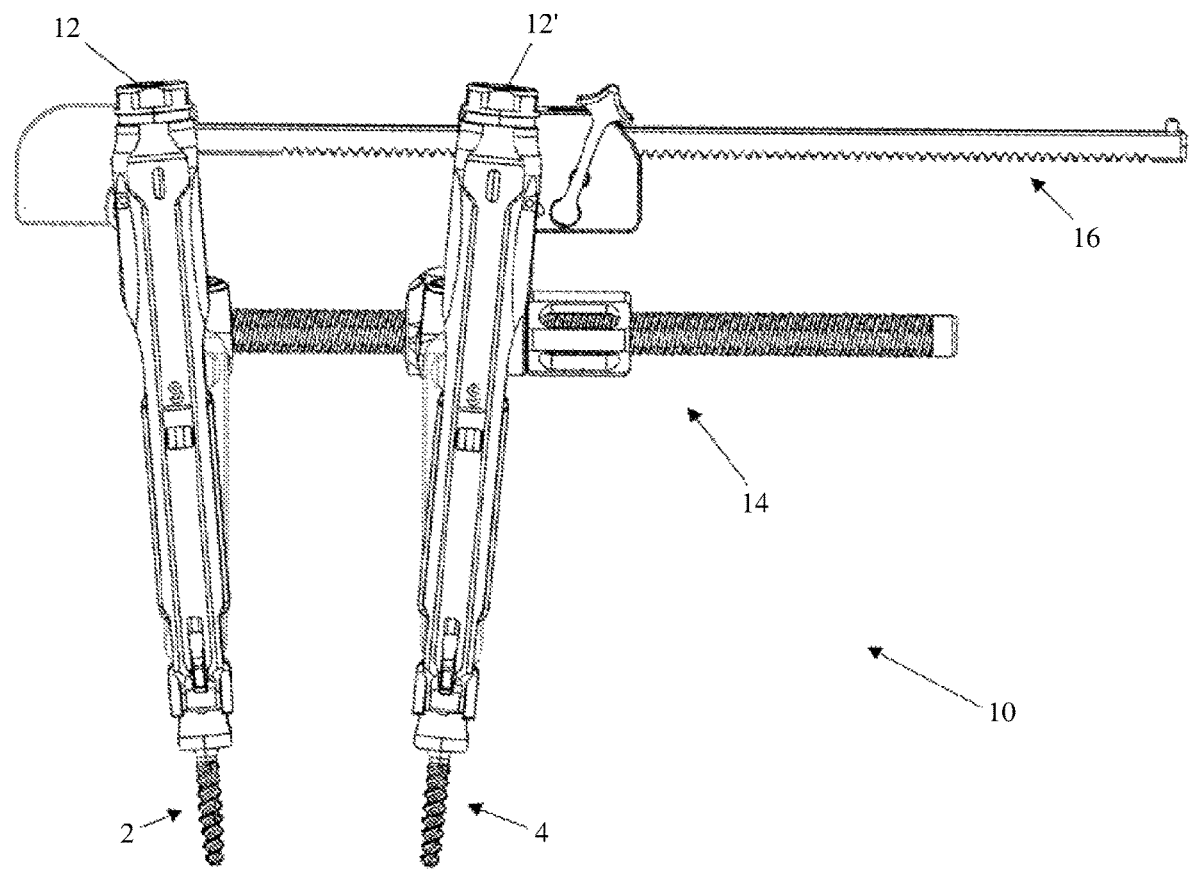
FIG. 41. A front plan view of the embodiment of the system shown in FIG. 40.
Figure 42:
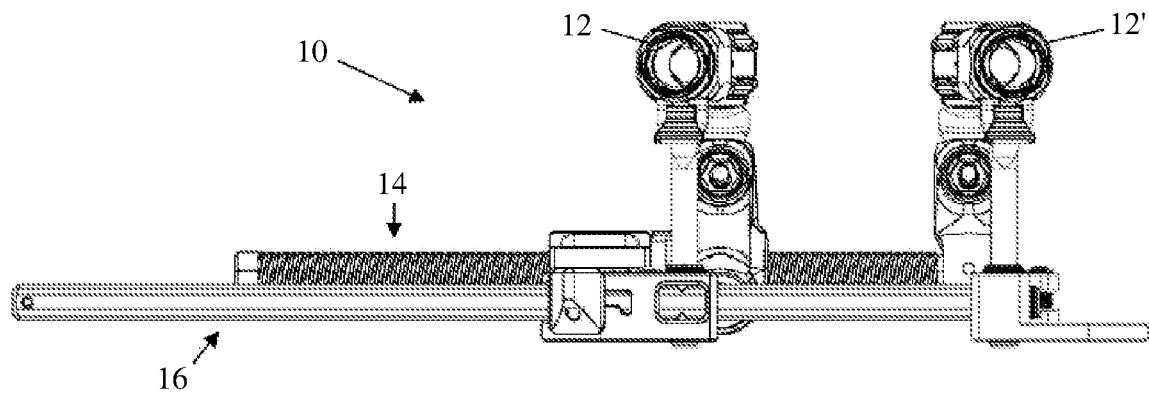
FIG. 42. A top plan view of the embodiment of the system shown in FIG. 40.
Figure 43:
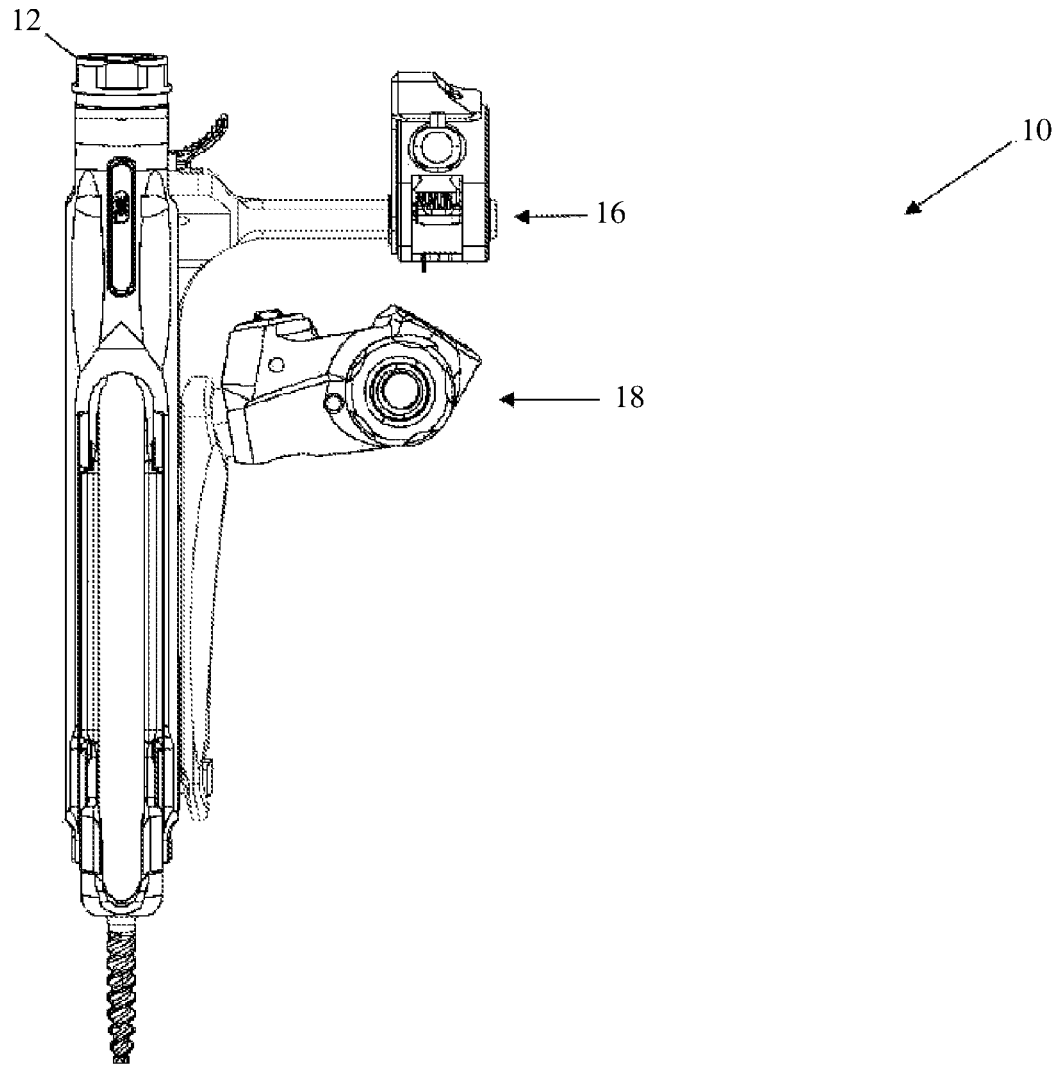
FIG. 43. A side plan view of the embodiment of the system shown in FIG. 40.

The illustrated embodiment of the second connector arm assembly 214 includes a second calibration housing 252 and a connector arm 230. The second calibration housing 252 is generally positioned near the second end 218 of the elongated rack member 210, and is translatable along at least a substantial portion of the length of the elongated rack member 210. By way of example, the second calibration housing 252 includes a longitudinal lumen 254 extending through the housing 252 and configured to translationally receive the elongated rack member 210 therethrough. The second calibration housing 252 further includes a first side 256 that is oriented facing the user, a second side 258 that is oriented facing the guide assembly 12, and a lateral aperture 260 extending through the second calibration housing 252 between the first and second sides 256, 258. The first side 256 may include a calibration system including a cam 262, needle 264, and markings panel 266. The cam 262 includes an aperture sleeve extension 268 that extends at least partially into the lateral aperture 260. The aperture sleeve extension 268 is generally cylindrical except for the presence of opposite parallel sidewalls 270. The aperture sleeve extension 268 is configured to receive the proximal attachment element 292 of the connector arm 230 therein. The aperture sleeve extension 268 is rotatable within the lateral aperture 260 and includes a lateral flange 272 that engages a flange 274 on the needle 264, causing the needle 264 to move in response to movement of the cam 262. The needle 264 will then rotate and point to a certain marking (e.g., FIGS. 1, and 36) to help inform the user of the length and angulation of the spinal rod 6. This allows the arm elements 230 to rotate relative to one another in three axes (the longitudinal axes of each of the two proximal attachment elements 292 and the axis of the elongate locking rack member 210) and translate relative to one another in three axes (the longitudinal axes of each of the two proximal attachment elements 292 and the axis of the elongate locking rack member 210).

The illustrated embodiment of the second connector arm assembly 214 further includes a top surface 276 including a viewing aperture 278 for viewing certain markings on the top surface 222 of the elongated rack element 210. The viewing aperture 278 may include at least one pointer 280 to provide a precise identification of the marking. The top surface 276 also includes a toggle switch 282 to toggle the passive locking mechanism between "locked" and "unlocked" configurations. In the "locked" configuration, the toggle switch 282 urges a ratchet lever (not shown) to engage the ratchet teeth 226, ensuring unidirectional movement of the second arm assembly 214 along the elongated rack element 210. In the "unlocked" configuration, the toggle switch 282 urges the ratchet lever away from the ratchet teeth 226, enabling bidirectional movement of the second connector arm assembly 214 along the elongated rack element 210. In an alternative embodiment, on the "locked" configuration, the toggle switch 282 urges a ratchet lever (not shown) to engage delta-form teeth, preventing movement of the second connector arm assembly 214 along the elongated rack element 210 in both directions. In a further alternative embodiment, locking mechanism 282 has three positions: unlocked, locked against moving toward first locking arm assembly 212, and locked against moving away from first locking arm assembly 212.

Figure 54:
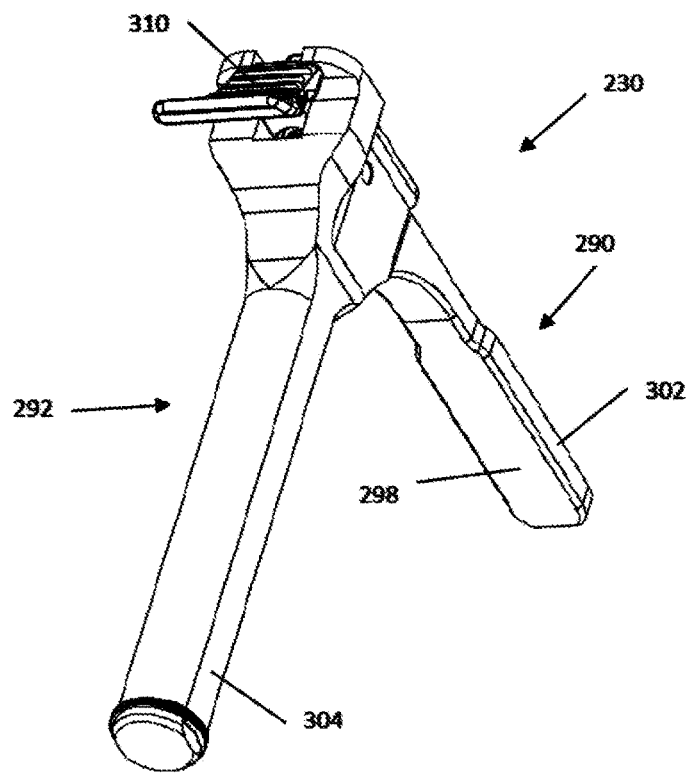
FIG. 54. A front perspective view of the arm unit of the embodiment of the locking rack shown in FIG. 51.
Figure 55:
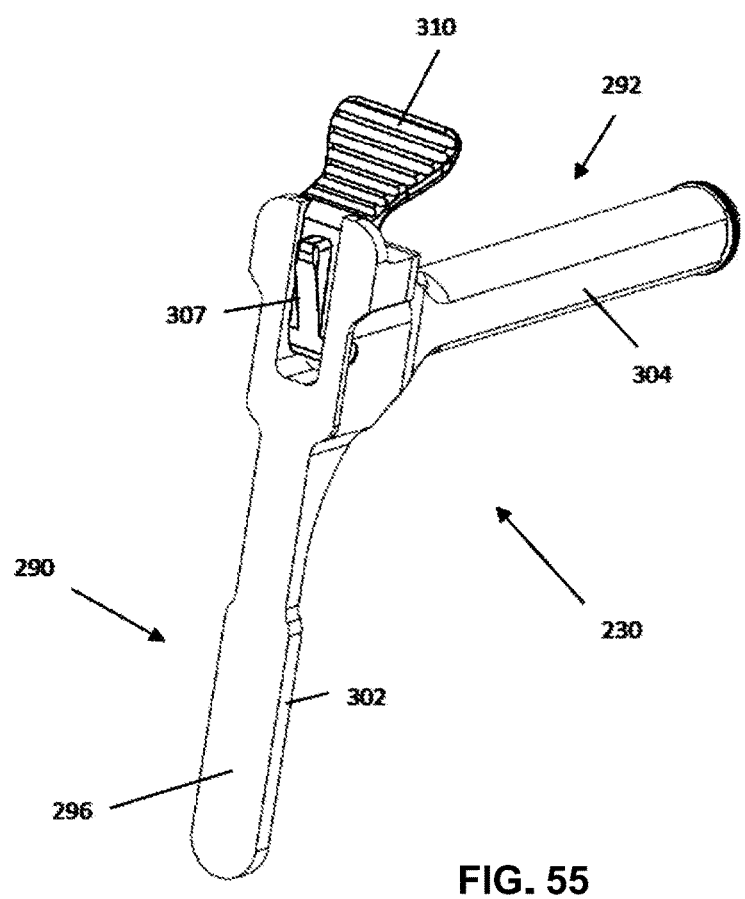
FIG. 55. A rear perspective view of the arm unit of the embodiment of the locking rack shown in FIG. 51.
Figure 56:
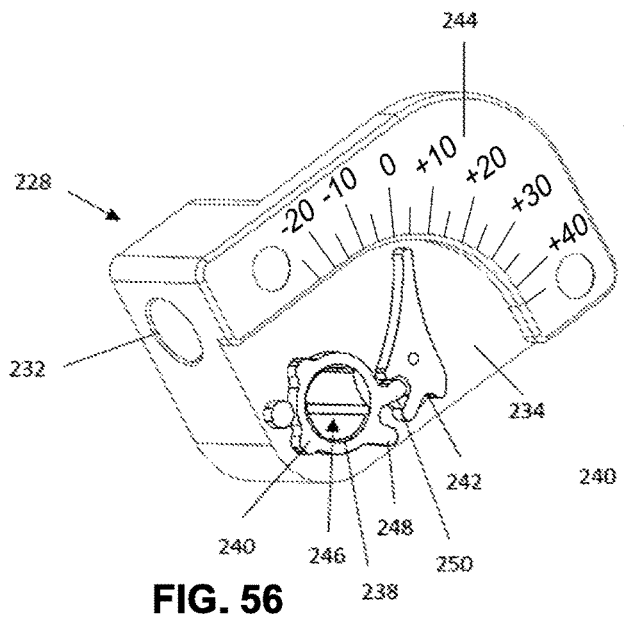
FIG. 56. A front perspective view of the first calibration housing of the embodiment of the locking rack shown in FIG. 51.
Figure 57:
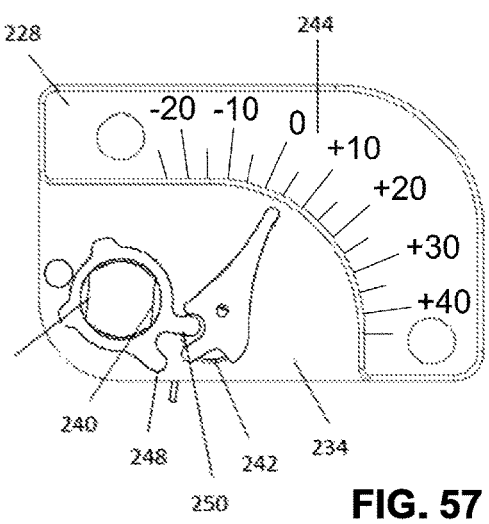
FIG. 57. A front plan view of the first calibration housing of the embodiment of the locking rack shown in FIG. 51.
Figure 58:
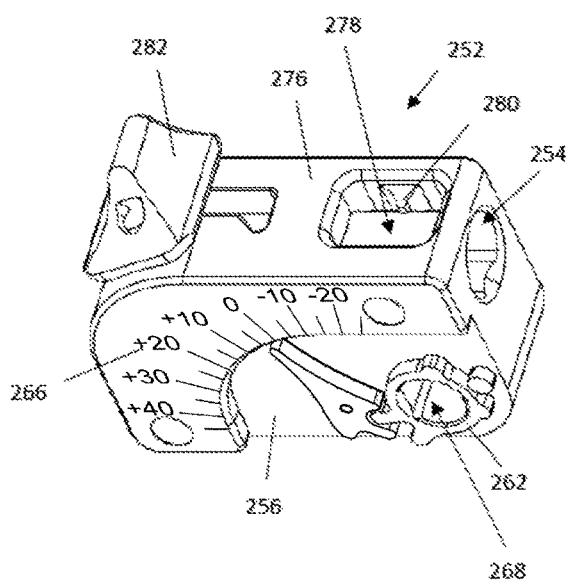
FIG. 58. A front perspective view of the second calibration housing of the embodiment of the locking rack shown in FIG. 51.
Figure 59:
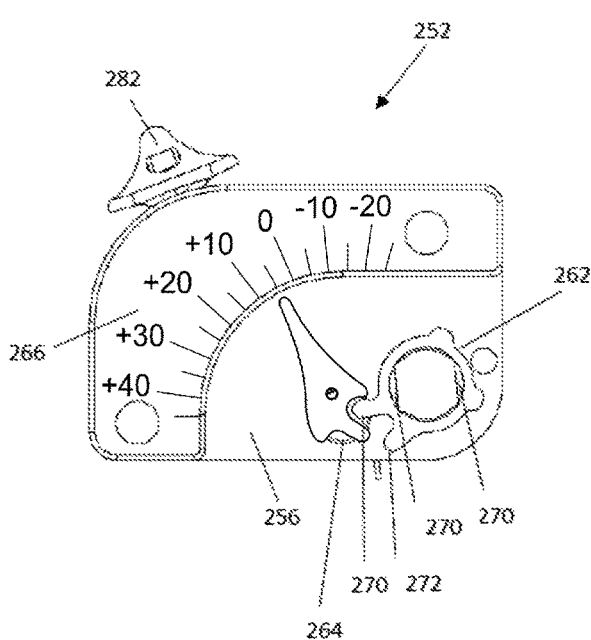
FIG. 59. A front plan view of the second calibration housing of the embodiment of the locking rack shown in FIG. 51.

The illustrated embodiment of the connector arm 230 (which is identical for both the first and second arm connector assemblies 212, 214) includes an arm element 290, a proximal attachment element 292, and a locking element 294 (as shown in FIG. 26). The arm element 290 is a rigid, elongated member that functions to hold the locking rack 16 steady and help ensure that the guide assemblies 12 maintain their orientation during compression/distraction of the target spinal area. The arm element 290 further includes a front side 296, a backside 298, and a perimeter edge 302. By way of example only, the front side 296 is configured to face the guide assembly 12, and therefore may have a generally smooth, flat surface. The backside 298 is configured to be tissue-facing during use, and therefore has a contoured surface to minimize unnecessary trauma to the surrounding tissue during use. Shoulders 303 along the front side 296 near the top of the perimeter abut complementary ledges 305 near the top of the side track to prevent the arm elements from advancing too far distally along the track. A locking element 294 is positioned within the arm element 290 and may take various forms, such as a hex head (as shown in FIGS. 26 and 27), and a manual switch feature 310 (e.g., a thumb switch as shown in FIGS. 54-55) for manual engagement and a distal projection element 307. The projection locking element 530 is capable of assuming an extended position and a retracted position; in the extended position the projection element 530 extends beyond the front side 296 of the connector arm 230, while in the retracted position the projection element 530 does not extend beyond the front side 296 of the connector arm 230. The locking element 294 may be biased using a spring or other means. In a specific embodiment the locking element 294 is spring-biased toward the extended position. The projection element 530 is dimensioned to fit within one of the apertures 320 in the guide member 12. This locks the connector arm 230 to the guide member 12.

The illustrated embodiment of the arm element 290 has a width dimension that corresponds to the distance between the elongated lip elements 50 of the side track 46 of the guide assembly 12, and a height dimension corresponding to the height dimension of the void created by the elongated lip elements 50, such that the arm element 290 (via the perimeter edge 302) is configured to slidebly mate with the side track 46 of the guide assembly 12.

The illustrated embodiment of the proximal attachment element 292 comprises a generally cylindrical base member having opposite parallel sidewalls 304 that fit snugly into the aperture sleeve extensions 246, 262 of the first and second arm connector assemblies 212, 214. As the guide assembly 12 is manipulated by a user (e.g. to effectuate vertebral rotation), the connector arm 230 will rotate, which in turn rotates the cam 240, 262 and needle 242, 264 as described above.

The measurement functionality of the locking rack 16 is illustrated in FIGS. 34-39, to provide a screw to screw distance and angle. The locking rack 16 provides a distance measurement (shown as "A") along the rack beam; this measurement "A" is the screw to screw distance if the guides are parallel. The locking rack 16 also provides measurement "B" and "C" shown on a dial; this measurement is the distance from the screw to the parallel reference due to the angulation of the guides (and thus the screw). The distance can be either positive or negative, as the guides 12 may be angled to either diverge or converge at their distal ends. Therefore, the screw to screw distance can be obtained by adding measurements "A+B+C". Measurements "B" and "C" may also be used to derive a screw angle by dividing the associated dial measurement by 2. The dial may cover various ranges of angulation. The embodiment shown in FIG. 1 has a range of distances from −30 mm to +30 mm. The alternative embodiment shown in FIG. 36 has a range of −20 to +40 mm. These ranges can be varied as necessary for the intended application.

The distances shown on the marking panel on the calibration system is a function of the combined geometries of the cam 240, 262, the needle 264, 242, and the locations of the markings 244, 266. The flange 250, 274 on the cam 240, 262 rotates as the arm element rotates. As explained above, the distance shown on the top surface of the elongated locking rack member 210 is simply the distance between the proximal attachment elements of the first and second locking arms 540a, 540b where they connect to the respective first and second locking arm assemblies 550a, 550b. This is also the distance between the bone anchor assemblies 2, 4 if the guides 12 are parallel. If the guides 12 are not parallel, the distance between the anchor assemblies 2, 4 will differ from the distance between the proximal attachment elements of the first 540a and second locking arms 540b where they connect to the respective first and second locking arm assemblies 550a, 550b. However, there is not a linear relationship between the angle of the cam 240, 262 and the difference in the distance between the first and second locking arms 540a, 540b. To account for this, the flange 250, 274 and the cam 240, 262 interact to provide rotation of the needle 242, 264 that is not identical to the angular rotation of the cam 240, 262. Furthermore, the distance markings on the markings panel 244, 266 can be arranged as necessary to account for such nonlinear correspondence. In the embodiment shown in FIGS. 36 and 39, the markings panels 244, 266 range from +40 mm to −20 mm (possible cumulative difference of −40 to +80 mm). In the embodiment of the system shown in FIGS. 36 and 39 the angle of the guide member 12 in degrees is half of the distance shown in mm (in the specific illustrated example in FIGS. 37-39, each guide member 12 is angled 10.degree. from perpendicular to the elongate locking rack member 210, and the distal end of each guide member each is 20 mm outside of that reference position).

In use, the various tools described above may be assembled to create a fracture correction tool and employed through various methods in the surgical treatment and correction of traumatic vertebral fractures from a posterior approach. By way of example, the tools may be useful in treating burst fractures, distraction (or "Chance") fractures, and fracture-dislocations, among others. The example methods generally involve securing a pair of (first and second) bone anchor assemblies 2, 4 to a pair of (corresponding first and second) vertebral structures. A pair of (first and second) bone anchor assembly 2 guide members 12, 12' are connected to the bone anchor assemblies and extend out beyond the skin level of the patient. The bone anchor assemblies and guide members 12, 12' are preferably secured together prior to implantation and each bone anchor assembly 2 and guide members 12 combination are advanced to the appropriate vertebra through separate minimally invasive incisions. Alternatively however, the guide members 12, 12' could be engaged to the bone anchors 2, 4 after the bone anchor assemblies 2, 4 have been implanted. This may be particularly useful, for example, if the trauma correction device is utilized in an open procedure with the entire target area of the spine exposed through one larger incision. The guide members 12, 12' and bone anchor assemblies are not limited in structure in the technique, but may be any that are described above as suitable for use in the system.

With the bone anchor assemblies 2, 4 in implanted in position, the pivot rack 14 and locking rack 16 are coupled to bone guide members 12, 12' to complete the fracture correction tool setup. As previously described, the pivot rack 14 initially fixes the distance between the bone anchor assemblies 2, 4 and imparts a pivot point at the distal end of each guide members 12 about which the guide members 12 (and associated screw) can rotate. The pivot rack 14 may further be optionally used to apply compression or distraction by adjusting the distance between the bone anchor assemblies 12. The locking rack 16 restricts movement of the guide members 12, 12' relative to one another in one direction to provide a passive locking that maintains the angular correction achieved when the guide members 12, 12' are rotated relative to each other. Further, the locking rack 16 can also provide a visual indication to the user indicative of the relative angulation and/or distance of the bone anchor assemblies 2,4, for example, to facilitate the selection of the appropriate size and bend of a rod.

Once the racks 14, 16 are in place, correction may be applied by one or both of angulating the nearby vertebral structures to restore a more natural alignment and translating the nearby vertebral structures to provide compression or distraction and achieve ligamentotaxis. Angulation can be achieved by rotating the proximal ends of the first and second guide members 12, 12' relative to one another. The guide members 12, 12' rotate about the pivot points from the pivot rack 14, thereby angulating the associated bone anchor assembly 2. Translation of the bone anchor assemblies 2,4 can be achieved by translating the distal ends 26 of the first and second guide members 12, 12' relative to one another using the pivot rack translation mechanism 130. Once the desired correction has been achieved, a spinal rod is emplaced into the bone anchor assemblies 2,4 to maintain their new positions. It will be appreciated that the final construct may further include additional screws implanted superior and/or inferior to the screws adjacent the fracture with the rod connecting all of the screws.

Figure 60:
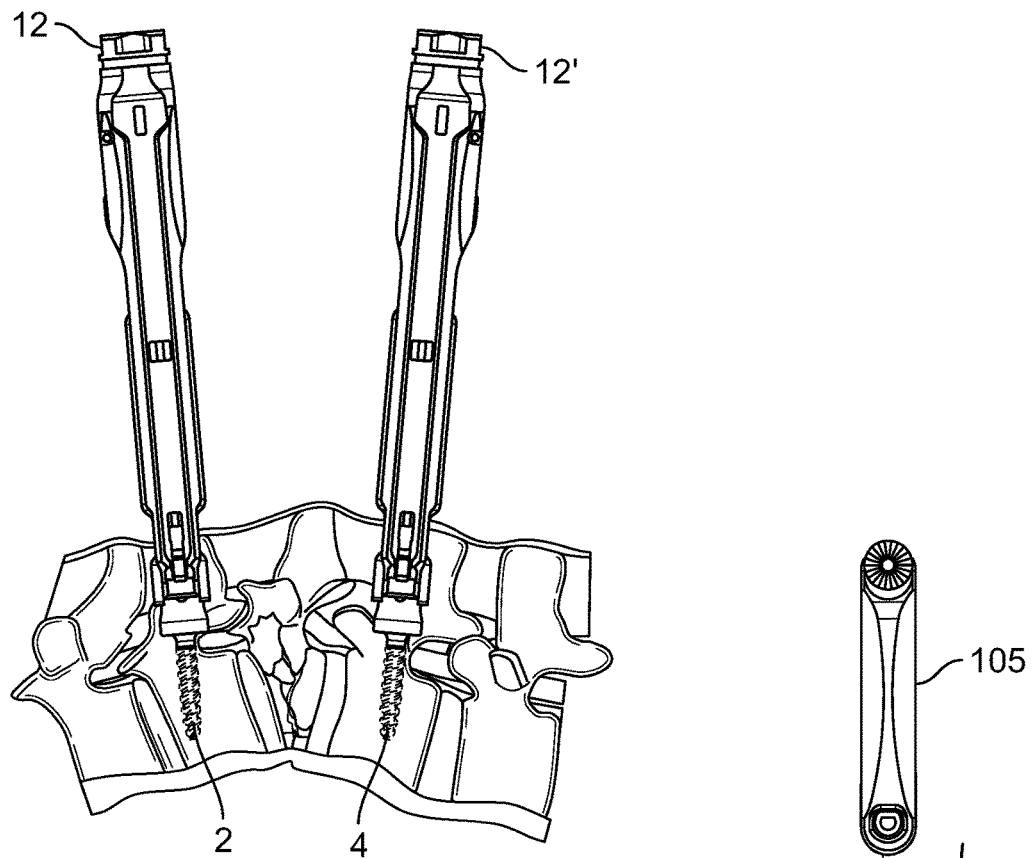
FIG. 60. An illustration of embodiments of the bone anchor assembles in place in the pedicles of the vertebrae superiorly and inferiorly adjacent to a fractured, with embodiments of the guide towers attached.

By way of example, a minimally invasive surgical method for correcting a vertebral fracture is now described in more detail. First, with reference to FIGS. 60-65 an exemplary method for assembling the tools together to create a fracture correction tool 10 is described. It should be appreciated that while FIGS. 62-65 are depicted with right extending locking rack 16 and pivot racks 14, a left extending rack may be similarly used (as depicted in FIGS. 66-75) to change the direction (e.g. cranial or caudal) in which the racks 14, 16 extend, according to surgeon preference. With the patient in the desired position (e.g. prone) on the surgical table, the pedicles of the vertebrae superiorly and inferiorly adjacent to fractured vertebra are targeted using known techniques (e.g. k-wires, fluoroscopy, surgical navigation, nerve monitoring) and bone anchor assemblies 2,4 with guide members 12, 12' attached, are implanted through the pedicles (FIG. 60). According to the present example the bone anchor assemblies 2,4 placed adjacent the fracture ("trauma anchors") are fixed axis bone anchor assemblies 550. As previously described however, other anchors 2,4 may be utilized in which the anchor housing 74 initially angulates relative to the anchor shank but can thereafter be arrested prior to imparting correction (e.g. so called provisional locking screws), or, wherein angulation of the housing 74 is restricted in the direction of correction (e.g. uniplanar screws). Additional bone anchor assemblies 72 may be used to extend the construct superiorly and/or inferiorly to the trauma anchors 550 as needed. Generally, polyaxial anchors may be preferred for the additional anchors, but any of fixed axis, uniplanar, and provisional locking screws, or any combination thereof, may also be used depending on the specific surgical needs. Additionally, a bone anchor assembly 2' may also be implanted in the fractured vertebrae, between the trauma anchors 2, 4. A polyaxial anchor may again be generally preferred when adding an anchor 2 between the trauma anchors, but any of fixed axis, uniplanar, and provisional locking screws may also be used depending on the specific surgical needs.

Figure 61:
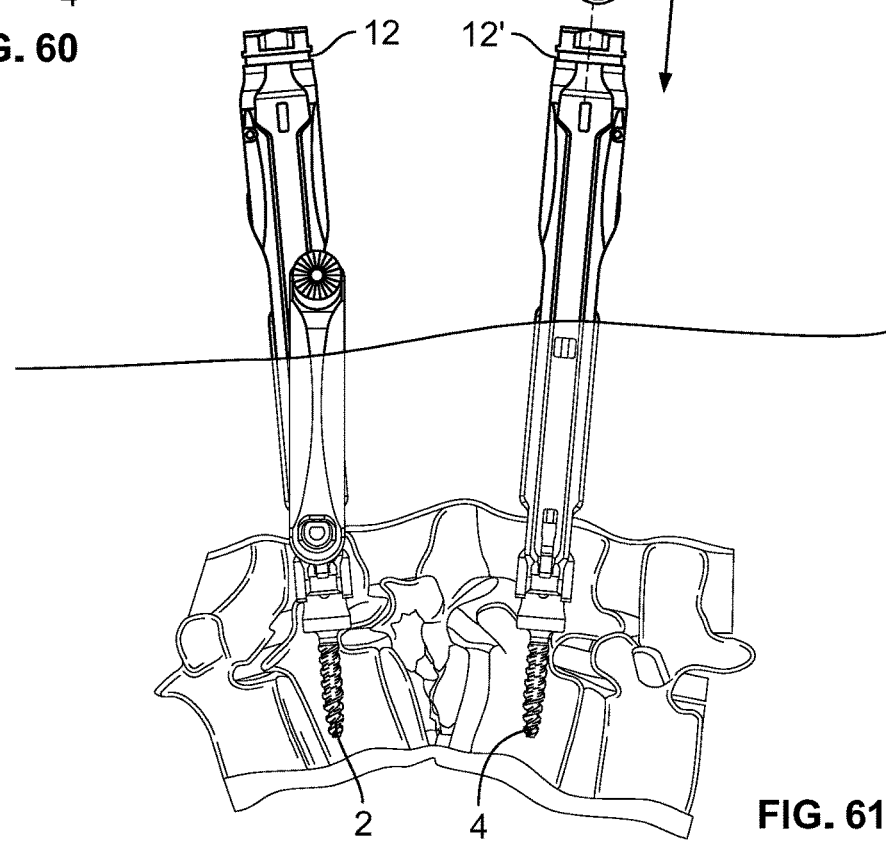
FIG. 61. An illustration of the embodiment of the system shown in FIG. 60, showing a first arm unit in place in a side track of the first guide member, and the arrow showing the introduction of a second arm unit into a side track of the second guide member.
Figure 62:
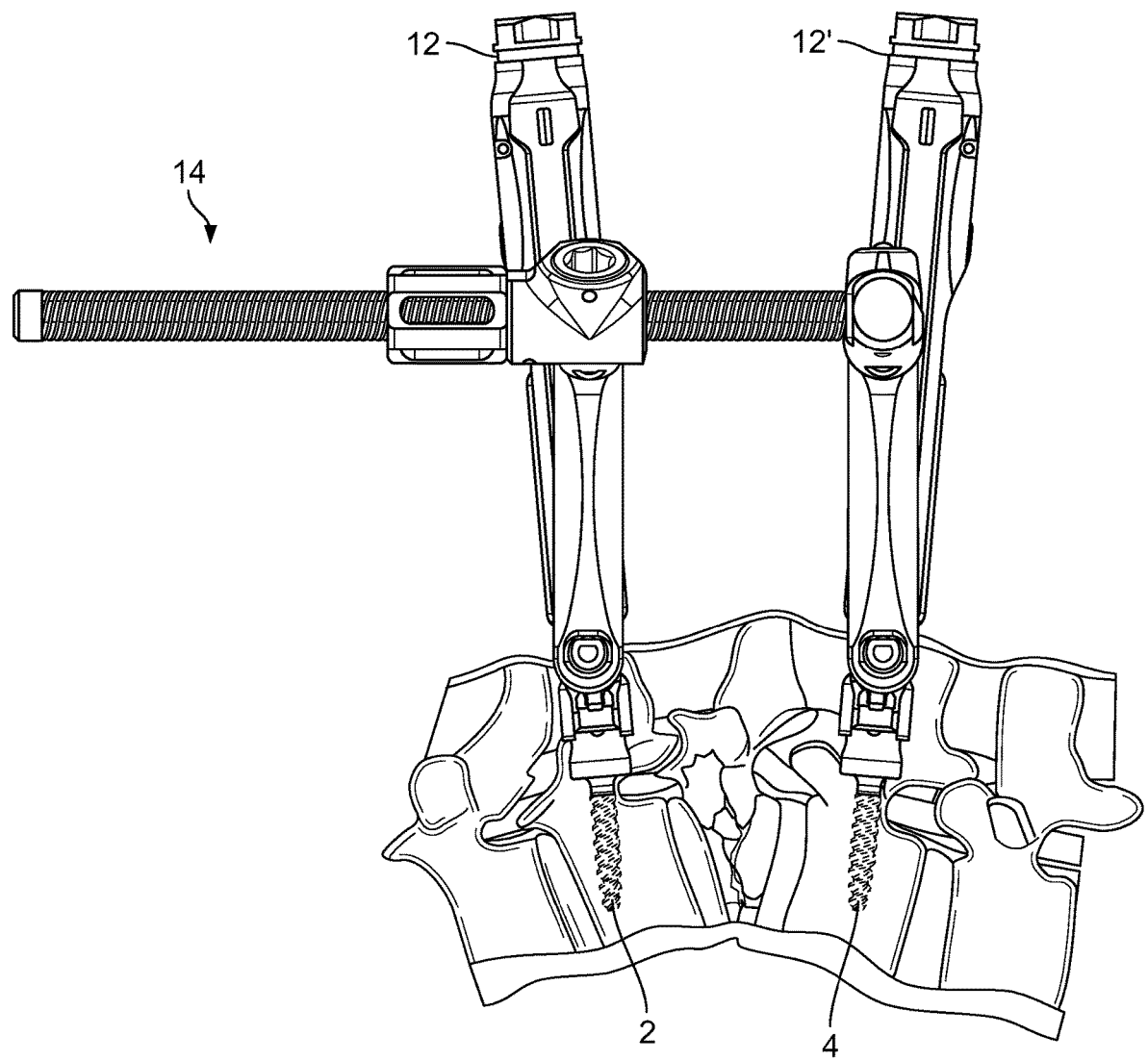
FIG. 62. An illustration of the embodiment of the system shown in FIGS. 60-61, with the pivot rack in place on the arm units.
Figure 63:
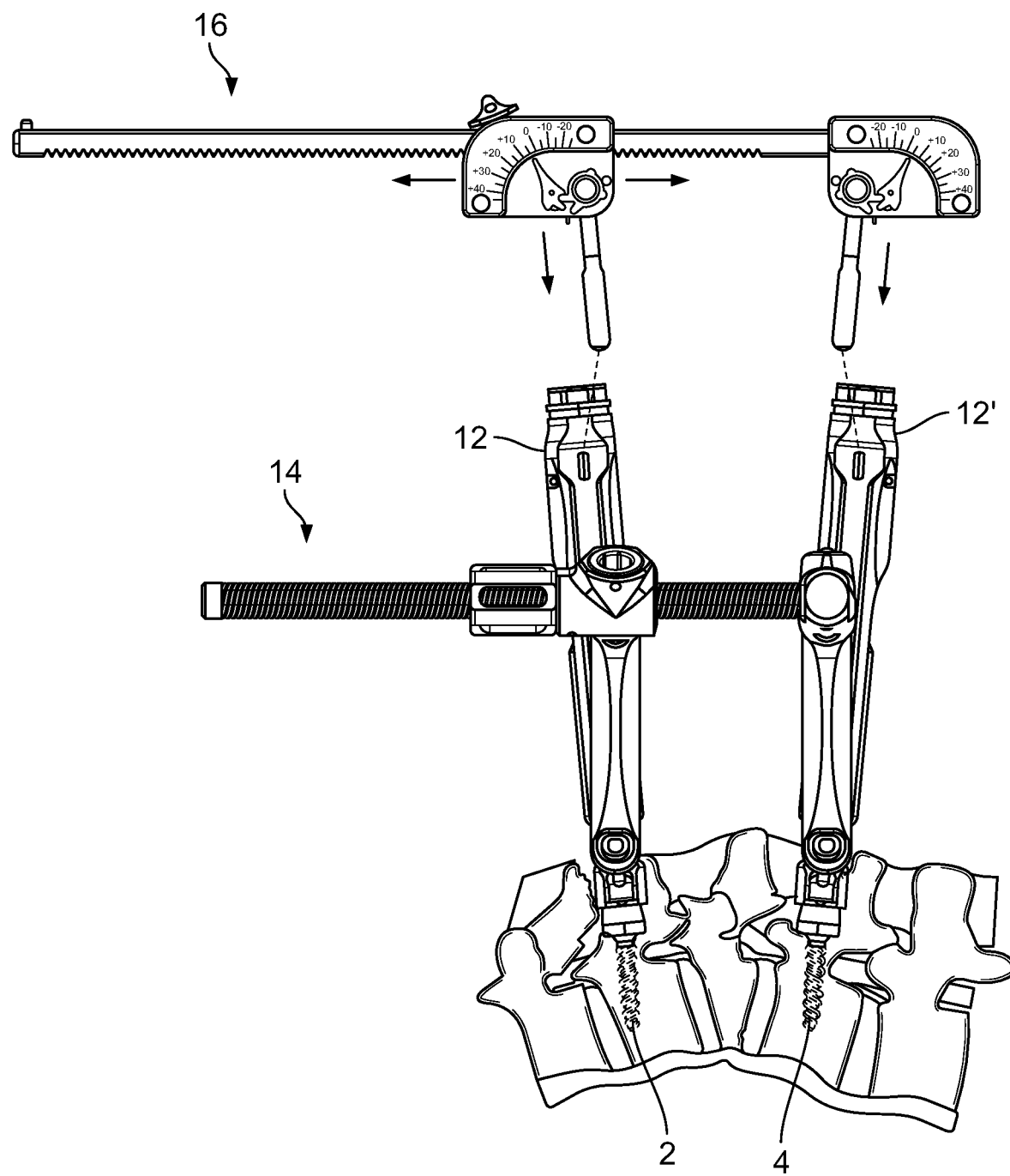
FIG. 63. An illustration of the embodiment of the system shown in FIGS. 60-62, showing an embodiment of the locking rack. Horizontal arrows show the sliding mobility of the second locking arm assembly along the elongated locking rack member. Verticals arrows show the introduction of the connector arms into the side tracks of the guide members.
Figure 64:
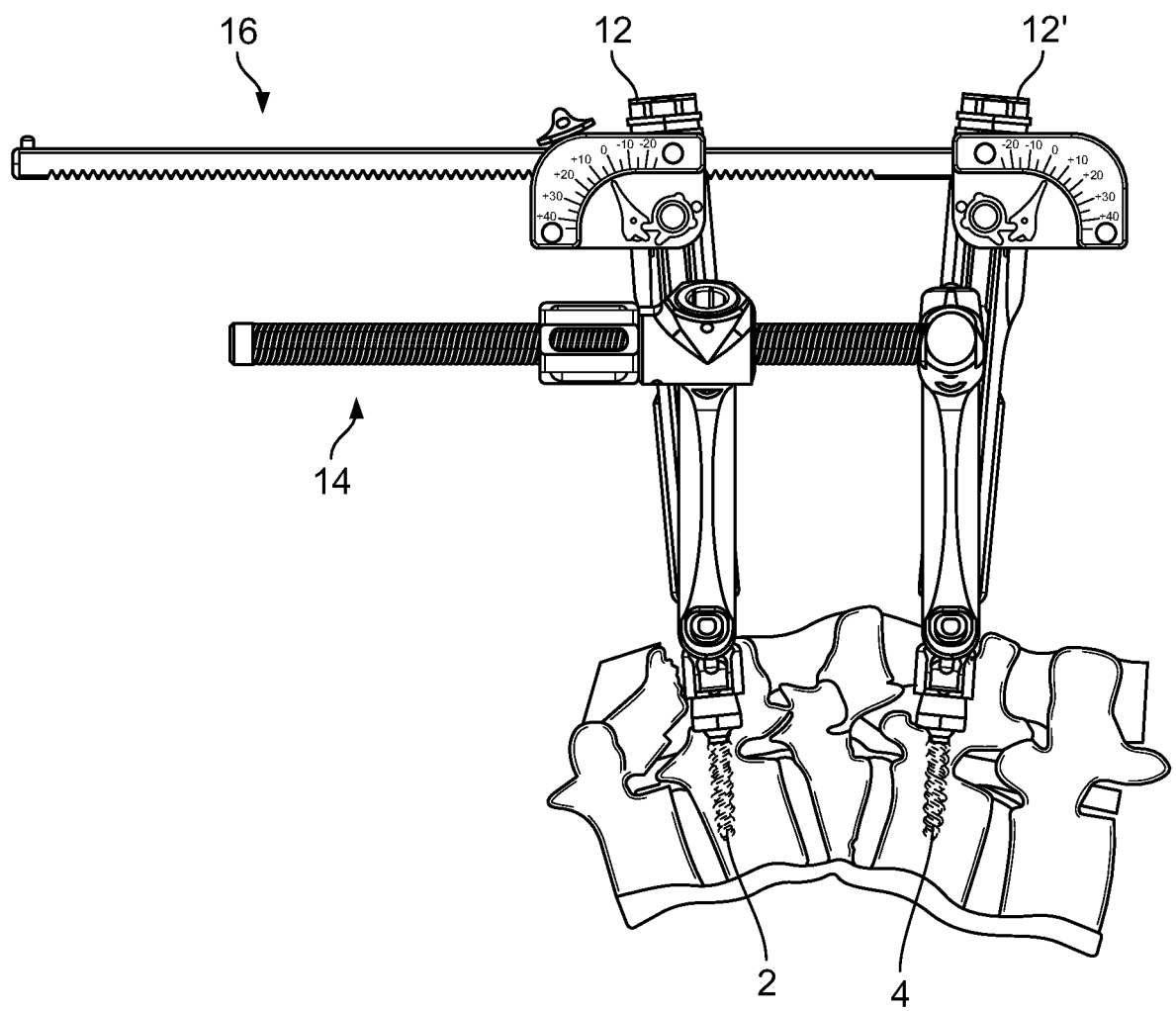
FIG. 64. An illustration of the embodiment of the system shown in FIGS. 60-63, with the locking rack in place.

The following steps for completing assembly of the fracture correction tool 600 and for imparting correction thereafter are described in the singular, that is, unilaterally along one side of the spine. However, it should be appreciated that one preferred method will occur bilaterally with a second correction tool 600' assembled in the same fashion as the first and used in tandem on the contralateral side. Now, with the bone anchor assemblies (trauma anchors) 2,4 implanted and the guide members 12, 12' extending from the patient, the pivot rack 14 is assembled (FIGS. 62-63). The appropriately sized pivot rack arm units 105 (e.g. long or short) are first selected. According to the presently described embodiment, this is accomplished using a visual indicator 340 on the guide members 12, 12'. The example indicator here being a laser mark in the form of an underlined "S" on the inside of the medial 47 and lateral 49 tracks. When the line under the "S" is visible above the skin line (FIG. 61) the short arms may be used, otherwise, the long arms should be used. To position the arm units 105, the distal attachment element 178 of the first arm unit 105 is engaged in one of the medial 47 and lateral side tracks 49 of the first guide member 12 and advanced distally until the distal attachment element 178 bottoms out in the side track 47, 49 and the locking element (such as shaped end 204) engages the corresponding locking element 570 of the guide member 12. The second arm unit 105 is coupled to the second guide member 12' in the same fashion (FIG. 61). The surgeon may choose to use the medial 47 or lateral side tracks 49 to position the pivot 14 and locking racks 16 to account for simple preference, differing patient anatomies, and the direction of rod passage, among other considerations. In the present example embodiment, when using the small arm units 105 the surgeon may choose to attach the locking rack 16 to the guide members 12, 12' 12 on either the same side or the opposing side as the pivot rack 14. When using the long arm units 105, the locking rack 16 will be placed on the side opposite the pivot rack 14.

With the arm units 105 locked in place, the guide members 12, 12' 12, 12' should be adjusted (if necessary) to align the rod slots 34 before assembling the pivot rack member 90 to the pivot rack arm units 105 by inserting the distal cavities 112, 164 of the first and second arm members 92, 94 onto the proximal attachment elements 176 of each arm unit 105, respectively. Prior to locking the orientation of the arm members 174 of the arm units 105, the arm members 92, 94 should be angulated towards or away from the midline of the rack 14 depending on the pathology being treated. For example, the arm members 92, 94 should be angulated towards the midline for burst or dislocation fractures to maximize distraction capabilities later in the procedure. Conversely, if treating a distraction "chance" fracture, the arm members 92, 94 should be angulated away from the midline to maximize compression capabilities later in the procedure. This can be achieved by adjusting the thumbwheel 150 on the pivot rack 14 by turning either clockwise or counterclockwise. Once the arm members are oriented appropriately, the arms 105 may be locked by tightening the locking pin 118, 170 on the pivot rack arm members 92, 94. Tightening the locking pin will engage the poker chip 190 of the proximal attachment member 176 with the corresponding poker chip 114, 166 of the arm members 92, 94 to lock the orientation of the arm members 92, 94 while locking the arm units 105 to the rack (FIG. 62).

The locking rack 16 is next engaged to the first and second guide members 12, 12' 12, 12' (FIG. 63). With the locking rack 16 in the unlocked configuration, the second arm assembly 94 is adjusted along the elongate locking rack member 210 until the spacing of the arm elements 290 matches that of the side tracks 46 (either medial 47 or lateral 49 as previously discussed) of the first and second guide members 12, 12' into which they will be advanced. The "triangle" marking 580 on the arm element 290 may be positioned between the "triangle" markings 585 flanking the associated side track 46 to help facilitate engagement. Once the triangles 580, 585 are aligned, the locking rack arm elements 290 are advanced down the respective side tracks 46 until the shoulders 303 bottom out on the side track ledges 305 and the gold levers "click" into place. Visual confirmation that the laser marked lines above the side tracks 46 on each guide members 12 are fully exposed above the locking rack engagements confirms that the locking rack 16 is properly seated. Leverage instruments 455, including handles 460 may be coupled to the proximal ends of the guide members 12, 12' to provide additional grip area and leverage to manipulate the guide members 12, 12' to achieve the desired correction (FIG. 65). According to one example, the handles 460 may be adjustable such that the handle 460 can extend straight in line with the longitudinal axis of the guide members 12, 12', or be adjusted to be angularly offset in either direction (i.e. cranially or caudally) from the longitudinal axis of the guide members 12, 12'. This allows for more clearance and additional leverage as the handles 455 are moved towards each other to apply corrective force.

Figure 66:
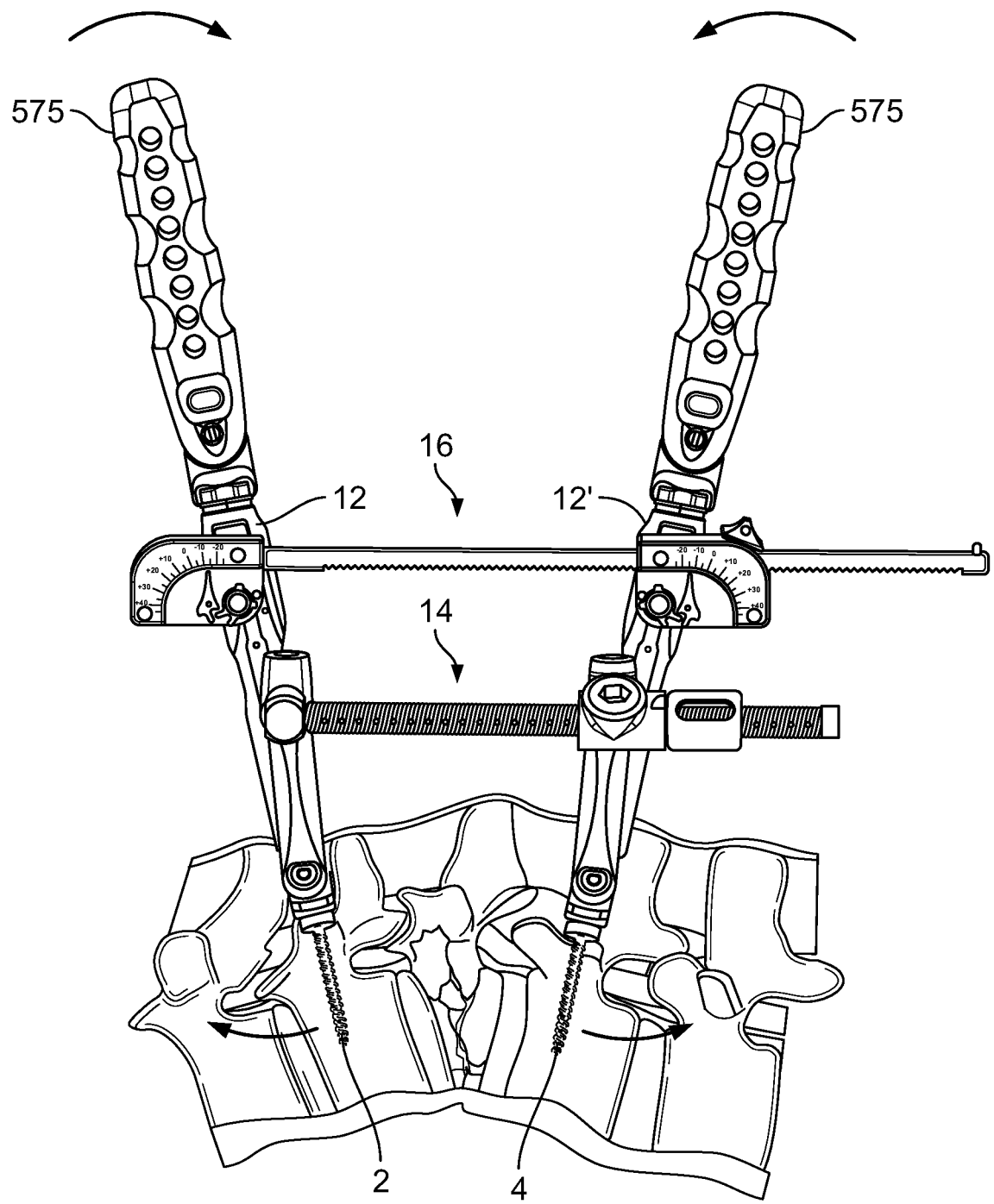
FIG. 66. An illustration of the embodiment of the system shown in FIGS. 60-65, with arrows illustrating the angulation of the guide members and dual driver and leverage instruments to achieve distraction of the injured site. The injured site is a compression or "burst" fracture in this example.
Figure 67:
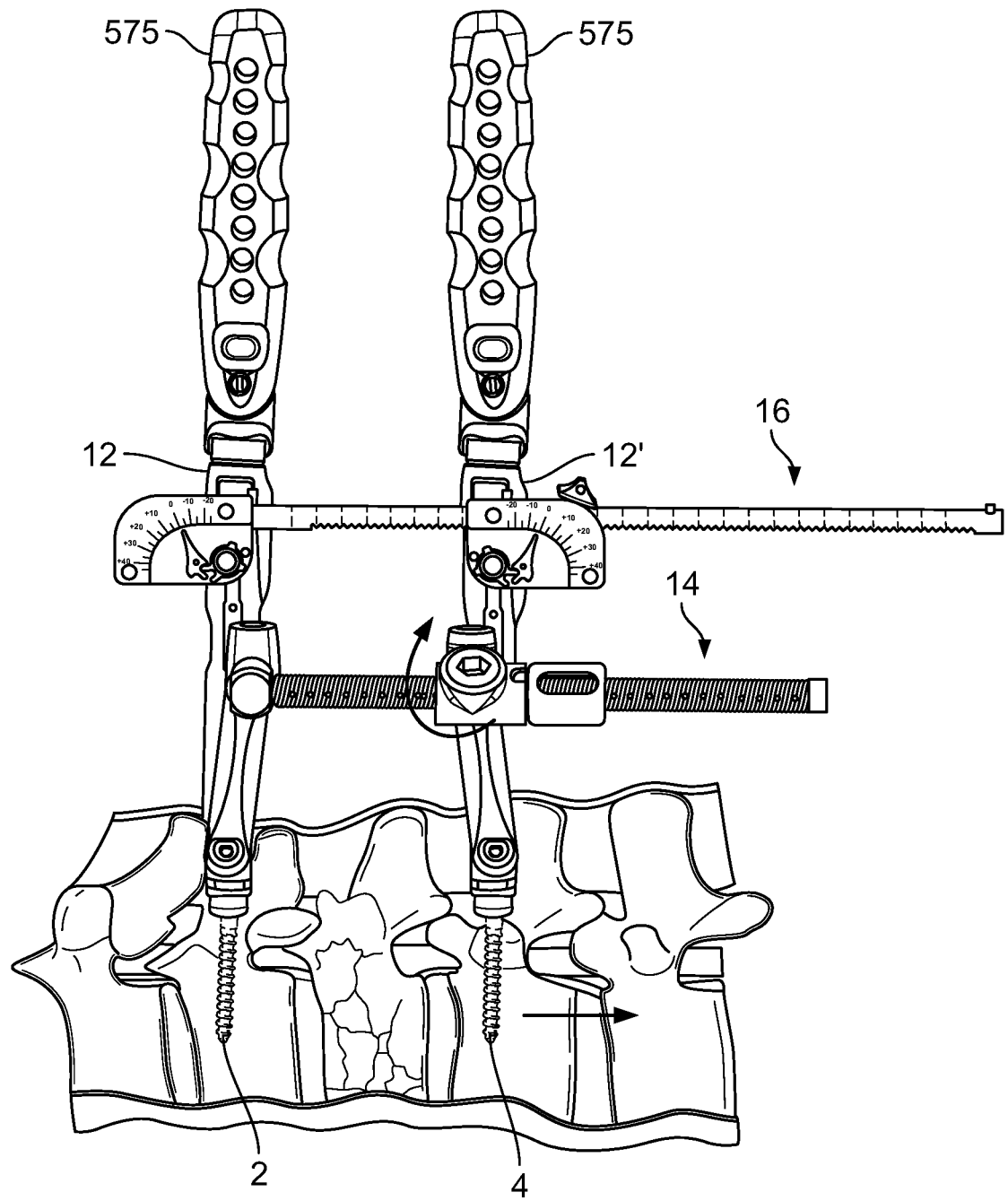
FIG. 67. An illustration of the embodiment of the system shown in FIGS. 60-66, post-angulation of the guide members. Note the corrected angulation of the vertebrae flanking the injured site. The arcuate arrow indicates the rotation of a driver engagement feature on the translation unit, causing the second pivot arm assembly translate away from the first pivot arm assembly. The horizontal arrow indicates the movement of the vertebra away from the injured site to achieve additional distraction without significant angulation.
Figure 68:
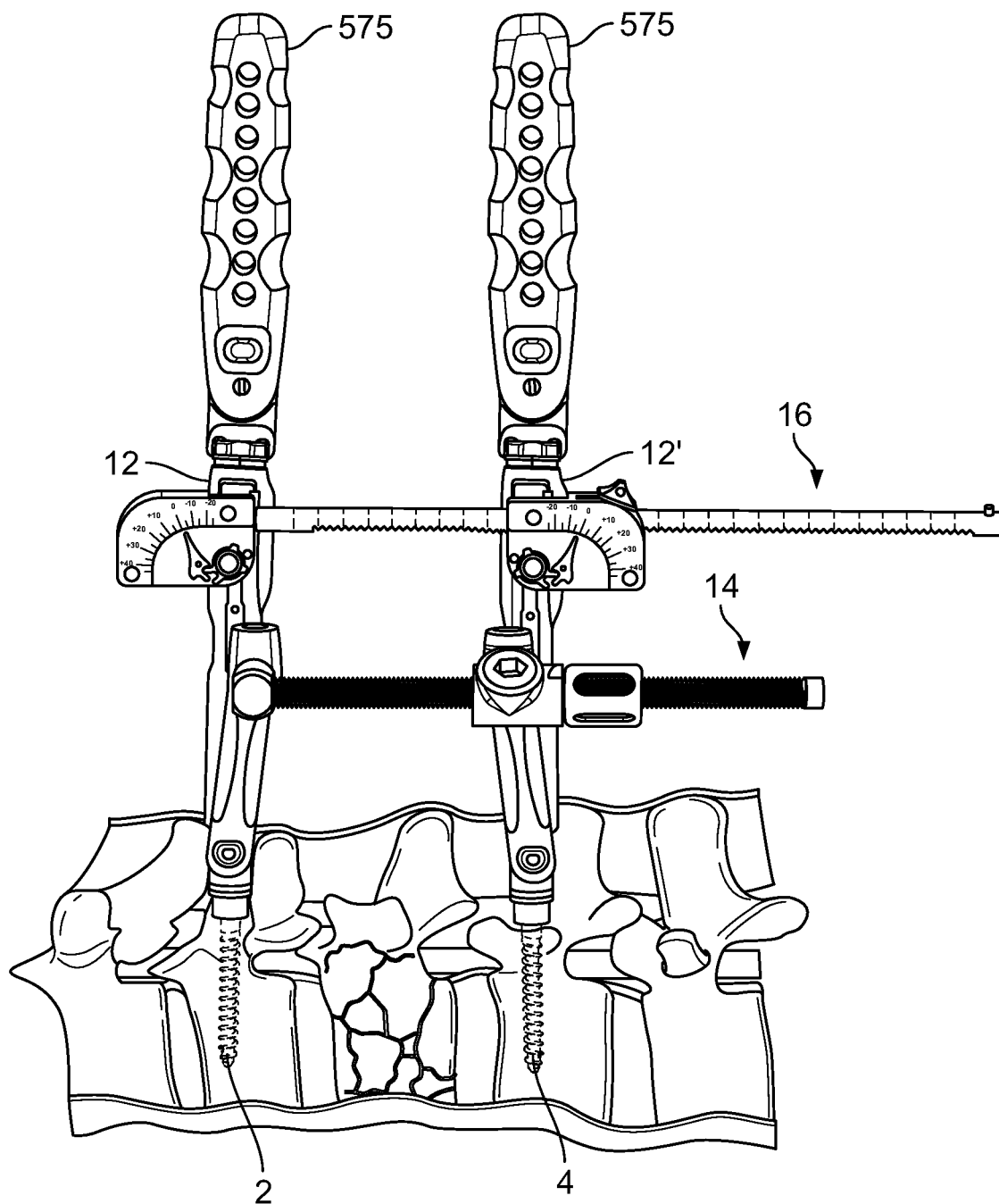
FIG. 68. An illustration of the embodiment of the system shown in FIGS. 60-66, post-translation of the pivot rack, showing further correction of the injured site.

With the fracture correction tool 10 assembled, corrective forces may be employed to reduce the fracture. The steps for achieving correction may vary depending on the type and severity of fracture. By way of example, correction of a compression or burst fracture is illustrated in FIGS. 66-68. When treating a compression or burst fracture the primary surgical goals are generally first to reduce the focal kyphosis back to anatomic alignment (e.g. lordosis) and then to achieve ligamentotaxis to move any retropulsion of bone in the canal back into the vertebral body. Accordingly, correction of the burst fracture begins with the application of angular force to rotate the vertebrae adjacent the fracture. To accomplish this, the locking rack toggle 282 should be adjusted to the locked position, engaging the passive unidirectional lock on the locking rack 16. The leverage instruments 455 and guide members 12, 12' are then manually pushed towards each other (towards the midline), causing the guide members 12, 12' to rotate about the pivot point formed by the pivot rack 14 adjacent the anchor guide members 12 12' interface. Thus, the bone anchor assemblies 2, 4 coupled to the distal end of the guide members 12, 12' rotate outwards (away from the midline) as the proximal ends of the guide members 12, 12' converge, thereby providing corrective angulation to the vertebrae in which the anchors 2, 5 are implanted (FIG. 66). The passive lock of the locking rack 16 allows the guide members 12, 12' to converge but prevents movement in the opposite direction such that the applied correction is maintained by the locking rack 16. This not only simplifies the process of locking in the correction (e.g. eliminating the need for a second user to lock a rod 6 to the anchors 2, 4 while the first manually users holds the correction) but also allows the correction to be dialed in incrementally and precisely. Fluoroscopy (or other suitable imaging/assessment tools) may be used as needed to monitor the correction until the desired correction/alignment has been achieved. With the proper alignment restored, distraction may be applied through the pivot rack 14 to create ligamentotaxis. The drive feature 162 may be rotated in the appropriate direction (e.g. clockwise) to cause the arm assembly 94 to migrate away from the arm assembly 92 along the elongated rack member 90, increasing the distance between the bone anchor assemblies 2, 4 (FIG. 67). Preferably, distraction may be applied incrementally, switching back and forth between the two sides of the bilateral construct to facilitate even bilateral distraction. Markings on the elongated locking rack member 90 may also provide an indication of the arm travel distance to further facilitate even distraction across the bilateral construct. Fluoroscopy (or other suitable imaging/assessment tools) may again be used as needed during distraction to monitor and assess the correction achieved. Once the desired correction is achieved (FIG. 68) a rod 6 may be inserted and locked to the anchors 2 to hold the correction while the bone heals, as will be described further below.

Figure 69:
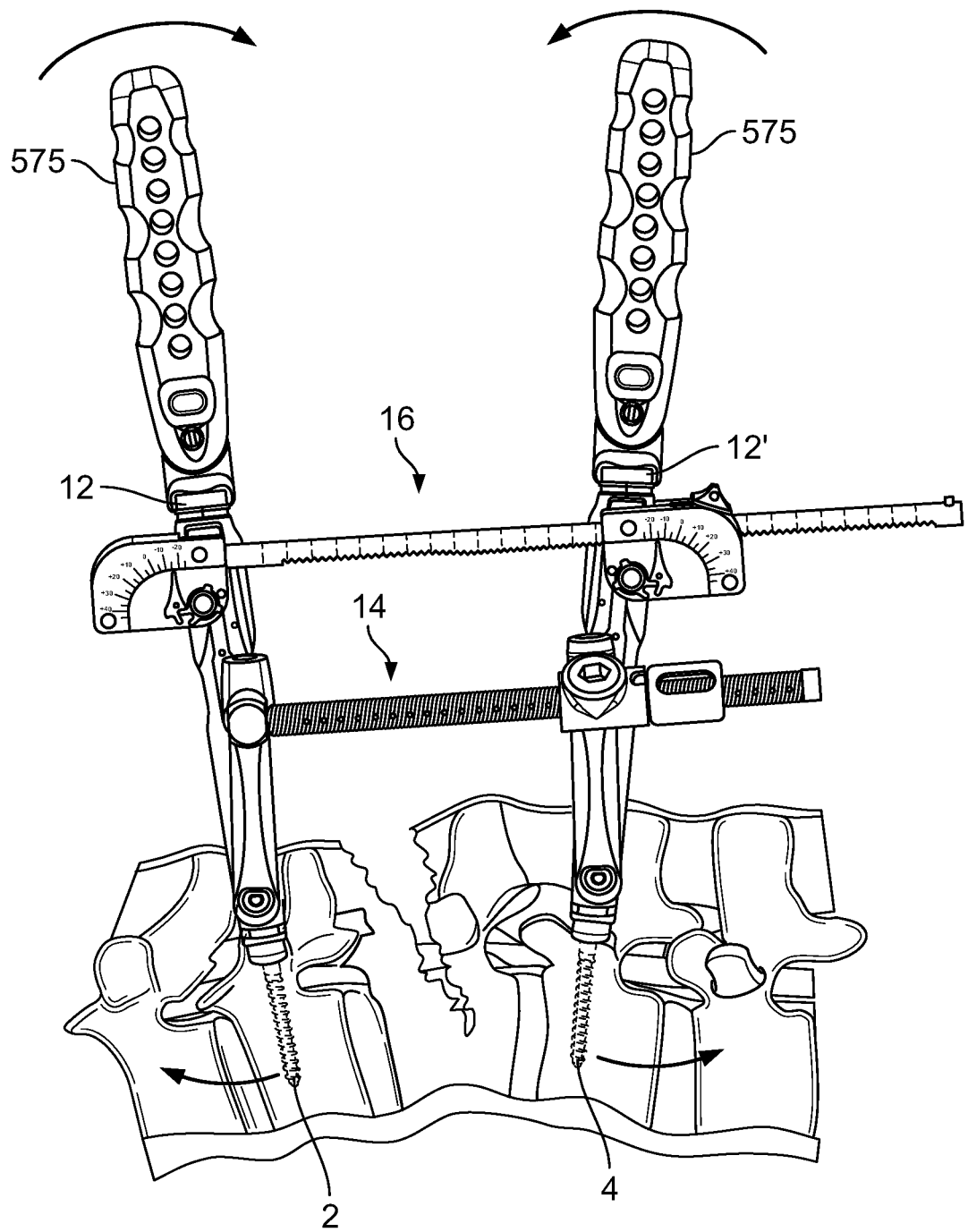
FIG. 69. An illustration of an embodiment of the system in place, anchored to vertebrae flanking a distraction or "chance" fracture, with arrows illustrating the angulation of the guide members and dual driver and leverage instruments to achieve distraction of the injured site. As shown, the handles and guides are manually pushed towards each other, causing the guides to rotate about the pivot point formed by the pivot rack adjacent the anchor/guide interface, and thereby rotating the bone anchors outwards (away from the midline) providing corrective angulation to the vertebrae in which the anchors are implanted.
Figure 70:
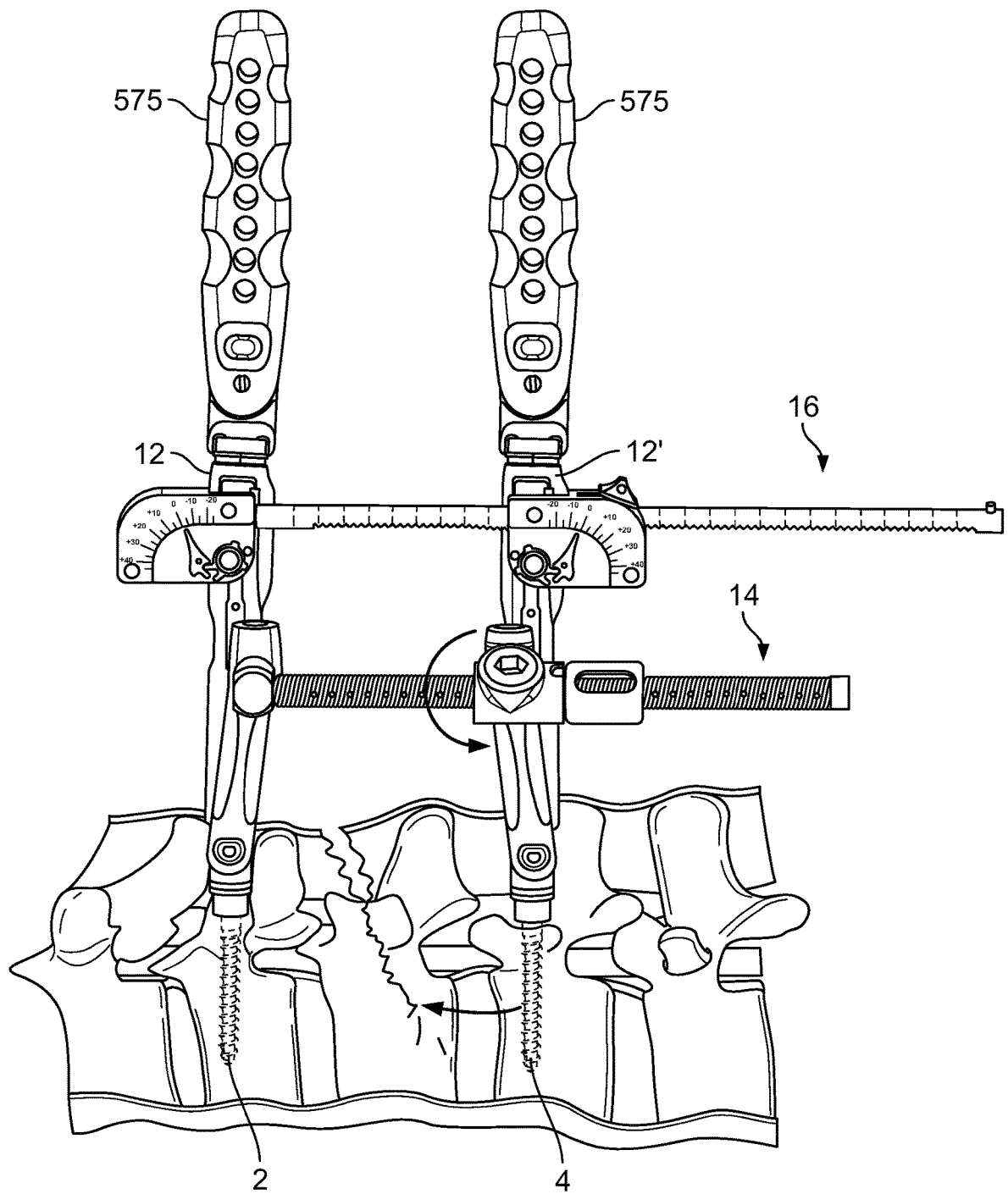
FIG. 70. An illustration of the embodiment of the system shown in FIG. 60-69 post-angulation of the guide members. The arcuate arrow shows the rotation of the drive feature to cause the second arm unit to migrate towards the first arm unit along the elongate pivot rack member, decreasing the distance between the bone anchors.
Figure 71:
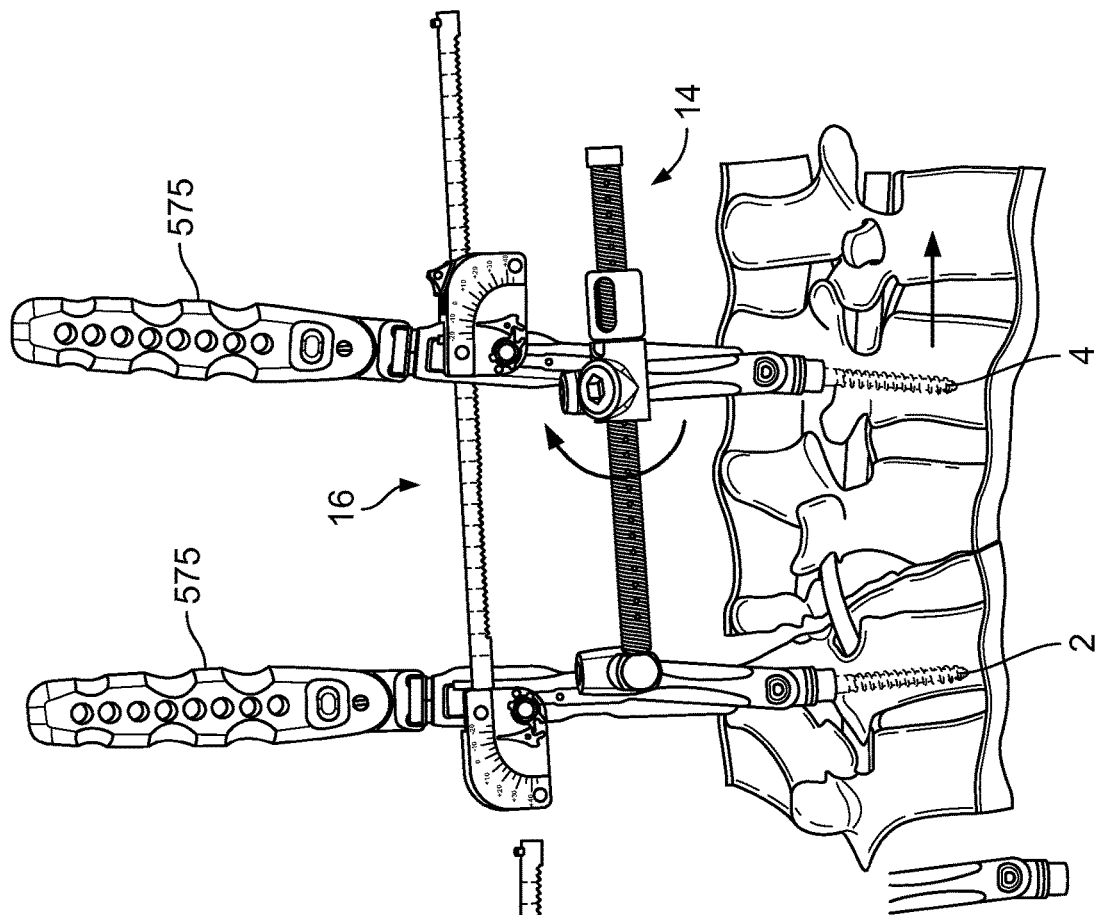
FIG. 71. An illustration of the embodiment of the system shown in FIGS. 69-70, post-translation of the pivot rack, showing further correction of the distraction fracture.

Now, with reference to FIGS. 69-71, the trauma to be corrected may be a distraction "chance" fracture. When treating a chance fracture the primary goals are generally first to reduce the posterior kyphosis back to anatomic alignment (e.g. lordosis) and then compress the posterior elements back into anatomic alignment. Accordingly, correction of the chance fracture begins with the application of angular force to rotate the vertebrae adjacent the fracture into alignment. To accomplish this, the locking rack toggle 282 should be adjusted to the locked position, engaging the passive unidirectional lock on the locking rack 16. The leverage instruments 455 and guide members 12, 12' are then manually pushed towards each other (towards the midline), causing the guide members 12, 12' to rotate about the pivot point formed by the pivot rack 14 adjacent the anchor/guide members interface, and thereby rotating the bone anchor assemblies 2, 4 outwards (away from the midline) providing corrective angulation to the vertebrae in which the anchors are implanted (FIG. 69). The passive lock of the locking rack 16 allows the guide members 12, 12' to converge but prevents movement in the opposite direction such that the applied correction is maintained by the locking rack 16. Fluoroscopy (or other suitable imaging/assessment tools) may be used as needed to monitor the correction until the desired correction/alignment has been achieved. With the proper alignment restored, compression may be applied through the pivot rack 14 to draw the posterior elements together and bringing the fracture back to anatomic alignment. The drive feature 162 may be rotated in the appropriate direction (e.g. counterclockwise) to cause the arm member 94 to migrate towards the arm member 92 along the elongate rack member 90, decreasing the distance between the bone anchor assemblies 2 (FIG. 70). Preferably, compression may be applied incrementally, switching back and forth between the two sides of the bilateral construct to facilitate even bilateral compression. Markings on the rack member 90 may also provide an indication of the arm travel distance to further facilitate even compression across the bilateral construct. Fluoroscopy (or other suitable imaging/assessment tools) may be used as needed during compression to monitor and assess the correction achieved. Once the desired correction is achieved (FIG. 71) a rod 6 may be inserted and locked to the anchors 2 to hold the correction while the bone heals, as will be described further below.

Figure 72:
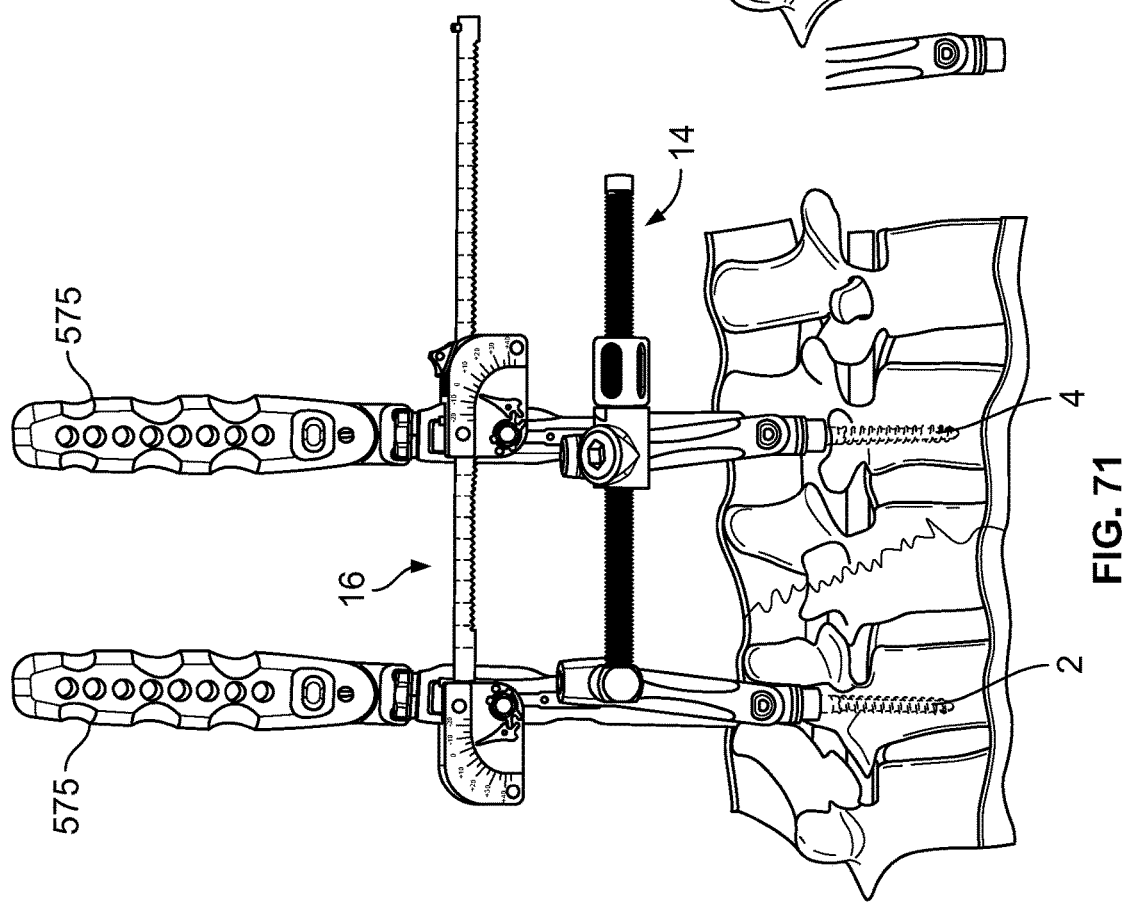
FIG. 72. An illustration of an embodiment of the system in place, anchored to vertebrae flanking a dislocation fracture. The arcuate arrow shows rotation of the drive feature to cause the arm unit to migrate away from the other arm unit along the elongate pivot rack member, increasing the distance between the bone anchors to move the vertebral bodies into positional alignment and to create ligamentotaxis (horizontal arrow).
Figure 74:
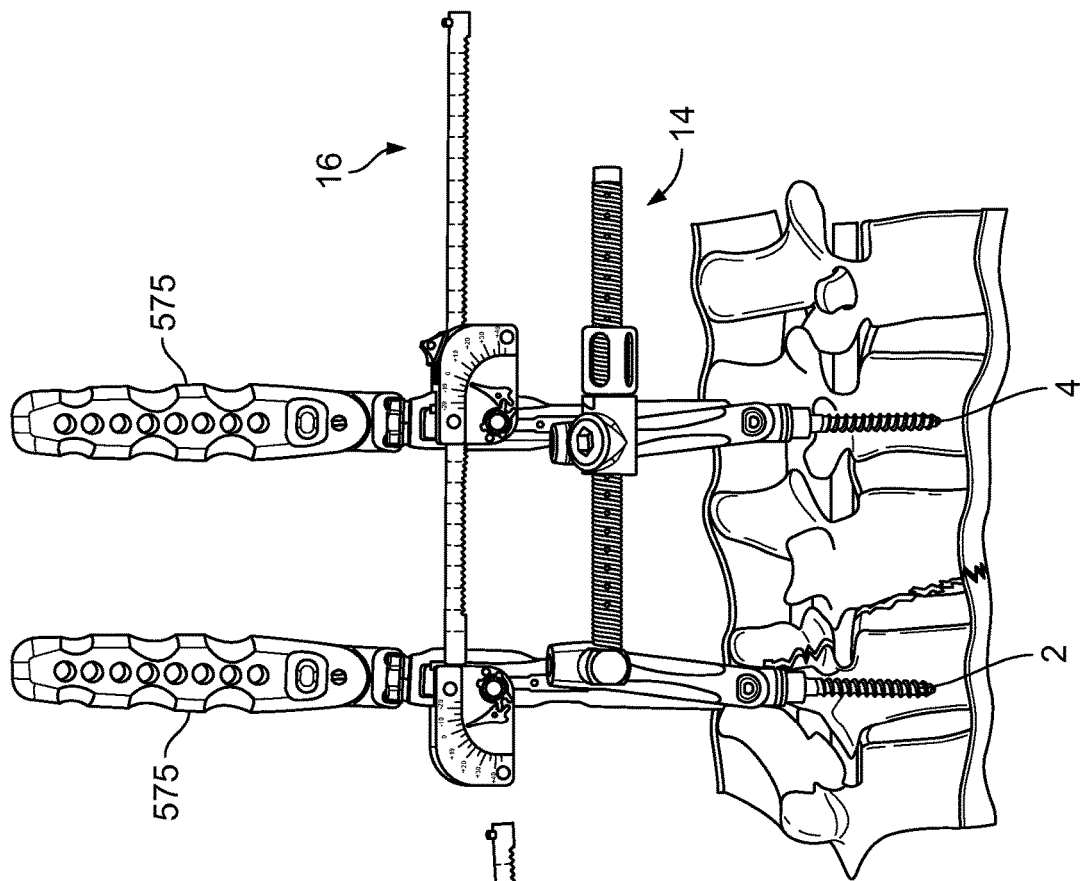
FIG. 74. An illustration of the embodiment of the system shown in FIGS. 72-73, showing correction of the alignment at the injured site.
Figure 73:
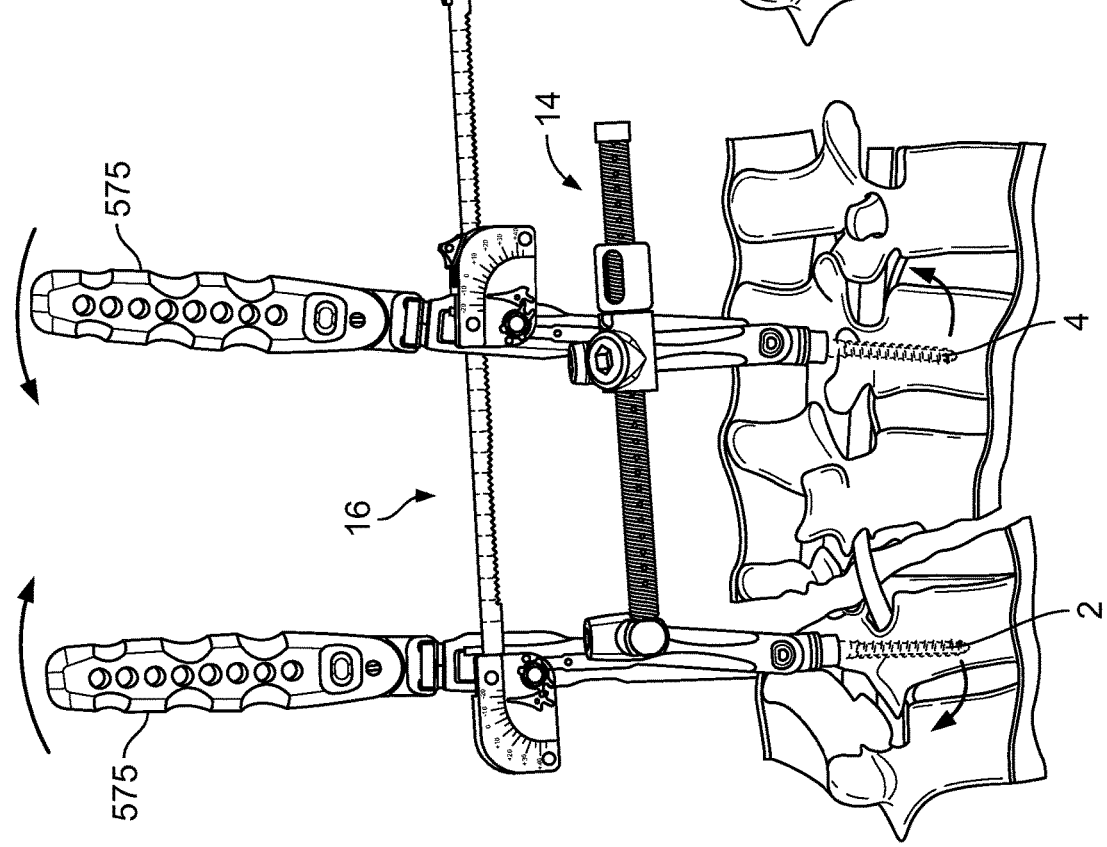
FIG. 73. An illustration of the embodiment of the system shown in FIG. 72, with arrows illustrating the angulation of the guide members and dual driver and leverage instruments to achieve distraction of the injured site. The handles and guides are manually pushed towards each other, causing the guides to rotate about the pivot point formed by the pivot rack adjacent the anchor/guide interface, and causing the bone anchors coupled to the distal end of the guides rotate outwards (away from the midline) as the proximal ends of the guides converge, thereby providing corrective angulation to the vertebrae in which the anchors are implanted.

Referring now to FIGS. 72-74, the trauma to be corrected may be a dislocation fracture. When reducing a dislocation fracture the primary surgical goals are generally to first move the affected vertebral body(s) back to anatomic alignment (jumped facets), and then to reduce the focal kyphosis back to anatomic alignment (e.g. lordosis). Accordingly, correction of the dislocation fracture begins with the application of distraction across the construct to move the vertebral bodies into positional alignment and to create ligamentotaxis. To accomplish this, the drive feature 162 may be rotated in the appropriate direction (e.g., clockwise) to cause the pivot arm assembly 94 to migrate away from the pivot arm assembly 92 along the elongated pivot rack member 90, increasing the distance between the bone anchor assemblies 2, 4 (FIG. 72). Preferably, distraction may be applied incrementally, switching back and forth between the two sides of the bilateral construct to facilitate even bilateral distraction. Markings on the elongated pivot rack member 90 may also provide an indication of the arm travel distance to further facilitate even distraction across the bilateral construct. Fluoroscopy (or other suitable imaging/assessment tools) may be used as needed during distraction to monitor and assess the correction achieved. Once the positional alignment of the vertebrae is restored, angular correction may be applied to reduce the focal kyphosis back to a more natural alignment (e.g. lordosis). The locking rack toggle 282 should be adjusted to the locked position, engaging the passive unidirectional lock on the locking rack 16. The handles 460 and guide members 12, 12' are then manually pushed towards each other (towards the midline), causing the guide members 12, 12' to rotate about the pivot point formed by the pivot rack 14 adjacent the anchor/guide members 12 interface. Thus, the bone anchor assemblies 2 coupled to the distal end of the guide members 12, 12' rotate outwards (away from the midline) as the proximal ends of the guide members 12, 12' converge, thereby providing corrective angulation to the vertebrae in which the anchors 2 are implanted (FIG. 73). The passive lock of the locking rack 16 allows the guide members 12, 12' to converge but prevents movement in the opposite direction such that the applied correction is maintained by the locking rack 16. Fluoroscopy (or other suitable imaging/assessment tools) may be used as needed to monitor the correction until the desired correction/alignment has been achieved (FIG. 74).

Once the desired correction has been achieved using the fracture correction tool 10, a rod 6 is inserted and locked to the bone anchor assemblies 2, 4 to fix their position, and the position of the vertebrae to which they are attached, while new bone forms to heal the fracture. Indicators on the locking rack 16 provide information to aid in the selection of an appropriately sized and/or bent rod 6. For example, rod length may be determined by adding the length shown in the viewing aperture 278 (corresponding to the distance between the vertical reference lines where the locking rack 16 couples to each guide members 12, 12') to the length shown on each of the left and right markings panel 244 (corresponding to the distance between the respective screw housing and the vertical reference line) to calculate the point-to-point distance between the two screw housings. The markings panel 244 have green or red markings to indicate a positive or negative value to ensure lengths are added (or subtracted) appropriately. To determine rod angle, the length measurement on the left and right markings panels 244 are each divided by 2 and then added together. With this information the surgeon may then add or subtract length and bend angles as necessary to account for lordosis. A rod measurement software program or mobile app may be provided to further simplify the rod measurement calculations. Alternatively, or in addition, where computer aided surgery ("CAS") tools are available, CAS may be deployed to generate rod cutting and bending instructions to custom fit the rod 6 to the construct. In another alternative, a temporary measurement rod may be coupled to the rod inserter and pass through the guide members 12, 12' at each level of the construct. Using fluoroscopy windows in the rod, an estimated rod length can be measured. If the construct 10 extends more than two levels above or below the fracture level, the temporary rod measurement rod may be inserted from the superior end of the construct 10 to the fracture and again from the inferior end of the construct to the fracture. The measured lengths are then added together to calculate the total distance from which the desired rod length can be determined.

Figure 75:
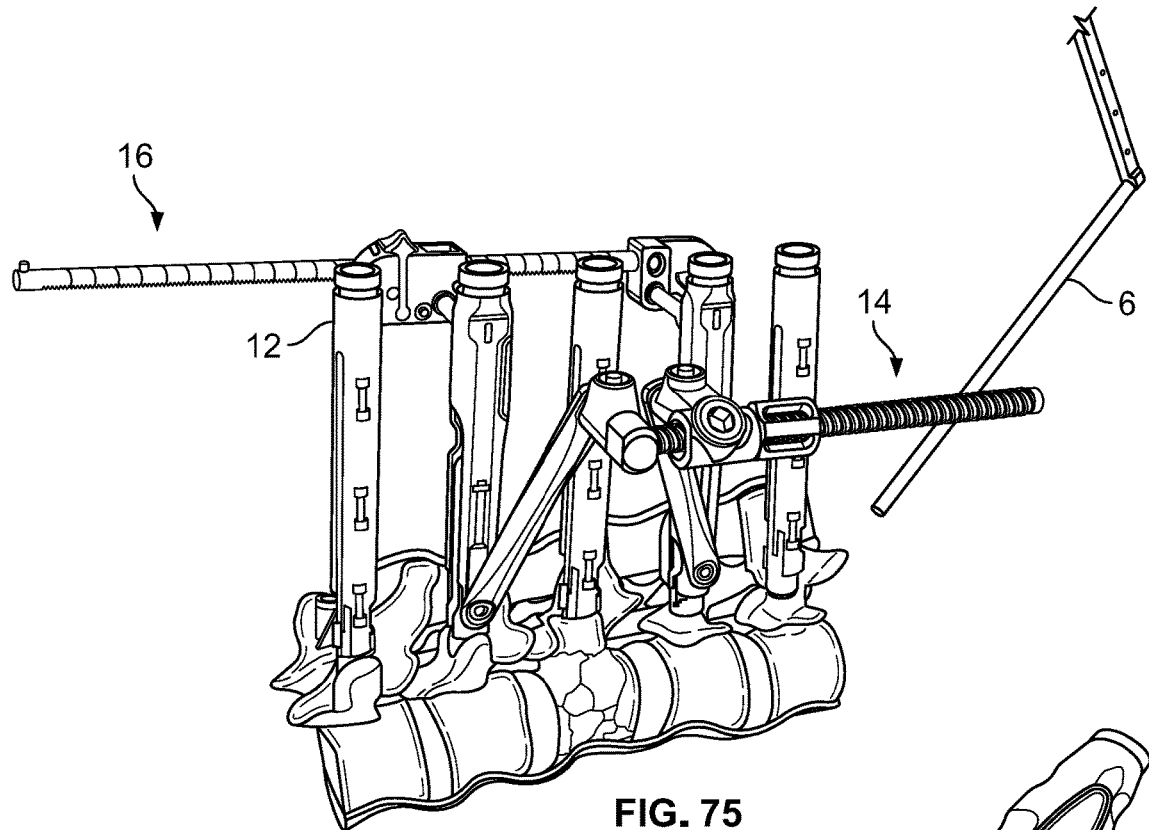
FIG. 75. An illustration of an embodiment of the system in place in four vertebrae, after correction of a fracture. An embodiment of a spinal rod and a spinal rod insertion tool is shown.
Figure 76:
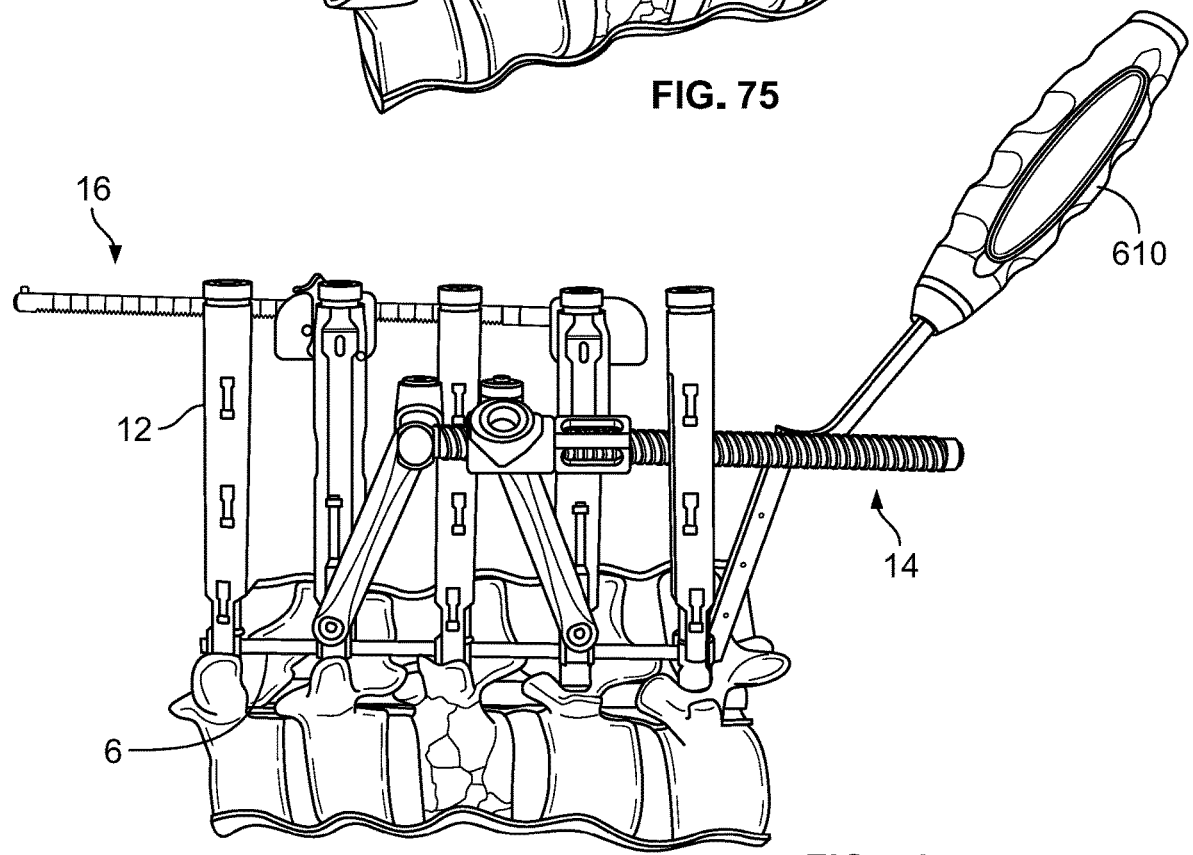
FIG. 76. An illustration of the embodiment of the system shown in FIG. 75, with the rod in place in the housings of the pedicle screws.
Figure 77:
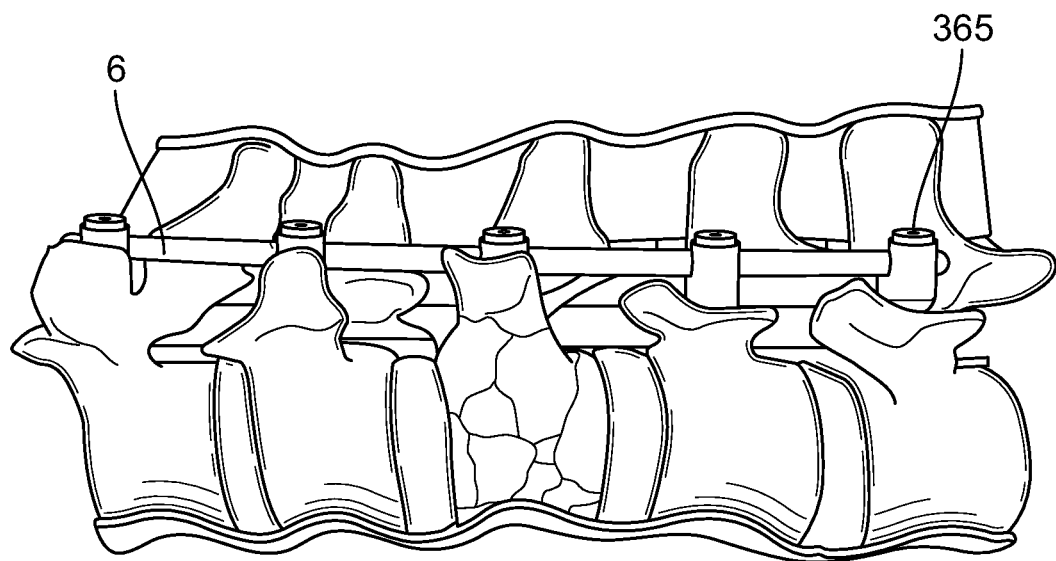
FIG. 77. An illustration of the embodiment of the system shown in FIGS. 75-76, after removal of the guide members and the two racks, leaving behind the pedicle screws and the spinal rod.
Figure 78:
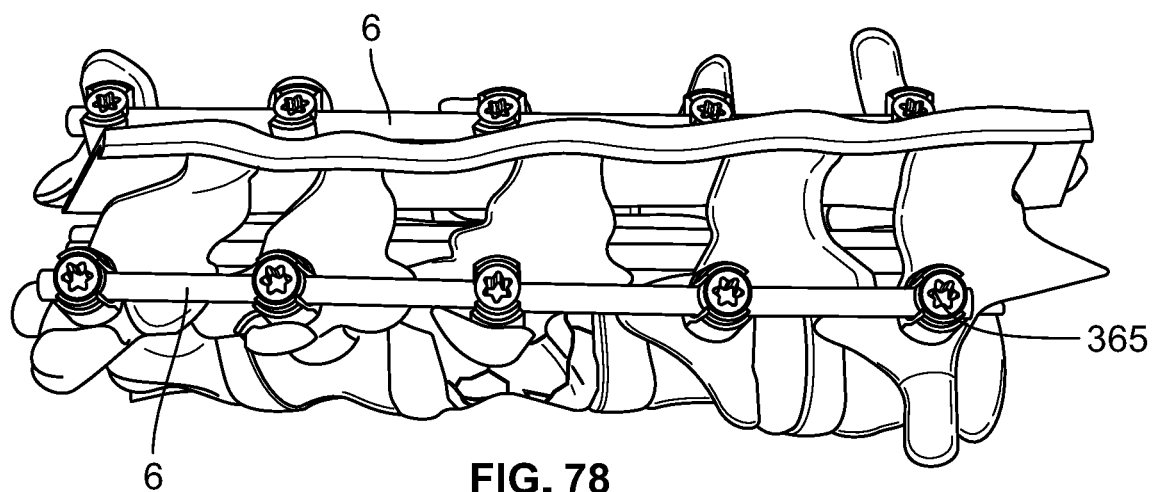
FIG. 78. A perspective view of the embodiment of the system shown in FIGS. 75-76, after removal of the guide members and the two racks, showing bilateral components.

The rod 6 is selected and is next inserted through the rod slots in the guide members 12, 12' and into the rod housings 74 of the bone anchor assemblies 2. This is depicted in FIGS. 75-76 with a construct which is extended an additional level both inferiorly and superiorly to the trauma anchors 2, 4 and also includes an anchor 2' at the fracture level. If needed, a reduction tool (not shown) configured to engage with the guide members 12, 12' may be employed to fully reduce the rod 6 into one or more of the housings 74. The reducer is further configured to be deployed through the interior of the guide members 12 12' such that the ability to reduce the rod 6 is not inhibited by the coupling of the locking 16 and/or pivot 14 racks. Preferably the reducer may also be used to engage lock screws 365 in the housing 74 to capture the rod 6. A separate lock screw driver (not shown) may be used to deliver lock screws 365 to anchors 2 where the reduction tool was not used. Final tightening of the lock screws 365 to a selected torque is performed to complete the construct 10. Thereafter, the pivot rack 14, locking rack 16, and guide members 12, 12' of the fracture correction tool 10 are removed and the incision(s) are closed. The final bilateral construct (FIGS. 77-78) fixes the vertebrae in their corrected positions while new bone growth occurs to heal the fracture. Once healing of the fracture is complete the surgeon may choose to perform another procedure to remove the rod 6 and anchors 2, 4. This may be desirable for example, where the fracture reduction was performed without additionally fusing the vertebrae across the disc space. Where fusion is performed it may instead be more desirable to leave the hardware in place.

Alternative embodiments of the method are also contemplated using only one of the racks 14, 16. For example, the pivot rack 14 may be used without the locking rack 16. The pivot rack 14 is capable of causing distraction and compression without the locking rack in place. In such embodiments the rod may be emplaced prior to distraction or compression, and then promptly reduced once distractor or compression has been achieved.

The foregoing description illustrates and describes the processes, machines, manufactures, compositions of matter, and other teachings of the present disclosure. Additionally, the disclosure shows and describes only certain embodiments of the processes, machines, manufactures, compositions of matter, and other teachings disclosed, but, as mentioned above, it is to be understood that the teachings of the present disclosure are capable of use in various other combinations, modifications, and environments and are capable of changes or modifications within the scope of the teachings as expressed herein, commensurate with the skill and/or knowledge of a person having ordinary skill in the relevant art. The embodiments described hereinabove are further intended to explain certain best modes known of practicing the processes, machines, manufactures, compositions of matter, and other teachings of the present disclosure and to enable others skilled in the art to utilize the teachings of the present disclosure in such, or other, embodiments and with the various modifications required by the particular applications or uses. Accordingly, the processes, machines, manufactures, compositions of matter, and other teachings of the present disclosure are not intended to limit the exact embodiments and examples disclosed herein. Any section headings herein are provided only for consistency with the suggestions of 37 C.F.R. .sctn. 1.77 or otherwise to provide organizational queues. These headings shall not limit or characterize the invention(s) set forth herein.

The invention claimed is:

1. A system comprising:
a bone anchor assembly; and
a guide member, having a longitudinal axis, for positioning and angulating the bone anchor assembly, the guide member comprising:
a proximal end and a distal end,
a lumen extending from the proximal end to the distal end,
a pair of opposed longitudinal rod slots opening to the distal end and extending proximally for a length along the guide member and contiguous with the lumen, to form a rod channel dimensioned to guide a spinal rod into the bone anchor assembly;
a bone anchor engagement feature at the distal end; and
a side track extending longitudinally between the pair of opposed longitudinal rod slots,
wherein the side track is configured to receive a guide member attachment feature of a pivot rack, wherein the guide member attachment feature has a broad portion and a narrower portion to allow the guide member attachment feature to be freely slid in the side track while constrained from moving radially with regard to the guide member, and
wherein the guide member is configured to rotate around a rotation axis perpendicular to the longitudinal axis when the guide member attachment feature is seated in the side track.

2. The system of claim 1, wherein the side track comprises an elongated lip element partially overhanging an indented surface, the side track configured to slideably receive a shim therein.

3. The system of claim 2, wherein the side track comprises a shim restraining feature configured to interact with the shim to temporarily restrain the shim from sliding in the side track.

4. The system of claim 2, wherein the indented surface comprises a plurality of apertures configured to secure a rack to the guide assembly.

5. The system of claim 1, wherein the guide member further comprises a second side track extending longitudinally between the pair of opposed longitudinal rod slots.

6. The system of claim 1, wherein the guide member further comprises an instrument engagement feature at a proximal end of the side track.

7. The system of claim 1, wherein the guide member further comprises an outer sleeve and a pair of inner arm members positioned within the outer sleeve, wherein the pair of inner arm members are configured to releasably engage a housing of the bone anchor assembly.

8. The system of claim 7, wherein the pair of inner arm members are moveable between a locked position and an unlocked position, wherein in the unlocked position the arm members are not engaged with the bone anchor assembly, and wherein in the locked position the arm members are fixedly engaged with the bone anchor assembly.

9. The system of claim 7, wherein each arm member of the pair of inner arm members comprises an elongated partially-cylindrical member having a distal end configured to engage the housing of the bone anchor assembly.

10. The system of claim 7, wherein the outer sleeve is a generally tubular member having a proximal end, a distal end, and a lumen extending longitudinally through the outer sleeve.

11. The system of claim 1, further comprising a locking rack indicator pattern inscribed at a proximal end of the side track to indicate when an arm element of a locking rack is properly aligned to be slid into the side track.

12. The system of claim 1, further comprising a pivot rack indicator pattern positioned on the guide member.

13. The system of claim 1, further comprising an incision depth indicator pattern inscribed on the side track and generally perpendicular to a longitudinal axis of the guide member.

14. The system of claim 1, wherein the bone anchor assembly comprises a bone anchor configured to engage bone, and a housing configured to couple to the bone anchor and engage the spinal rod.

15. The system of claim 14, wherein the housing of the bone anchor assembly comprises:
  a base configured to mate with the bone anchor;
  a pair of arms separated by a rod channel configured to receive the spinal rod therein; and
  an attachment groove configured to engage the bone anchor engagement feature of the guide member.

16. The system of claim 15, further comprising a lock screw configured to engage the housing of the bone anchor assembly and lock the spinal rod therein.

17. The system of claim 16, wherein the lock screw is configured to threadably engage the pair of arms to lock the spinal rod therein.

18. The system of claim 1, further comprising the pivot rack.

19. A guide member for positioning and angulating a bone anchor assembly, the guide member comprising:
  a proximal end and a distal end;
  a lumen extending from the proximal end to the distal end;
  a pair of opposed longitudinal rod slots opening to the distal end and extending proximally for a length along the guide member and contiguous with the lumen, to form a rod channel dimensioned to guide a spinal rod into the bone anchor assembly;
  a bone anchor engagement feature at the distal end, wherein the bone anchor engagement feature is fixedly attached to the bone anchor assembly; and
  a side track extending longitudinally between the pair of opposed longitudinal rod slots,
  wherein the side track is configured to receive a guide member attachment feature of a pivot rack, wherein the guide member attachment feature has a broad portion and a narrower portion to allow the guide member attachment feature to be freely slid in the side track while constrained from moving radially with regard to the guide member, and
  wherein the guide member is configured to rotate around a rotation axis perpendicular to the longitudinal axis when the guide member attachment feature is seated in the side track.

20. The guide member of claim 19, wherein the bone anchor assembly comprises:
  a bone anchor configured to engage bone; and
  a housing configured to couple to the bone anchor and engage the spinal rod,
  wherein the housing comprises a base configured to mate with the bone anchor, a pair of arms separated by a rod channel configured to receive the spinal rod therein, and an attachment groove configured to engage the bone anchor engagement feature of the guide member.

* * * * *